(12) United States Patent
Buyse

(10) Patent No.: US 11,142,569 B2
(45) Date of Patent: Oct. 12, 2021

(54) SERUM ALBUMIN-BINDING IMMUNOGLOBULIN VARIABLE DOMAINS

(71) Applicant: Ablynx N.V., Ghent-Zwijnaarde (BE)

(72) Inventor: Marie-Ange Buyse, Merelbeke (BE)

(73) Assignee: Ablynx N.V., Zwijnaarde (BE)

( * ) Notice: Subject to any disclaimer, the term of this patent is extended or adjusted under 35 U.S.C. 154(b) by 0 days.

(21) Appl. No.: 15/769,800

(22) PCT Filed: Oct. 28, 2016

(86) PCT No.: PCT/EP2016/076088
§ 371 (c)(1),
(2) Date: Apr. 20, 2018

(87) PCT Pub. No.: WO2017/080850
PCT Pub. Date: May 18, 2017

(65) Prior Publication Data
US 2018/0312578 A1 Nov. 1, 2018

Related U.S. Application Data

(60) Provisional application No. 62/254,813, filed on Nov. 13, 2015.

(51) Int. Cl.
*C07K 16/18* (2006.01)
*C07K 16/42* (2006.01)

(52) U.S. Cl.
CPC .......... *C07K 16/18* (2013.01); *C07K 16/4241* (2013.01); *C07K 2317/34* (2013.01); *C07K 2317/565* (2013.01); *C07K 2317/567* (2013.01); *C07K 2317/569* (2013.01)

(58) Field of Classification Search
CPC .................... C07K 2317/565; C07K 2317/569
USPC ..................................... 424/133.1; 530/387.3
See application file for complete search history.

(56) References Cited

U.S. PATENT DOCUMENTS

| | | | | |
|---|---|---|---|---|
| 8,679,496 B2 * | 3/2014 | Coulstock | ............ | C07K 16/18 424/133.1 |
| 9,005,963 B2 * | 4/2015 | Blanchetot | ............ | A61P 31/04 435/326 |
| 9,012,609 B2 * | 4/2015 | Arulanantham | ....... | C07K 16/18 424/135.1 |
| 9,803,018 B2 * | 10/2017 | Blanchetot | ............ | A61P 31/12 |
| 9,850,307 B2 * | 12/2017 | Beaton | ..................... | A61P 37/02 |
| 10,287,340 B2 * | 5/2019 | Dimitrov | ............ | A61K 47/6841 |
| 10,414,828 B2 * | 9/2019 | Gschwind | ............ | C07K 16/22 |
| 2012/0114647 A1 * | 5/2012 | Coulstock | ............ | C07K 16/18 424/134.1 |
| 2013/0202597 A1 * | 8/2013 | Arulanantham | ....... | C07K 16/18 424/134.1 |
| 2013/0266567 A1 * | 10/2013 | Arulanantham | ....... | C07K 16/18 424/135.1 |
| 2014/0140996 A1 * | 5/2014 | Coulstock | ............ | C07K 16/18 424/134.1 |
| 2016/0052998 A1 * | 2/2016 | Arulanantham | ....... | C07K 16/18 536/23.53 |

FOREIGN PATENT DOCUMENTS

| | | |
|---|---|---|
| JP | 2012-532620 A | 12/2012 |
| JP | 2014-501515 A | 1/2014 |
| WO | WO 2011/006915 A2 | 1/2011 |
| WO | WO 2012/072731 A2 | 6/2012 |
| WO | WO 2012/175741 A2 | 12/2012 |
| WO | WO 2014/111550 A1 | 7/2014 |
| WO | WO 2015/173325 A2 | 11/2015 |

OTHER PUBLICATIONS

Ward et al. (Nature 341:544-546 (1989)).*
Smith-Gill et al. (J. Immunol. 139:4135-4144 (1987)).*
Kumar et al. (J. Biol. Chem. 275:35129-35136 (2000)).*
Song et al. (Biochem Biophys Res Comm 268:390-394 (2000)).*
Dufner (Trends Biotechnol. 24(11):523-29 (2006)).*
Jones et al., Deimmunization of monoclonal antibodies. Methods Mol Biol. 2009;525:405-23, xiv. doi:10.1007/978-1-59745-554-1_21.
Morris, Epitope Mapping; B-cell Epitopes. Encyclopedia of Life Sciences. Epub Sep. 28, 2007. Retrieved on Mar. 22, 2019 from https://onlinelibrary.wiley.com/doi/pdf/10.1002/9780470015902.a0002624.pub2. 3 pages.
Muyldermans, Single domain camel antibodies: current status. J Biotechnol. Jun. 2001;74(4):277-302.
Riechmann et al., Single domain antibodies: comparison of camel VH and camelised human VH domains. J Immunol Methods. Dec. 10, 1999;231(1-2):25-38.
PCT/EP2016/076088, Jan. 16, 2017, International Search Report and Written Opinion.
PCT/EP2016/076088, May 24, 2018, International Preliminary Report on Patentability.
Johnson et al., Kabat Database and its applications: 30 years after the first variability plot. Nucleic Acids Res. Jan. 1, 2000; 28(1): 214-218. doi: 10.1093/nar/28.1.214.
Johnson et al., Kabat Database and its applications: future directions. Nucleic Acids Res. Jan. 1, 2001; 29(1): 205-206. doi: 10.1093/nar/29.1.205.

(Continued)

*Primary Examiner* — Lynn A Bristol
(74) *Attorney, Agent, or Firm* — Wolf, Greenfield & Sacks, P.C.

(57) ABSTRACT

The present invention relates to amino acid sequences binding to serum albumin. In particular, the present invention relates to improved immunoglobulin single variable domains (also referred to herein as "ISV's" or "ISVD's"), and more in particular improved heavy-chain immunoglobulin single variable domains, binding to serum albumin, as well as to proteins, polypeptides and other constructs, compounds, molecules or chemical entities that comprise such improved serum albumin binders.

11 Claims, 27 Drawing Sheets
Specification includes a Sequence Listing.

(56) References Cited

OTHER PUBLICATIONS

Kabat et al., Sequences of Proteins of of Immunological Interest. vol. I. 5th Ed. US Department of Health and Human Services. Public Health Service. National Institutes of Health. 1991. 11 pages.
Martin, Chapter 3: Protein Sequence and Structure Analysis of Antibody Variable Domains. In Antibody Engineering vol. 2. Springer Lab Manuals. Springer, Berlin, Heidelberg. 2010:33-51. doi: 10.1007/978-3-642-01147-4_3.

* cited by examiner

Figure 1

| Numbering according to Kabat (VH) | Numbering according to Chothia (VH) | Aho numbering | IMGT |
|---|---|---|---|
| 11 | 11 | 12 | 12 |
| 14 | 14 | 15 | 15 |
| 41 | 41 | 48 | 46 |
| 42 | 42 | 49 | 47 |
| 87 | 87 | 101 | 99 |
| 89 | 89 | 103 | 101 |
| 108 | 108 | 144 | --- |
| 110 | 110 | 146 | --- |
| 112 | 112 | 148 | --- |

Source: bioc.uzh.ch/plueckthun/antibody/Numbering/NumFrame.html

Figure 2

```
                    20                    40                         60
           EVQLLESGGG LVQPGGSLRL SCAASGFTFS TGEMAWVRQA PGKGLEWVSS ISSSGATTYY  60
DOM7r-92
DOM7r-92-4    ........ .......... .......... D.SS.L.... .......... .HQ...TP..  60
DOM7r-92-100  ........ .......... .......... D.SS.L.... ........V. .HQ...TP..  60
DOM7r-92-104  ........ .......... .......... D.SS.L.... ........V. .HQ...TP..  60

80                   100                        120
           ADSVKGRFTI SRDNSKNTLY LQMNSLRAED TAVYYCAKPR HPQGGVTFDY WGQGTLVTVS  120
DOM7r-92
DOM7r-92-4    .......... .......... .......... ---------- F.STHGK... ..........  118
DOM7r-92-100  .......... .......... .......... ---------- F.SSRMK... ..........  118
DOM7r-92-104  .......... .......... .......... ---------- F.SSRMK... ..........  118

DOM7r-92      S - 121
DOM7r-92-4    . - 119
DOM7r-92-100  . - 119
DOM7r-92-104  . A 120
```

Figure 3

| SEQ ID NO: | Clone | Sequence |
|---|---|---|
| 1 | reference A: DOM7r-92 (WO2011/006915 - SEQ ID NO: 184) | EVQLLESGGGLVQPGGSLRLSCAASGFTFSTGEMAWVRQAPGKGLEWVSSISSSGATTYYADSVKGRFTISRDNSKNTLYLQMNSLRAEDTAVYYCAKPRHPQGGVTFDYWGQGTLVTVSS |
| 2 | reference B: DOM7r-92-4 (WO2011/006915 - SEQ ID NO: 201) | EVQLLESGGGLVQPGGSLRLSCAASGFTFDTSSMLWVRQAPGKGLEWVSVIHQSGTPTYYADSVKGRFTISRDNSKNTLYLQMNSLRAEDTAVYYCAKFPSTHGKFDYWGQGTLVTVSS |
| 3 | reference C: DOM7r-92-100 (WO2014/111550 - SEQ ID NO: 4) | EVQLLESGGGLVQPGGSLRLSCAASGFTFDTSSMLWVRQAPGKGLEWVSVIHQSGTPTYYADSVKGRFTISRDNSKNTLYLQMNSLRAEDTAVYYCAKFPSSRMKFDYWGQGTLVTVSS |
| 4 | reference D: DOM7r-92-104 (WO2014/111550 - SEQ ID NO: 6) | EVQLLESGGGLVQPGGSLRLSCAASGFTFDTSSMLWVRQAPGKGLEWVSVIHQSGTPTYYADSVKGRFTISRDNSKNTLYLQMNSLRAEDTAVYYCAKFPSSRMKFDYWGQGTLVTVSSA |
| 5 | CDR1 (Kabat) | TGEMA |
| 6 | CDR2 (Kabat) | SISSSGATTYYADSVKG |
| 7 | CDR3 (Kabat/Abm) | PRHPQGGVTFDY |
| 8 | CDR1 (Abm) | GFTFSTGEMA |
| 9 | CDR2 (Abm) | SISSSGATTY |
| 10 | CDR1 (Kabat) | TSSML |
| 11 | CDR2 (Kabat) | VIHQSGTPTYYADSVKG |
| 12 | CDR3 (Kabat/Abm) | FPSTHGKFDY |
| 13 | CDR1 (Abm) | GFTFDTSSML |
| 14 | CDR2 (Abm) | VIHQSGTPTY |
| 15 | CDR3 (Kabat/Abm) | FPSSRMKFDY |

Figure 3 (continued)

| SEQ ID NO: | Clone | Sequence |
|---|---|---|
| 16 | SEQ ID NO: 1 (89L + 110K) | EVQLLESGGGLVQPGGSLRLSCAASGFTFSTGEMAWVRQAPGKGLEWVSSISSSGATTYYADSVKGRFTISRDNSKNTLYLQMNSLRAEDTALYYCAKPRHPQGGVTFDYWGQGTLVTVKS |
| 17 | SEQ ID NO: 1 (89L + 110Q) | EVQLLESGGGLVQPGGSLRLSCAASGFTFSTGEMAWVRQAPGKGLEWVSISSSGATTYYADSVKGRFTISRDNSKNTLYLQMNSLRAEDTALYYCAKPRHPQGGVTFDYWGQGTLVQSS |
| 18 | SEQ ID NO: 1 (89L + 112K) | EVQLLESGGGLVQPGGSLRLSCAASGFTFSTGEMAWVRQAPGKGLEWVSSISSSGATTYYADSVKGRFTISRDNSKNTLYLQMNSLRAEDTALYYCAKPRHPQGGVTFDYWGQGTLVTVKS |
| 19 | SEQ ID NO: 1 (89L + 112Q) | EVQLLESGGGLVQPGGSLRLSCAASGFTFSTGEMAWVRQAPGKGLEWVSSISSSGATTYYADSVKGRFTISRDNSKNTLYLQMNSLRAEDTALYYCAKPRHPQGGVTFDYWGQGTLVTVQS |
| 20 | SEQ ID NO: 1 (11V+89L+112K) | EVQLLESGGGVVQPGGSLRLSCAASGFTFSTGEMAWVRQAPGKGLEWVSSISSSGATTYYADSVKGRFTISRDNSKNTLYLQMNSLRAEDTALYYCAKPRHPQGGVTFDYWGQGTLVTVKS |
| 21 | SEQ ID NO: 1 (11V + 89L +112Q) | EVQLLESGGGVVQPGGSLRLSCAASGFTFSTGEMAWVRQAPGKGLEWVSSISSSGATTYYADSVKGRFTISRDNSKNTLYLQMNSLRAEDTALYYCAKPRHPQGGVTFDYWGQGTLVTVQS |
| 22 | SEQ ID NO: 1 (89T) | EVQLLESGGGLVQPGGSLRLSCAASGFTFSTGEMAWVRQAPGKGLEWVSSISSSGATTYYADSVKGRFTISRDNSKNTLYLQMNSLRAEDTATYYCAKPRHPQGGVTFDYWGQGTLVTVSS |
| 23 | SEQ ID NO: 1 (11V + 89L) | EVQLLESGGGVVQPGGSLRLSCAASGFTFSTGEMAWVRQAPGKGLEWVSSISSSGATTYYADSVKGRFTISRDNSKNTLYLQMNSLRAEDTALYYCAKPRHPQGGVTFDYWGQGTLVTVSS |
| 24 | SEQ ID NO: 1 (11V + 89L + 110K) | EVQLLESGGGVVQPGGSLRLSCAASGFTFSTGEMAWVRQAPGKGLEWVSSISSSGATTYYADSVKGRFTISRDNSKNTLYLQMNSLRAEDTALYYCAKPRHPQGGVTFDYWGQGTLVKVSS |
| 25 | SEQ ID NO: 1 (11V + 89L + 110Q) | EVQLLESGGGVVQPGGSLRLSCAASGFTFSTGEMAWVRQAPGKGLEWVSSISSSGATTYYADSVKGRFTISRDNSKNTLYLQMNSLRAEDTALYYCAKPRHPQGGVTFDYWGQGTLVQVSS |
| 26 | SEQ ID NO: 1 (11V + 110K) | EVQLLESGGGVVQPGGSLRLSCAASGFTFSTGEMAWVRQAPGKGLEWVSSISSSGATTYYADSVKGRFTISRDNSKNTLYLQMNSLRAEDTAVYYCAKPRHPQGGVTFDYWGQGTLVKVSS |

Figure 3 (continued)

| SEQ ID NO: | Clone | Sequence |
|---|---|---|
| 27 | SEQ ID NO:1 (I1V + 110Q) | EVQLLESGGGVVQPGGSLRLSCAASGFTFSTGEMAWVRQAPGKGLEWVSSISSSGATTYYADS VKGRFTISRDNSKNTLYLQMNSLRAEDTAVYYCAKPRHPQGGVTFDYWGQGTLVQVSS |
| 28 | SEQ ID NO:1 (I1V + 112K) | EVQLLESGGGVVQPGGSLRLSCAASGFTFSTGEMAWVRQAPGKGLEWVSSISSSGATTYYADS VKGRFTISRDNSKNTLYLQMNSLRAEDTAVYYCAKPRHPQGGVTFDYWGQGTLVTVKS |
| 29 | SEQ ID NO:1 (I1V + 112Q) | EVQLLESGGGVVQPGGSLRLSCAASGFTFSTGEMAWVRQAPGKGLEWVSSISSSGATTYYADS VKGRFTISRDNSKNTLYLQMNSLRAEDTAVYYCAKPRHPQGGVTFDYWGQGTLVTVQS |
| 30 | SEQ ID NO:1 (89L + 110K)+ A | EVQLLESGGGLVQPGGSLRLSCAASGFTFSTGEMAWVRQAPGKGLEWVSSISSSGATTYYADS VKGRFTISRDNSKNTLYLQMNSLRAEDTALYYCAKPRHPQGGVTFDYWGQGTLVKVSSA |
| 31 | SEQ ID NO:1 (89L + 110Q)+ A | EVQLLESGGGLVQPGGSLRLSCAASGFTFSTGEMAWVRQAPGKGLEWVSSISSSGATTYYADS VKGRFTISRDNSKNTLYLQMNSLRAEDTALYYCAKPRHPQGGVTFDYWGQGTLVQVSSA |
| 32 | SEQ ID NO:1 (89L + 112K)+ A | EVQLLESGGGLVQPGGSLRLSCAASGFTFSTGEMAWVRQAPGKGLEWVSSISSSGATTYYADS VKGRFTISRDNSKNTLYLQMNSLRAEDTALYYCAKPRHPQGGVTFDYWGQGTLVTVKSA |
| 33 | SEQ ID NO:1 (89L + 112Q)+ A | EVQLLESGGGLVQPGGSLRLSCAASGFTFSTGEMAWVRQAPGKGLEWVSSISSSGATTYYADS VKGRFTISRDNSKNTLYLQMNSLRAEDTALYYCAKPRHPQGGVTFDYWGQGTLVTVQSA |
| 34 | SEQ ID NO:1 (I1V+89L+112K)+ A | EVQLLESGGGVVQPGGSLRLSCAASGFTFSTGEMAWVRQAPGKGLEWVSSISSSGATTYYADS VKGRFTISRDNSKNTLYLQMNSLRAEDTALYYCAKPRHPQGGVTFDYWGQGTLVTVKSA |
| 35 | SEQ ID NO:1 (I1V + 89L +112Q)+ A | EVQLLESGGGVVQPGGSLRLSCAASGFTFSTGEMAWVRQAPGKGLEWVSSISSSGATTYYADS VKGRFTISRDNSKNTLYLQMNSLRAEDTALYYCAKPRHPQGGVTFDYWGQGTLVTVQSA |
| 36 | SEQ ID NO:1 (89T)+ A | EVQLLESGGGVVQPGGSLRLSCAASGFTFSTGEMAWVRQAPGKGLEWVSSISSSGATTYYADS VKGRFTISRDNSKNTLYLQMNSLRAEDTATYYCAKPRHPQGGVTFDYWGQGTLVTVSSA |
| 37 | SEQ ID NO:1 (I1V + 89L)+ A | EVQLLESGGGVVQPGGSLRLSCAASGFTFSTGEMAWVRQAPGKGLEWVSSISSSGATTYYADS VKGRFTISRDNSKNTLYLQMNSLRAEDTALYYCAKPRHPQGGVTFDYWGQGTLVTVSSA |

Figure 3 (continued)

| SEQ ID NO: | Clone | Sequence |
|---|---|---|
| 38 | SEQ ID NO: 1 (11V + 89L + 110K)+ A | EVQLLESGGGVVQPGGSLRLSCAASGFTFSTGEMAWVRQAPGKGLEWVSSISSSGATTYYADSVKGRFTISRDNSKNTLYLQMNSLRAEDTALYYCAKPRHPQGGVTFDYWGQGTLVKVSSA |
| 39 | SEQ ID NO: 1 (11V + 89L + 110Q)+ A | EVQLLESGGGVVQPGGSLRLSCAASGFTFSTGEMAWVRQAPGKGLEWVSSISSSGATTYYADSVKGRFTISRDNSKNTLYLQMNSLRAEDTALYYCAKPRHPQGGVTFDYWGQGTLVQVSSA |
| 40 | SEQ ID NO: 1 (11V + 110K)+ A | EVQLLESGGGVVQPGGSLRLSCAASGFTFSTGEMAWVRQAPGKGLEWVSSISSSGATTYYADSVKGRFTISRDNSKNTLYLQMNSLRAEDTAVYYCAKPRHPQGGVTFDYWGQGTLVKVSSA |
| 41 | SEQ ID NO: 1 (11V + 110Q)+ A | EVQLLESGGGVVQPGGSLRLSCAASGFTFSTGEMAWVRQAPGKGLEWVSSISSSGATTYYADSVKGRFTISRDNSKNTLYLQMNSLRAEDTAVYYCAKPRHPQGGVTFDYWGQGTLVQVSSA |
| 42 | SEQ ID NO: 1 (11V + 112K)+ A | EVQLLESGGGVVQPGGSLRLSCAASGFTFSTGEMAWVRQAPGKGLEWVSSISSSGATTYYADSVKGRFTISRDNSKNTLYLQMNSLRAEDTAVYYCAKPRHPQGGVTFDYWGQGTLVTVKSA |
| 43 | SEQ ID NO: 1 (11V + 112Q)+ A | EVQLLESGGGVVQPGGSLRLSCAASGFTFSTGEMAWVRQAPGKGLEWVSSISSSGATTYYADSVKGRFTISRDNSKNTLYLQMNSLRAEDTAVYYCAKPRHPQGGVTFDYWGQGTLVTVQSA |
| 44 | SEQ ID NO: 2 (89L + 110K) | EVQLLESGGGLVQPGGSLRLSCAASGFTFDTSSMLWVRQAPGKGLEWVSVIHQSGTPTYYADSVKGRFTISRDNSKNTLYLQMNSLRAEDTALYYCAKFPSTHGKFDYWGQGTLVKVSS |
| 45 | SEQ ID NO: 2 (89L + 110Q) | EVQLLESGGGLVQPGGSLRLSCAASGFTFDTSSMLWVRQAPGKGLEWVSVIHQSGTPTYYADSVKGRFTISRDNSKNTLYLQMNSLRAEDTALYYCAKFPSTHGKFDYWGQGTLVQVSS |
| 46 | SEQ ID NO: 2 (89L + 112K) | EVQLLESGGGLVQPGGSLRLSCAASGFTFDTSSMLWVRQAPGKGLEWVSVIHQSGTPTYYADSVKGRFTISRDNSKNTLYLQMNSLRAEDTALYYCAKFPSTHGKFDYWGQGTLVTVSS |
| 47 | SEQ ID NO: 2 (89L + 112Q) | EVQLLESGGGLVQPGGSLRLSCAASGFTFDTSSMLWVRQAPGKGLEWVSVIHQSGTPTYYADSVKGRFTISRDNSKNTLYLQMNSLRAEDTALYYCAKFPSTHGKFDYWGQGTLVTVQS |
| 48 | SEQ ID NO: 2 (11V+89L+112K) | EVQLLESGGGVVQPGGSLRLSCAASGFTFDTSSMLWVRQAPGKGLEWVSVIHQSGTPTYYADSVKGRFTISRDNSKNTLYLQMNSLRAEDTALYYCAKFPSTHGKFDYWGQGTLVTVKS |

Figure 3 (continued)

| SEQ ID NO: | Clone | Sequence |
|---|---|---|
| 49 | SEQ ID NO: 2 (11V + 89L +112Q) | EVQLLESGGGVVQPGGSLRLSCAASGFTFDTSSMLWVRQAPGKGLEWVSVIHQSGTPTYYADSV KGRFTISRDNSKNTLYLQMNSLRAEDTALYYCAKFPSTHGKFDYWGQGTLVTVQS |
| 50 | SEQ ID NO: 2 (89T) | EVQLLESGGGLVQPGGSLRLSCAASGFTFDTSSMLWVRQAPGKGLEWVSVIHQSGTPTYYADSV KGRFTISRDNSKNTLYLQMNSLRAEDTATYYCAKFPSTHGKFDYWGQGTLVTVSS |
| 51 | SEQ ID NO: 2 (11V + 89L) | EVQLLESGGGVVQPGGSLRLSCAASGFTFDTSSMLWVRQAPGKGLEWVSVIHQSGTPTYYADSV KGRFTISRDNSKNTLYLQMNSLRAEDTALYYCAKFPSTHGKFDYWGQGTLVTVSS |
| 52 | SEQ ID NO: 2 (11V + 89L + 110K) | EVQLLESGGGVVQPGGSLRLSCAASGFTFDTSSMLWVRQAPGKGLEWVSVIHQSGTPTYYADSV KGRFTISRDNSKNTLYLQMNSLRAEDTALYYCAKFPSTHGKFDYWGQGTLVTVKSS |
| 53 | SEQ ID NO: 2 (11V + 89L + 110Q) | EVQLLESGGGVVQPGGSLRLSCAASGFTFDTSSMLWVRQAPGKGLEWVSVIHQSGTPTYYADSV KGRFTISRDNSKNTLYLQMNSLRAEDTALYYCAKFPSTHGKFDYWGQGTLVQVSS |
| 54 | SEQ ID NO: 2 (11V + 110K) | EVQLLESGGGVVQPGGSLRLSCAASGFTFDTSSMLWVRQAPGKGLEWVSVIHQSGTPTYYADSV KGRFTISRDNSKNTLYLQMNSLRAEDTAVYYCAKFPSTHGKFDYWGQGTLVKVSS |
| 55 | SEQ ID NO: 2 (11V + 110Q) | EVQLLESGGGVVQPGGSLRLSCAASGFTFDTSSMLWVRQAPGKGLEWVSVIHQSGTPTYYADSV KGRFTISRDNSKNTLYLQMNSLRAEDTAVYYCAKFPSTHGKFDYWGQGTLVQVSS |
| 56 | SEQ ID NO: 2 (11V + 112K) | EVQLLESGGGVVQPGGSLRLSCAASGFTFDTSSMLWVRQAPGKGLEWVSVIHQSGTPTYYADSV KGRFTISRDNSKNTLYLQMNSLRAEDTAVYYCAKFPSTHGKFDYWGQGTLVTVKS |
| 57 | SEQ ID NO: 2 (11V + 112Q) | EVQLLESGGGVVQPGGSLRLSCAASGFTFDTSSMLWVRQAPGKGLEWVSVIHQSGTPTYYADSV KGRFTISRDNSKNTLYLQMNSLRAEDTAVYYCAKFPSTHGKFDYWGQGTLVTVQS |
| 58 | SEQ ID NO: 2 (89L + 110K) + A | EVQLLESGGGLVQPGGSLRLSCAASGFTFDTSSMLWVRQAPGKGLEWVSVIHQSGTPTYYADSV KGRFTISRDNSKNTLYLQMNSLRAEDTALYYCAKFPSTHGKFDYWGQGTLVKVSSA |
| 59 | SEQ ID NO: 2 (89L + 110Q) + A | EVQLLESGGGLVQPGGSLRLSCAASGFTFDTSSMLWVRQAPGKGLEWVSVIHQSGTPTYYADSV KGRFTISRDNSKNTLYLQMNSLRAEDTALYYCAKFPSTHGKFDYWGQGTLVQVSSA |

Figure 3 (continued)

| SEQ ID NO: | Clone | Sequence |
|---|---|---|
| 60 | SEQ ID NO: 2 (89L + 112K) + A | EVQLLESGGGLVQPGGSLRLSCAASGFTFDTSSMLWVRQAPGKGLEWVSVIHQSGTPTYYAD SVKGRFTISRDNSKNTLYLQMNSLRAEDTALYYCAKFPSTHGKFDYWGQGTLVQVKSA |
| 61 | SEQ ID NO: 2 (89L + 112Q) + A | EVQLLESGGGLVQPGGSLRLSCAASGFTFDTSSMLWVRQAPGKGLEWVSVIHQSGTPTYYAD SVKGRFTISRDNSKNTLYLQMNSLRAEDTALYYCAKFPSTHGKFDYWGQGTLVTVQSA |
| 62 | SEQ ID NO: 2 (I1V+89L+112K) + A | EVQLLESGGGVVQPGGSLRLSCAASGFTFDTSSMLWVRQAPGKGLEWVSVIHQSGTPTYYAD SVKGRFTISRDNSKNTLYLQMNSLRAEDTALYYCAKFPSTHGKFDYWGQGTLVTVKSA |
| 63 | SEQ ID NO: 2 (I1V + 89L +112Q) + A | EVQLLESGGGVVQPGGSLRLSCAASGFTFDTSSMLWVRQAPGKGLEWVSVIHQSGTPTYYAD SVKGRFTISRDNSKNTLYLQMNSLRAEDTATYYCAKFPSTHGKFDYWGQGTLVTVQSA |
| 64 | SEQ ID NO: 2 (89T) + A | EVQLLESGGGLVQPGGSLRLSCAASGFTFDTSSMLWVRQAPGKGLEWVSVIHQSGTPTYYAD SVKGRFTISRDNSKNTLYLQMNSLRAEDTATYYCAKFPSTHGKFDYWGQGTLVTVSSA |
| 65 | SEQ ID NO: 2 (I1V + 89L) + A | EVQLLESGGGVVQPGGSLRLSCAASGFTFDTSSMLWVRQAPGKGLEWVSVIHQSGTPTYYAD SVKGRFTISRDNSKNTLYLQMNSLRAEDTALYYCAKFPSTHGKFDYWGQGTLVTVSSA |
| 66 | SEQ ID NO: 2 (I1V + 89L + 110K) + A | EVQLLESGGGVVQPGGSLRLSCAASGFTFDTSSMLWVRQAPGKGLEWVSVIHQSGTPTYYAD SVKGRFTISRDNSKNTLYLQMNSLRAEDTALYYCAKFPSTHGKFDYWGQGTLVKVSSA |
| 67 | SEQ ID NO: 2 (I1V + 89L + 110Q) + A | EVQLLESGGGVVQPGGSLRLSCAASGFTFDTSSMLWVRQAPGKGLEWVSVIHQSGTPTYYAD SVKGRFTISRDNSKNTLYLQMNSLRAEDTALYYCAKFPSTHGKFDYWGQGTLVQVSSA |
| 68 | SEQ ID NO: 2 (I1V + 110K) + A | EVQLLESGGGVVQPGGSLRLSCAASGFTFDTSSMLWVRQAPGKGLEWVSVIHQSGTPTYYAD SVKGRFTISRDNSKNTLYLQMNSLRAEDTAVYYCAKFPSTHGKFDYWGQGTLVKVSSA |
| 69 | SEQ ID NO: 2 (I1V + 110Q) + A | EVQLLESGGGVVQPGGSLRLSCAASGFTFDTSSMLWVRQAPGKGLEWVSVIHQSGTPTYYAD SVKGRFTISRDNSKNTLYLQMNSLRAEDTAVYYCAKFPSTHGKFDYWGQGTLVQVSSA |
| 70 | SEQ ID NO: 2 (I1V + 112K) + A | EVQLLESGGGVVQPGGSLRLSCAASGFTFDTSSMLWVRQAPGKGLEWVSVIHQSGTPTYYAD SVKGRFTISRDNSKNTLYLQMNSLRAEDTAVYYCAKFPSTHGKFDYWGQGTLVTVKSA |

Figure 3 (continued)

| SEQ ID NO: | Clone | Sequence |
|---|---|---|
| 71 | SEQ ID NO: 2 (11V + 112Q) + A | EVQLLESGGGVVQPGGSLRLSCAASGFTFDTSSMLWVRQAPGKGLEWVSVIHQSGTPTYYADSV KGRFTISRDNSKNTLYLQMNSLRAEDTAVYYCAKFPSTHGKFDYWGQGTLVTVQSA |
| 72 | SEQ ID NO: 3 (89L + 110K) | EVQLLESGGGLVQPGGSLRLSCAASGFTFDTSSMLWVRQAPGKGLEWVSVIHQSGTPTYYADSV KGRFTISRDNSKNTLYLQMNSLRAEDTALYYCAKFPSSRMKFDYWGQGTLVKVSS |
| 73 | SEQ ID NO: 3 (89L + 110Q) | EVQLLESGGGLVQPGGSLRLSCAASGFTFDTSSMLWVRQAPGKGLEWVSVIHQSGTPTYYADSV KGRFTISRDNSKNTLYLQMNSLRAEDTALYYCAKFPSSRMKFDYWGQGTLVKVSS |
| 74 | SEQ ID NO: 3 (89L + 112K) | EVQLLESGGGLVQPGGSLRLSCAASGFTFDTSSMLWVRQAPGKGLEWVSVIHQSGTPTYYADSV KGRFTISRDNSKNTLYLQMNSLRAEDTALYYCAKFPSSRMKFDYWGQGTLVTVKS |
| 75 | SEQ ID NO: 3 (89L + 112Q) | EVQLLESGGGLVQPGGSLRLSCAASGFTFDTSSMLWVRQAPGKGLEWVSVIHQSGTPTYYADSV KGRFTISRDNSKNTLYLQMNSLRAEDTALYYCAKFPSSRMKFDYWGQGTLVTVQS |
| 76 | SEQ ID NO: 3 (11V+89L+112K) | EVQLLESGGGVVQPGGSLRLSCAASGFTFDTSSMLWVRQAPGKGLEWVSVIHQSGTPTYYADSV KGRFTISRDNSKNTLYLQMNSLRAEDTALYYCAKFPSSRMKFDYWGQGTLVTVKS |
| 77 | SEQ ID NO: 3 (11V + 89L +112Q) | EVQLLESGGGVVQPGGSLRLSCAASGFTFDTSSMLWVRQAPGKGLEWVSVIHQSGTPTYYADSV KGRFTISRDNSKNTLYLQMNSLRAEDTALYYCAKFPSSRMKFDYWGQGTLVTVQS |
| 78 | SEQ ID NO: 3 (89T) | EVQLLESGGGLVQPGGSLRLSCAASGFTFDTSSMLWVRQAPGKGLEWVSVIHQSGTPTYYADSV KGRFTISRDNSKNTLYLQMNSLRAEDTATYYCAKFPSSRMKFDYWGQGTLVTVSS |
| 79 | SEQ ID NO: 3 (11V + 89L) | EVQLLESGGGVVQPGGSLRLSCAASGFTFDTSSMLWVRQAPGKGLEWVSVIHQSGTPTYYADSV KGRFTISRDNSKNTLYLQMNSLRAEDTALYYCAKFPSSRMKFDYWGQGTLVTVSS |
| 80 | SEQ ID NO: 3 (11V + 89L + 110K) | EVQLLESGGGVVQPGGSLRLSCAASGFTFDTSSMLWVRQAPGKGLEWVSVIHQSGTPTYYADSV KGRFTISRDNSKNTLYLQMNSLRAEDTALYYCAKFPSSRMKFDYWGQGTLVKVSS |
| 81 | SEQ ID NO: 3 (11V + 89L + 110Q) | EVQLLESGGGVVQPGGSLRLSCAASGFTFDTSSMLWVRQAPGKGLEWVSVIHQSGTPTYYADSV KGRFTISRDNSKNTLYLQMNSLRAEDTALYYCAKFPSSRMKFDYWGQGTLVQVSS |

Figure 3 (continued)

| SEQ ID NO: | Clone | Sequence |
|---|---|---|
| 82 | SEQ ID NO: 3 (11V + 110K) | EVQLLESGGGVVQPGGSLRLSCAASGFTFDTSSMLWVRQAPGKGLEWVSVIHQSGTPTYYADSVKGRFTISRDNSKNTLYLQMNSLRAEDTAVYYCAKFPSSRMKFDYWGQGTLVKVSS |
| 83 | SEQ ID NO: 3 (11V + 110Q) | EVQLLESGGGVVQPGGSLRLSCAASGFTFDTSSMLWVRQAPGKGLEWVSVIHQSGTPTYYADSVKGRFTISRDNSKNTLYLQMNSLRAEDTAVYYCAKFPSSRMKFDYWGQGTLVQVSS |
| 84 | SEQ ID NO: 3 (11V + 112K) | EVQLLESGGGVVQPGGSLRLSCAASGFTFDTSSMLWVRQAPGKGLEWVSVIHQSGTPTYYADSVKGRFTISRDNSKNTLYLQMNSLRAEDTAVYYCAKFPSSRMKFDYWGQGTLVTVKS |
| 85 | SEQ ID NO: 3 (11V + 112Q) | EVQLLESGGGVVQPGGSLRLSCAASGFTFDTSSMLWVRQAPGKGLEWVSVIHQSGTPTYYADSVKGRFTISRDNSKNTLYLQMNSLRAEDTAVYYCAKFPSSRMKFDYWGQGTLVTVQS |
| 86 | SEQ ID NO: 4 (89L + 110K) | EVQLLESGGGLVQPGGSLRLSCAASGFTFDTSSMLWVRQAPGKGLEWVSVIHQSGTPTYYADSVKGRFTISRDNSKNTLYLQMNSLRAEDTALYYCAKFPSSRMKFDYWGQGTLVKVSSA |
| 87 | SEQ ID NO: 4 (89L + 110Q) | EVQLLESGGGLVQPGGSLRLSCAASGFTFDTSSMLWVRQAPGKGLEWVSVIHQSGTPTYYADSVKGRFTISRDNSKNTLYLQMNSLRAEDTALYYCAKFPSSRMKFDYWGQGTLVQVSSA |
| 88 | SEQ ID NO: 4 (89L + 112K) | EVQLLESGGGLVQPGGSLRLSCAASGFTFDTSSMLWVRQAPGKGLEWVSVIHQSGTPTYYADSVKGRFTISRDNSKNTLYLQMNSLRAEDTALYYCAKFPSSRMKFDYWGQGTLVTVKSA |
| 89 | SEQ ID NO: 4 (89L + 112Q) | EVQLLESGGGLVQPGGSLRLSCAASGFTFDTSSMLWVRQAPGKGLEWVSVIHQSGTPTYYADSVKGRFTISRDNSKNTLYLQMNSLRAEDTALYYCAKFPSSRMKFDYWGQGTLVTVQSA |
| 90 | SEQ ID NO: 4 (11V+89L+112K) | EVQLLESGGGLVQPGGSLRLSCAASGFTFDTSSMLWVRQAPGKGLEWVSVIHQSGTPTYYADSVKGRFTISRDNSKNTLYLQMNSLRAEDTALYYCAKFPSSRMKFDYWGQGTLVTVKSA |
| 91 | SEQ ID NO: 4 (11V + 89L +112Q) | EVQLLESGGGLVQPGGSLRLSCAASGFTFDTSSMLWVRQAPGKGLEWVSVIHQSGTPTYYADSVKGRFTISRDNSKNTLYLQMNSLRAEDTALYYCAKFPSSRMKFDYWGQGTLVTVQSA |
| 92 | SEQ ID NO: 4 (89T) | EVQLLESGGGLVQPGGSLRLSCAASGFTFDTSSMLWVRQAPGKGLEWVSVIHQSGTPTYYADSVKGRFTISRDNSKNTLYLQMNSLRAEDTATYYCAKFPSSRMKFDYWGQGTLVTVSSA |

Figure 3 (continued)

| SEQ ID NO: | Clone | Sequence |
|---|---|---|
| 93 | SEQ ID NO: 4 (11V + 89L) | EVQLLESGGGVVQPGGSLRLSCAASGFTFDTSSMLWVRQAPGKGLEWVSVIHQSGTPTYYADS VKGRFTISRDNSKNTLYLQMNSLRAEDTALYYCAKFPSSRMKFDYWGQGTLVTVSSA |
| 94 | SEQ ID NO: 4 (11V + 89L + 110K) | EVQLLESGGGVVQPGGSLRLSCAASGFTFDTSSMLWVRQAPGKGLEWVSVIHQSGTPTYYADS VKGRFTISRDNSKNTLYLQMNSLRAEDTALYYCAKFPSSRMKFDYWGQGTLVKVSSA |
| 95 | SEQ ID NO: 4 (11V + 89L + 110Q) | EVQLLESGGGVVQPGGSLRLSCAASGFTFDTSSMLWVRQAPGKGLEWVSVIHQSGTPTYYADS VKGRFTISRDNSKNTLYLQMNSLRAEDTALYYCAKFPSSRMKFDYWGQGTLVQVSSA |
| 96 | SEQ ID NO: 4 (11V + 110K) | EVQLLESGGGVVQPGGSLRLSCAASGFTFDTSSMLWVRQAPGKGLEWVSVIHQSGTPTYYADS VKGRFTISRDNSKNTLYLQMNSLRAEDTAVYYCAKFPSSRMKFDYWGQGTLVKVSSA |
| 97 | SEQ ID NO: 4 (11V + 110Q) | EVQLLESGGGVVQPGGSLRLSCAASGFTFDTSSMLWVRQAPGKGLEWVSVIHQSGTPTYYADS VKGRFTISRDNSKNTLYLQMNSLRAEDTAVYYCAKFPSSRMKFDYWGQGTLVQVSSA |
| 98 | SEQ ID NO: 4 (11V + 112K) | EVQLLESGGGVVQPGGSLRLSCAASGFTFDTSSMLWVRQAPGKGLEWVSVIHQSGTPTYYADS VKGRFTISRDNSKNTLYLQMNSLRAEDTAVYYCAKFPSSRMKFDYWGQGTLVTVKSA |
| 99 | SEQ ID NO: 4 (11V + 112Q) | EVQLLESGGGVVQPGGSLRLSCAASGFTFDTSSMLWVRQAPGKGLEWVSVIHQSGTPTYYADS VKGRFTISRDNSKNTLYLQMNSLRAEDTAVYYCAKFPSSRMKFDYWGQGTLVTVQSA |
| 100 | HIS6-FLAG3 tag | HHHHHHGAADYKDHDGDYKDHDIDYKDDDDKGAA |

Figure 3 (continued)

| SEQ ID NO | Description | Sequence |
|---|---|---|
| 101 | C-terminal end | VTVKS |
| 102 | C-terminal end | VTVQS |
| 103 | C-terminal end | VKVSS |
| 104 | C-terminal end | VQVSS |
| 105 | C-terminal end | VTVKSX(n) |
| 106 | C-terminal end | VTVQSX(n) |
| 107 | C-terminal end | VKVSSX(n) |
| 108 | C-terminal end | VQVSSX(n) |
| 109 | C-terminal end | VTVKSA |
| 110 | C-terminal end | VTVQSA |
| 111 | C-terminal end | VKVSSA |
| 112 | C-terminal end | VQVSSA |
| 113 | C-terminal end | VTVSS |
| 114 | C-terminal end | VTVSSX$_{(n)}$ |
| 115 | C-terminal end | VTVSSA |

Note: all compounds were tested with an N-terminal HIS6-FLAG3 tag

Figure 5

| Sample | Normalized PreAb binding levels (RU at 700) | | | % Reduction PreAb binding compared to Reference A | |
|---|---|---|---|---|---|
| | Reference A | Reference A L11V V89L + Ala | Reference A L11V V89L T110K + Ala | Reference A L11V V89L + Ala | Reference A L11V V89L T110K + Ala |
| IHuS#ABL-0042-02 | 117 | 109 | 98 | 6 | 16 |
| IHuS#ABL-0088-03 | 229 | 91 | 70 | 60 | 70 |
| IHuS#ABL-0137-01 | 140 | 119 | 99 | 15 | 29 |
| IHuS#ABL-0138-01 | 130 | 100 | 88 | 23 | 32 |
| IHuS#ABL-0139-01 | 150 | 104 | 92 | 31 | 39 |
| IHuS#ABL-0141-01 | 120 | 102 | 92 | 16 | 23 |
| IHuS#ABL-0149-01 | 173 | 108 | 96 | 37 | 44 |
| IHuS#ABL-0150-01 | 112 | 81 | 73 | 28 | 35 |
| IHuS#ABL-0151-01 | 232 | 127 | 110 | 45 | 53 |
| IHuS#ABL-0152-01 | 156 | 110 | 101 | 30 | 35 |
| IHuS#ABL-0153-01 | 170 | 83 | 73 | 51 | 57 |
| IHuS#ABL-0154-01 | 95 | 82 | 75 | 13 | 21 |
| IHuS#ABL-0159-01 | 124 | 106 | 90 | 15 | 27 |
| IHuS#ABL-0160-01 | 83 | 72 | 65 | 14 | 21 |
| IHuS#ABL-0161-01 | 132 | 125 | 106 | 5 | 20 |
| IHuS#ABL-0162-01 | 121 | 116 | 105 | 4 | 14 |
| IHuS#ABL-0148-01 | 434 | 106 | 93 | 76 | 79 |
| IHuS#ABL-0163-01 | 375 | 110 | 83 | 71 | 78 |
| IHuS#ABL-0171-01 | 122 | 111 | 96 | 9 | 21 |
| IHuS#ABL-0172-01 | 124 | 77 | 70 | 38 | 43 |
| IHuS#ABL-0218-01 | 194 | 128 | 110 | 34 | 43 |
| IHuS#ABL-0040-03 | 379 | 113 | 90 | 70 | 76 |
| IHuS#ABL-0090-02 | 540 | 123 | 76 | 77 | 86 |
| IHuS#ABL-0173-01 | 267 | 104 | 91 | 61 | 66 |
| IHuS#ABL-0188-01 | 136 | 121 | 104 | 10 | 23 |
| IHuS#ABL-0006-02 | 570 | 196 | 89 | 66 | 84 |
| IHuS#ABL-0189-01 | 132 | 117 | 99 | 11 | 25 |
| IHuS#ABL-0190-01 | 135 | 120 | 107 | 11 | 20 |
| IHuS#ABL-0191-01 | 97 | 90 | 79 | 7 | 18 |
| IHuS#ABL-0192-01 | 125 | 104 | 89 | 17 | 29 |
| IHuS#ABL-0198-01 | 145 | 123 | 103 | 15 | 29 |
| IHuS#ABL-0165-01 | 296 | 78 | 67 | 74 | 77 |

Figure 5 (continued)

| Sample | Reference A | Reference A L11V V89L + Ala | Reference A L11V V89L T110K + Ala | Reference A L11V V89L + Ala | Reference A L11V V89L T110K + Ala |
|---|---|---|---|---|---|
| IHuS#ABL-0199-01 | 389 | 164 | 114 | 58 | 71 |
| IHuS#ABL-0200-01 | 140 | 109 | 98 | 22 | 30 |
| IHuS#ABL-0201-01 | 150 | 110 | 90 | 27 | 40 |
| IHuS#ABL-0202-01 | 228 | 108 | 88 | 53 | 61 |
| IHuS#ABL-0044-02 | 120 | 116 | 98 | 4 | 18 |
| IHuS#ABL-0209-01 | 146 | 106 | 90 | 28 | 38 |
| IHuS#ABL-0210-01 | 136 | 120 | 102 | 12 | 25 |
| IHuS#ABL-0211-01 | 151 | 109 | 96 | 28 | 36 |
| IHuS#ABL-0212-01 | 231 | 111 | 101 | 52 | 56 |
| IHuS#ABL-0213-01 | 135 | 123 | 104 | 9 | 23 |
| IHuS#ABL-0183-01 | 407 | 141 | 101 | 65 | 75 |
| IHuS#ABL-0005-06 | 99 | 86 | 77 | 14 | 23 |
| IHuS#ABL-0219-01 | 146 | 124 | 103 | 15 | 29 |
| IHuS#ABL-0221-01 | 142 | 101 | 88 | 29 | 38 |
| IHuS#ABL-0222-01 | 253 | 105 | 93 | 58 | 63 |
| IHuS#ABL-0223-01 | 402 | 91 | 74 | 77 | 82 |
| IHuS#ABL-0142-01 | 139 | 113 | 97 | 19 | 30 |
| IHuS#ABL-0143-01 | 128 | 99 | 89 | 22 | 30 |
| IHuS#ABL-0144-01 | 181 | 120 | 102 | 34 | 44 |
| IHuS#ABL-0145-01 | 166 | 109 | 96 | 35 | 42 |
| IHuS#ABL-0146-01 | 165 | 102 | 88 | 38 | 46 |
| IHuS#ABL-0147-01 | 200 | 82 | 72 | 59 | 64 |
| IHuS#ABL-0031-04 | 82 | 51 | 33 | 38 | 60 |
| IHuS#ABL-0047-02 | 111 | 81 | 71 | 27 | 36 |
| IHuS#ABL-0155-01 | 166 | 117 | 94 | 29 | 43 |
| IHuS#ABL-0156-01 | 164 | 110 | 93 | 33 | 43 |
| IHuS#ABL-0157-01 | 371 | 113 | 93 | 70 | 75 |
| IHuS#ABL-0158-01 | 343 | 106 | 92 | 69 | 73 |
| IHuS#ABL-0164-01 | 123 | 120 | 105 | 2 | 14 |
| IHuS#ABL-0166-01 | 86 | 78 | 70 | 9 | 19 |
| IHuS#ABL-0167-01 | 253 | 131 | 88 | 48 | 65 |
| IHuS#ABL-0168-01 | 126 | 122 | 108 | 3 | 15 |
| IHuS#ABL-0169-01 | 124 | 99 | 87 | 20 | 30 |
| IHuS#ABL-0170-01 | 305 | 105 | 92 | 65 | 70 |
| IHuS#ABL-0174-01 | 108 | 104 | 89 | 4 | 18 |

Figure 5 (continued)

| Sample | Reference A | Reference A L11V V89L + Ala | Reference A L11V V89L T110K + Ala | Reference A L11V V89L + Ala | Reference A L11V V89L T110K + Ala |
|---|---|---|---|---|---|
| IHuS#ABL-0175-01 | 119 | 89 | 78 | 26 | 35 |
| IHuS#ABL-0176-01 | 148 | 131 | 113 | 12 | 24 |
| IHuS#ABL-0177-01 | 123 | 101 | 90 | 18 | 27 |
| IHuS#ABL-0178-01 | 114 | 110 | 96 | 3 | 16 |
| IHuS#ABL-0179-01 | 140 | 111 | 99 | 21 | 29 |
| IHuS#ABL-0193-01 | 265 | 133 | 112 | 50 | 58 |
| IHuS#ABL-0194-01 | 155 | 93 | 83 | 40 | 47 |
| IHuS#ABL-0195-01 | 399 | 133 | 105 | 67 | 74 |
| IHuS#ABL-0196-01 | 125 | 117 | 102 | 6 | 18 |
| IHuS#ABL-0180-01 | 118 | 102 | 89 | 13 | 25 |
| IHuS#ABL-0197-01 | 118 | 101 | 83 | 15 | 30 |
| IHuS#ABL-0204-01 | 94 | 91 | 79 | 3 | 17 |
| IHuS#ABL-0206-01 | 258 | 115 | 88 | 55 | 66 |
| IHuS#ABL-0207-01 | 186 | 115 | 96 | 38 | 48 |
| IHuS#ABL-0012-03 | 116 | 112 | 99 | 3 | 14 |
| IHuS#ABL-0208-01 | 466 | 150 | 97 | 68 | 79 |
| IHuS#ABL-0220-01 | 132 | 90 | 81 | 32 | 39 |
| IHuS#ABL-0214-01 | 114 | 103 | 88 | 10 | 23 |
| IHuS#ABL-0215-01 | 88 | 80 | 71 | 9 | 20 |
| IHuS#ABL-0181-01 | 130 | 120 | 101 | 8 | 23 |
| IHuS#ABL-0216-01 | 124 | 110 | 97 | 11 | 22 |
| IHuS#ABL-0217-01 | 177 | 107 | 93 | 40 | 48 |
| IHuS#ABL-0140-01 | 171 | 118 | 106 | 31 | 38 |
| IHuS#ABL-0224-01 | 105 | 104 | 89 | 1 | 16 |
| IHuS#ABL-0182-01 | 103 | 85 | 73 | 18 | 29 |
| IHuS#ABL-0226-01 | 129 | 118 | 99 | 8 | 23 |
| IHuS#ABL-0227-01 | 178 | 124 | 110 | 30 | 38 |
| IHuS#ABL-0205-01 | 139 | 116 | 98 | 16 | 29 |
| IHuS#ABL-0060-03 | 153 | 112 | 90 | 27 | 41 |

Note: all compounds were tested with an N-terminal HIS6-FLAG3 tag

Figure 7

| Sample | Normalized PreAb binding levels (RU at 700) | | | % Reduction PreAb binding compared to Reference A | |
|---|---|---|---|---|---|
| | Reference A | Reference A L11V V89L + Ala | Reference A L11V V89L T110K + Ala | Reference A L11V V89L + Ala | Reference A L11V V89L T110K + Ala |
| IHuS#ABL-0042-02 | 208 | 191 | 187 | 8 | 10 |
| IHuS#ABL-0088-03 | 345 | 207 | 192 | 40 | 44 |
| IHuS#ABL-0137-01 | 220 | 186 | 188 | 15 | 15 |
| IHuS#ABL-0138-01 | 225 | 188 | 185 | 16 | 18 |
| IHuS#ABL-0139-01 | 235 | 194 | 188 | 18 | 20 |
| IHuS#ABL-0141-01 | 218 | 193 | 196 | 12 | 10 |
| IHuS#ABL-0149-01 | 255 | 175 | 175 | 31 | 31 |
| IHuS#ABL-0150-01 | 225 | 181 | 182 | 19 | 19 |
| IHuS#ABL-0151-01 | 303 | 187 | 191 | 38 | 37 |
| IHuS#ABL-0152-01 | 248 | 190 | 190 | 23 | 23 |
| IHuS#ABL-0153-01 | 289 | 174 | 173 | 40 | 40 |
| IHuS#ABL-0154-01 | 199 | 178 | 175 | 11 | 12 |
| IHuS#ABL-0159-01 | 208 | 185 | 178 | 11 | 15 |
| IHuS#ABL-0160-01 | 208 | 190 | 192 | 9 | 7 |
| IHuS#ABL-0161-01 | 217 | 187 | 185 | 14 | 15 |
| IHuS#ABL-0162-01 | 216 | 195 | 192 | 10 | 11 |
| IHuS#ABL-0148-01 | 500 | 196 | 187 | 61 | 63 |
| IHuS#ABL-0163-01 | 465 | 200 | 183 | 57 | 61 |
| IHuS#ABL-0171-01 | 207 | 181 | 179 | 13 | 13 |
| IHuS#ABL-0172-01 | 246 | 186 | 187 | 24 | 24 |
| IHuS#ABL-0218-01 | 265 | 181 | 185 | 32 | 30 |
| IHuS#ABL-0040-03 | 468 | 198 | 186 | 58 | 60 |
| IHuS#ABL-0090-02 | 600 | 201 | 174 | 67 | 71 |
| IHuS#ABL-0173-01 | 385 | 190 | 196 | 51 | 49 |
| IHuS#ABL-0188-01 | 211 | 186 | 182 | 12 | 14 |
| IHuS#ABL-0006-02 | 644 | 270 | 186 | 58 | 71 |
| IHuS#ABL-0189-01 | 225 | 192 | 192 | 15 | 15 |
| IHuS#ABL-0190-01 | 216 | 195 | 193 | 10 | 11 |
| IHuS#ABL-0191-01 | 187 | 169 | 166 | 10 | 11 |
| IHuS#ABL-0192-01 | 218 | 188 | 187 | 14 | 14 |
| IHuS#ABL-0198-01 | 216 | 190 | 178 | 12 | 18 |
| IHuS#ABL-0165-01 | 364 | 187 | 186 | 49 | 49 |
| IHuS#ABL-0199-01 | 374 | 200 | 183 | 47 | 51 |

Figure 7 (continued)

| Sample | Reference A | Reference A L11V V89L + Ala | Reference A L11V V89L T110K + Ala | Reference A L11V V89L + Ala | Reference A L11V V89L T110K + Ala |
|---|---|---|---|---|---|
| IHuS#ABL-0200-01 | 219 | 184 | 183 | 16 | 16 |
| IHuS#ABL-0201-01 | 231 | 187 | 179 | 19 | 22 |
| IHuS#ABL-0202-01 | 298 | 187 | 179 | 37 | 40 |
| IHuS#ABL-0044-02 | 197 | 181 | 178 | 8 | 10 |
| IHuS#ABL-0209-01 | 230 | 187 | 184 | 19 | 20 |
| IHuS#ABL-0210-01 | 221 | 185 | 186 | 16 | 16 |
| IHuS#ABL-0211-01 | 229 | 186 | 185 | 19 | 19 |
| IHuS#ABL-0212-01 | 289 | 188 | 187 | 35 | 35 |
| IHuS#ABL-0213-01 | 216 | 190 | 191 | 12 | 11 |
| IHuS#ABL-0183-01 | 446 | 201 | 181 | 55 | 60 |
| IHuS#ABL-0005-06 | 198 | 175 | 176 | 12 | 12 |
| IHuS#ABL-0219-01 | 220 | 184 | 181 | 16 | 18 |
| IHuS#ABL-0221-01 | 202 | 161 | 162 | 20 | 20 |
| IHuS#ABL-0222-01 | 302 | 188 | 183 | 38 | 39 |
| IHuS#ABL-0223-01 | 419 | 174 | 167 | 58 | 60 |
| IHuS#ABL-0142-01 | 231 | 182 | 178 | 21 | 23 |
| IHuS#ABL-0143-01 | 235 | 187 | 190 | 21 | 19 |
| IHuS#ABL-0144-01 | 314 | 183 | 183 | 42 | 42 |
| IHuS#ABL-0145-01 | 261 | 176 | 173 | 33 | 34 |
| IHuS#ABL-0146-01 | 270 | 178 | 170 | 34 | 37 |
| IHuS#ABL-0147-01 | 317 | 145 | 146 | 54 | 54 |
| IHuS#ABL-0031-04 | 112 | 103 | 114 | 8 | -2 |
| IHuS#ABL-0047-02 | 229 | 174 | 170 | 24 | 26 |
| IHuS#ABL-0155-01 | 299 | 187 | 180 | 37 | 40 |
| IHuS#ABL-0156-01 | 264 | 181 | 178 | 32 | 33 |
| IHuS#ABL-0157-01 | 462 | 184 | 169 | 60 | 63 |
| IHuS#ABL-0158-01 | 430 | 188 | 180 | 56 | 58 |
| IHuS#ABL-0164-01 | 198 | 178 | 176 | 10 | 11 |
| IHuS#ABL-0166-01 | 196 | 175 | 174 | 11 | 12 |
| IHuS#ABL-0167-01 | 349 | 179 | 155 | 49 | 56 |
| IHuS#ABL-0168-01 | 195 | 174 | 175 | 11 | 10 |
| IHuS#ABL-0169-01 | 221 | 180 | 176 | 19 | 20 |
| IHuS#ABL-0170-01 | 390 | 170 | 165 | 57 | 58 |
| IHuS#ABL-0174-01 | 187 | 160 | 153 | 14 | 18 |

Figure 7 (continued)

| Sample | Reference A | Reference A L11V V89L + Ala | Reference A L11V V89L T110K + Ala | Reference A L11V V89L + Ala | Reference A L11V V89L T110K + Ala |
|---|---|---|---|---|---|
| IHuS#ABL-0175-01 | 229 | 183 | 183 | 20 | 20 |
| IHuS#ABL-0176-01 | 226 | 187 | 185 | 17 | 18 |
| IHuS#ABL-0177-01 | 227 | 186 | 183 | 18 | 19 |
| IHuS#ABL-0178-01 | 204 | 193 | 180 | 5 | 12 |
| IHuS#ABL-0179-01 | 219 | 187 | 186 | 14 | 15 |
| IHuS#ABL-0193-01 | 319 | 174 | 174 | 45 | 45 |
| IHuS#ABL-0194-01 | 261 | 171 | 176 | 34 | 33 |
| IHuS#ABL-0195-01 | 497 | 193 | 190 | 61 | 62 |
| IHuS#ABL-0196-01 | 205 | 186 | 187 | 9 | 9 |
| IHuS#ABL-0180-01 | 211 | 182 | 177 | 14 | 16 |
| IHuS#ABL-0197-01 | 198 | 170 | 175 | 14 | 12 |
| IHuS#ABL-0204-01 | 191 | 172 | 166 | 10 | 13 |
| IHuS#ABL-0206-01 | 351 | 198 | 175 | 44 | 50 |
| IHuS#ABL-0207-01 | 279 | 175 | 175 | 37 | 37 |
| IHuS#ABL-0012-03 | 212 | 191 | 189 | 10 | 11 |
| IHuS#ABL-0208-01 | 526 | 217 | 171 | 59 | 68 |
| IHuS#ABL-0220-01 | 213 | 161 | 164 | 25 | 23 |
| IHuS#ABL-0214-01 | 193 | 170 | 174 | 12 | 10 |
| IHuS#ABL-0215-01 | 191 | 171 | 173 | 10 | 9 |
| IHuS#ABL-0181-01 | 198 | 167 | 165 | 16 | 17 |
| IHuS#ABL-0216-01 | 201 | 174 | 173 | 13 | 14 |
| IHuS#ABL-0217-01 | 231 | 168 | 167 | 27 | 28 |
| IHuS#ABL-0140-01 | 231 | 174 | 181 | 24 | 22 |
| IHuS#ABL-0224-01 | 195 | 176 | 175 | 10 | 10 |
| IHuS#ABL-0182-01 | 188 | 153 | 155 | 19 | 18 |
| IHuS#ABL-0226-01 | 212 | 180 | 180 | 15 | 15 |
| IHuS#ABL-0227-01 | 233 | 181 | 177 | 22 | 24 |
| IHuS#ABL-0205-01 | 222 | 177 | 178 | 20 | 20 |
| IHuS#ABL-0060-03 | 227 | 172 | 173 | 24 | 24 |

Figure 10

| Sample | Normalized PreAb binding levels (RU at 700) | | | | % Reduction PreAb binding compared to Reference A | | |
|---|---|---|---|---|---|---|---|
| | Reference C | Reference D | Reference D L11V V89L | Reference D L11V V89L T110K | Reference D | Reference D L11V V89L | Reference D L11V V89L T110K |
| IHuS#ABL-0042-02 | 14 | 5 | 2 | 2 | | | |
| IHuS#ABL-0088-03 | 568 | 237 | 177 | 56 | 58 | 69 | 90 |
| IHuS#ABL-0137-01 | 95 | 62 | 52 | 23 | 35 | 45 | 76 |
| IHuS#ABL-0138-01 | 91 | 7 | 3 | 4 | 93 | 96 | 95 |
| IHuS#ABL-0139-01 | 174 | 51 | 21 | 4 | 71 | 88 | 98 |
| IHuS#ABL-0141-01 | 25 | -8 | -8 | -2 | 100 | 100 | 100 |
| IHuS#ABL-0149-01 | 253 | 36 | 18 | 63 | 86 | 93 | 75 |
| IHuS#ABL-0150-01 | 112 | 27 | 5 | 3 | 76 | 96 | 97 |
| IHuS#ABL-0151-01 | 395 | 49 | 29 | 9 | 88 | 93 | 98 |
| IHuS#ABL-0152-01 | 176 | 17 | 2 | 2 | 90 | 99 | 99 |
| IHuS#ABL-0153-01 | 404 | 222 | 82 | 33 | 45 | 80 | 92 |
| IHuS#ABL-0154-01 | 29 | 20 | 19 | 14 | 30 | 34 | 52 |
| IHuS#ABL-0159-01 | 126 | 51 | 54 | 88 | 60 | 58 | 30 |
| IHuS#ABL-0160-01 | 62 | 40 | 34 | 18 | 35 | 45 | 71 |
| IHuS#ABL-0161-01 | 19 | 17 | 5 | 0 | | | |
| IHuS#ABL-0162-01 | 3 | 21 | 3 | -4 | | | |
| IHuS#ABL-0148-01 | 1013 | 64 | 42 | 10 | 94 | 96 | 99 |

Figure 10 (continued)

| Sample | Reference C | Reference D | Reference D L11V V89L | Reference D L11V V89L T110K | Reference D | Reference D L11V V89L | Reference D L11V V89L T110K |
|---|---|---|---|---|---|---|---|
| IHuS#ABL-0163-01 | 1109 | 154 | 122 | 28 | 86 | 89 | 97 |
| IHuS#ABL-0171-01 | 19 | 8 | 17 | 2 | | | |
| IHuS#ABL-0172-01 | 231 | 72 | 23 | 21 | 69 | 90 | 91 |
| IHuS#ABL-0218-01 | 255 | 57 | 3 | 6 | 78 | 99 | 98 |
| IHuS#ABL-0040-03 | 921 | 117 | 73 | 21 | 87 | 92 | 98 |
| IHuS#ABL-0090-02 | 1231 | 628 | 176 | 52 | 49 | 86 | 96 |
| IHuS#ABL-0173-01 | 736 | 132 | 62 | 50 | 82 | 92 | 93 |
| IHuS#ABL-0188-01 | 83 | 59 | 47 | 52 | 29 | 44 | 37 |
| IHuS#ABL-0006-02 | 1550 | 778 | 457 | 19 | 50 | 71 | 99 |
| IHuS#ABL-0189-01 | 56 | 22 | 16 | -2 | 60 | 72 | 100 |
| IHuS#ABL-0190-01 | 43 | 28 | 15 | 20 | 36 | 65 | 54 |
| IHuS#ABL-0191-01 | 13 | 15 | 12 | 6 | | | |
| IHuS#ABL-0192-01 | 77 | 31 | 8 | -16 | 60 | 89 | 100 |
| IHuS#ABL-0198-01 | 74 | 23 | 18 | 13 | 69 | 76 | 83 |
| IHuS#ABL-0165-01 | 668 | 73 | 26 | -4 | 89 | 96 | 100 |
| IHuS#ABL-0199-01 | 754 | 135 | 125 | 1 | 82 | 83 | 100 |
| IHuS#ABL-0200-01 | 98 | 27 | 15 | 1 | 72 | 84 | 99 |
| IHuS#ABL-0201-01 | 145 | 18 | 27 | -5 | 87 | 81 | 100 |
| IHuS#ABL-0202-01 | 524 | 49 | 99 | 14 | 91 | 81 | 97 |
| IHuS#ABL-0044-02 | 5 | 8 | 4 | 2 | | | |

Figure 10 (continued)

| Sample | Reference C | Reference D | Reference D L11V V89L | Reference D L11V V89L T110K | Reference D | Reference D L11V V89L | Reference D L11V V89L T110K |
|---|---|---|---|---|---|---|---|
| IHuS#ABL-0209-01 | 166 | 40 | 55 | 20 | 76 | 67 | 88 |
| IHuS#ABL-0210-01 | 59 | 24 | 21 | 4 | 60 | 65 | 93 |
| IHuS#ABL-0211-01 | 153 | 57 | 11 | -1 | 63 | 93 | 100 |
| IHuS#ABL-0212-01 | 358 | 127 | 92 | 59 | 65 | 74 | 83 |
| IHuS#ABL-0213-01 | 69 | 43 | 53 | 29 | 37 | 22 | 58 |
| IHuS#ABL-0183-01 | 898 | 543 | 141 | 10 | 40 | 84 | 99 |
| IHuS#ABL-0005-06 | 44 | 52 | 29 | 3 | -18 | 33 | 94 |
| IHuS#ABL-0219-01 | 234 | 168 | 158 | 107 | 28 | 33 | 54 |
| IHuS#ABL-0221-01 | 160 | 92 | 53 | 20 | 43 | 67 | 87 |
| IHuS#ABL-0222-01 | 587 | 25 | 11 | 15 | 96 | 98 | 97 |
| IHuS#ABL-0223-01 | 850 | 332 | 63 | -1 | 61 | 93 | 100 |
| IHuS#ABL-0142-01 | 96 | 7 | -1 | -19 | 93 | 100 | 100 |
| IHuS#ABL-0143-01 | 94 | 26 | 17 | 7 | 72 | 82 | 93 |
| IHuS#ABL-0144-01 | 313 | 67 | 17 | -5 | 79 | 94 | 100 |
| IHuS#ABL-0145-01 | 291 | 19 | -2 | -4 | 94 | 100 | 100 |
| IHuS#ABL-0146-01 | 242 | 59 | 13 | -12 | 76 | 94 | 100 |
| IHuS#ABL-0147-01 | 616 | 188 | 71 | 53 | 69 | 89 | 91 |
| IHuS#ABL-0031-04 | 18 | -45 | 0 | 47 | | | |
| IHuS#ABL-0047-02 | 193 | 42 | 30 | 20 | 78 | 85 | 90 |
| IHuS#ABL-0155-01 | 302 | 37 | 43 | 19 | 88 | 86 | 94 |

Figure 10 (continued)

| Sample | Reference C | Reference D | Reference D L11V V89L | Reference D L11V V89L T110K | Reference D | Reference D L11V V89L | Reference D L11V V89L T110K |
|---|---|---|---|---|---|---|---|
| IHuS#ABL-0156-01 | 261 | 56 | 28 | 10 | 79 | 89 | 96 |
| IHuS#ABL-0157-01 | 774 | 292 | 126 | 60 | 62 | 84 | 92 |
| IHuS#ABL-0158-01 | 842 | 106 | 53 | 23 | 87 | 94 | 97 |
| IHuS#ABL-0164-01 | 1 | 5 | 0 | -3 | | | |
| IHuS#ABL-0166-01 | 4 | 37 | 39 | 12 | 44 | 70 | 100 |
| IHuS#ABL-0167-01 | 813 | 458 | 242 | 3 | | | |
| IHuS#ABL-0168-01 | 10 | 13 | 8 | 8 | | | |
| IHuS#ABL-0169-01 | 105 | 2 | 7 | -6 | 98 | 93 | 100 |
| IHuS#ABL-0170-01 | 673 | 58 | 36 | 15 | 91 | 95 | 98 |
| ABL-0041-01_C | 275 | 107 | 49 | 42 | 61 | 82 | 85 |
| ABL-0053-01_C | 819 | 194 | 29 | -6 | 76 | 97 | 100 |
| ABL-0054-01_C | 1050 | 413 | 109 | 11 | 61 | 90 | 99 |
| ABL-0045-01_C | 1220 | 728 | 430 | 7 | 40 | 65 | 99 |
| ABL-0062-01_C | 1094 | 685 | 268 | 25 | 37 | 75 | 98 |
| ABL-0039-01_C | 1250 | 756 | 453 | 12 | 40 | 64 | 99 |
| HSI#26062008Ind11 | 2092 | 671 | 800 | 255 | 68 | 62 | 88 |
| IHuS#29Sep2011Ind14F | 573 | 246 | 197 | 5 | 57 | 66 | 99 |
| IHuS#29Sep2011Ind39F | 556 | 421 | 228 | 31 | 24 | 59 | 94 |
| IHuS#29Sep2011Ind43M | 222 | 46 | 26 | 25 | 79 | 88 | 89 |
| IHuS#29Sep2011Ind44F | 997 | 374 | 299 | -7 | 62 | 70 | 100 |
| IHuS#P6012314 A20 | 491 | 161 | 64 | 38 | 67 | 87 | 92 |

Figure 10 (continued)

| Sample | Reference C | Reference D | Reference D L11V V89L | Reference D L11V V89L T110K | Reference D | Reference D L11V V89L | Reference D L11V V89L T110K |
|---|---|---|---|---|---|---|---|
| IHuS#P7012314 A06 | 747 | 229 | 131 | 32 | 69 | 82 | 96 |
| IHuS#P7012314 A12 | 661 | 201 | 50 | 32 | 70 | 92 | 95 |
| IHuS#ABL-0195-01 | 784 | 535 | 67 | -2 | 32 | 91 | 100 |
| IHuS#ABL-0208-01 | 967 | 360 | 205 | 12 | 63 | 79 | 99 |
| IHuS#ABL-0184-01 | 620 | 290 | 104 | 55 | 53 | 83 | 91 |
| NB130259-004 | 305 | 70 | 31 | 0 | 77 | 90 | 100 |
| IHuS#04APR2012Ind05m | 485 | 387 | 101 | 80 | 20 | 79 | 84 |
| IHuS#04APR2012Ind06m | 700 | 659 | 117 | 134 | 6 | 83 | 81 |
| IHuS#04APR2012Ind07m | 550 | 484 | 74 | 75 | 12 | 87 | 86 |
| IHuS#04APR2012Ind09m | 700 | 635 | 89 | 97 | 9 | 87 | 86 |
| IHuS#04APR2012Ind10m | 732 | 704 | 85 | 72 | 4 | 88 | 90 |
| IHuS#04APR2012Ind03F | 1013 | 508 | 219 | 25 | 50 | 78 | 97 |
| IHuS#04APR2012Ind04F | 543 | -228 | -459 | -488 | 100 | 100 | 100 |
| IHuS#04APR2012Ind15F | 699 | 672 | 225 | 1 | 4 | 68 | 100 |
| IHuS#04APR2012Ind27F | 1100 | 1170 | 264 | 487 | -6 | 76 | 56 |
| IHuS#04APR2012Ind29F | 830 | 792 | 105 | 18 | 5 | 87 | 98 |
| IHuS#04APR2012Ind31F | 674 | 534 | 229 | 4 | 21 | 66 | 99 |
| IHuS#04APR2012Ind40F | 850 | 537 | 75 | 41 | 37 | 91 | 95 |

SEQUENCE LISTING

```
<160> NUMBER OF SEQ ID NOS: 115

<210> SEQ ID NO 1
<211> LENGTH: 121
<212> TYPE: PRT
<213> ORGANISM: Artificial Sequence
<220> FEATURE:
<223> OTHER INFORMATION: CDR sequence

<400> SEQUENCE: 1

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Gly
```

```
                    20                  25                  30

Glu Met Ala Trp Val Arg Gln Ala Pro Gly Lys Gly Leu Glu Trp Val
            35                  40                  45

Ser Ser Ile Ser Ser Ser Gly Ala Thr Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Thr Val Ser Ser
        115                 120

<210> SEQ ID NO 2
<211> LENGTH: 119
<212> TYPE: PRT
<213> ORGANISM: Artificial Sequence
<220> FEATURE:
<223> OTHER INFORMATION: CDR sequence

<400> SEQUENCE: 2

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
            35                  40                  45

Ser Val Ile His Gln Ser Gly Thr Pro Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Phe Pro Ser Thr His Gly Lys Phe Asp Tyr Trp Gly Gln Gly
            100                 105                 110

Thr Leu Val Thr Val Ser Ser
        115

<210> SEQ ID NO 3
<211> LENGTH: 119
<212> TYPE: PRT
<213> ORGANISM: Artificial Sequence
<220> FEATURE:
<223> OTHER INFORMATION: CDR sequence

<400> SEQUENCE: 3

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
            35                  40                  45

Ser Val Ile His Gln Ser Gly Thr Pro Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80
```

```
Leu Gln Met Asn Ser Leu Arg Ala Glu Asp Thr Ala Val Tyr Tyr Cys
                85                  90                  95
Ala Lys Phe Pro Ser Ser Arg Met Lys Phe Asp Tyr Trp Gly Gln Gly
            100                 105                 110
Thr Leu Val Thr Val Ser Ser
        115

<210> SEQ ID NO 4
<211> LENGTH: 120
<212> TYPE: PRT
<213> ORGANISM: Artificial Sequence
<220> FEATURE:
<223> OTHER INFORMATION: CDR sequence

<400> SEQUENCE: 4

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Asp Thr Ser
            20                  25                  30
Ser Met Leu Trp Val Arg Gln Ala Pro Gly Lys Gly Leu Glu Trp Val
        35                  40                  45
Ser Val Ile His Gln Ser Gly Thr Pro Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Phe Pro Ser Ser Arg Met Lys Phe Asp Tyr Trp Gly Gln Gly
            100                 105                 110
Thr Leu Val Thr Val Ser Ser Ala
        115                 120

<210> SEQ ID NO 5
<211> LENGTH: 5
<212> TYPE: PRT
<213> ORGANISM: Artificial Sequence
<220> FEATURE:
<223> OTHER INFORMATION: CDR sequence

<400> SEQUENCE: 5

Thr Gly Glu Met Ala
1               5

<210> SEQ ID NO 6
<211> LENGTH: 17
<212> TYPE: PRT
<213> ORGANISM: Artificial Sequence
<220> FEATURE:
<223> OTHER INFORMATION: CDR sequence

<400> SEQUENCE: 6

Ser Ile Ser Ser Ser Gly Ala Thr Thr Tyr Tyr Ala Asp Ser Val Lys
1               5                   10                  15
Gly

<210> SEQ ID NO 7
<211> LENGTH: 12
<212> TYPE: PRT
<213> ORGANISM: Artificial Sequence
<220> FEATURE:
<223> OTHER INFORMATION: CDR sequence
```

-continued

```
<400> SEQUENCE: 7

Pro Arg His Pro Gln Gly Gly Val Thr Phe Asp Tyr
1               5                   10

<210> SEQ ID NO 8
<211> LENGTH: 10
<212> TYPE: PRT
<213> ORGANISM: Artificial Sequence
<220> FEATURE:
<223> OTHER INFORMATION: CDR sequence

<400> SEQUENCE: 8

Gly Phe Thr Phe Ser Thr Gly Glu Met Ala
1               5                   10

<210> SEQ ID NO 9
<211> LENGTH: 10
<212> TYPE: PRT
<213> ORGANISM: Artificial Sequence
<220> FEATURE:
<223> OTHER INFORMATION: CDR sequence

<400> SEQUENCE: 9

Ser Ile Ser Ser Ser Gly Ala Thr Thr Tyr
1               5                   10

<210> SEQ ID NO 10
<211> LENGTH: 5
<212> TYPE: PRT
<213> ORGANISM: Artificial Sequence
<220> FEATURE:
<223> OTHER INFORMATION: CDR sequence

<400> SEQUENCE: 10

Thr Ser Ser Met Leu
1               5

<210> SEQ ID NO 11
<211> LENGTH: 17
<212> TYPE: PRT
<213> ORGANISM: Artificial Sequence
<220> FEATURE:
<223> OTHER INFORMATION: CDR sequence

<400> SEQUENCE: 11

Val Ile His Gln Ser Gly Thr Pro Thr Tyr Tyr Ala Asp Ser Val Lys
1               5                   10                  15

Gly

<210> SEQ ID NO 12
<211> LENGTH: 10
<212> TYPE: PRT
<213> ORGANISM: Artificial Sequence
<220> FEATURE:
<223> OTHER INFORMATION: CDR sequence

<400> SEQUENCE: 12

Phe Pro Ser Thr His Gly Lys Phe Asp Tyr
1               5                   10

<210> SEQ ID NO 13
<211> LENGTH: 10
<212> TYPE: PRT
<213> ORGANISM: Artificial Sequence
<220> FEATURE:
<223> OTHER INFORMATION: CDR sequence
```

```
<400> SEQUENCE: 13

Gly Phe Thr Phe Asp Thr Ser Ser Met Leu
1               5                   10

<210> SEQ ID NO 14
<211> LENGTH: 10
<212> TYPE: PRT
<213> ORGANISM: Artificial Sequence
<220> FEATURE:
<223> OTHER INFORMATION: CDR sequence

<400> SEQUENCE: 14

Val Ile His Gln Ser Gly Thr Pro Thr Tyr
1               5                   10

<210> SEQ ID NO 15
<211> LENGTH: 10
<212> TYPE: PRT
<213> ORGANISM: Artificial Sequence
<220> FEATURE:
<223> OTHER INFORMATION: CDR sequence

<400> SEQUENCE: 15

Phe Pro Ser Ser Arg Met Lys Phe Asp Tyr
1               5                   10

<210> SEQ ID NO 16
<211> LENGTH: 121
<212> TYPE: PRT
<213> ORGANISM: Artificial Sequence
<220> FEATURE:
<223> OTHER INFORMATION: CDR sequence

<400> SEQUENCE: 16

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Lys Val Ser Ser
        115                 120

<210> SEQ ID NO 17
<211> LENGTH: 121
<212> TYPE: PRT
<213> ORGANISM: Artificial Sequence
<220> FEATURE:
<223> OTHER INFORMATION: CDR sequence

<400> SEQUENCE: 17

Glu Val Gln Leu Leu Glu Ser Gly Gly Gly Leu Val Gln Pro Gly Gly
1               5                   10                  15
```

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Gln Val Ser Ser
        115                 120

<210> SEQ ID NO 18
<211> LENGTH: 121
<212> TYPE: PRT
<213> ORGANISM: Artificial Sequence
<220> FEATURE:
<223> OTHER INFORMATION: CDR sequence

<400> SEQUENCE: 18

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Thr Val Lys Ser
        115                 120

<210> SEQ ID NO 19
<211> LENGTH: 121
<212> TYPE: PRT
<213> ORGANISM: Artificial Sequence
<220> FEATURE:
<223> OTHER INFORMATION: CDR sequence

<400> SEQUENCE: 19

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Leu Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Thr Val Gln Ser
        115                 120

<210> SEQ ID NO 20
<211> LENGTH: 121
<212> TYPE: PRT
<213> ORGANISM: Artificial Sequence
<220> FEATURE:
<223> OTHER INFORMATION: CDR sequence

<400> SEQUENCE: 20

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Thr Val Lys Ser
        115                 120

<210> SEQ ID NO 21
<211> LENGTH: 121
<212> TYPE: PRT
<213> ORGANISM: Artificial Sequence
<220> FEATURE:
<223> OTHER INFORMATION: CDR sequence

<400> SEQUENCE: 21

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Thr Val Gln Ser
        115                 120
```

```
<210> SEQ ID NO 22
<211> LENGTH: 121
<212> TYPE: PRT
<213> ORGANISM: Artificial Sequence
<220> FEATURE:
<223> OTHER INFORMATION: CDR sequence

<400> SEQUENCE: 22

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Thr Val Ser Ser
        115                 120

<210> SEQ ID NO 23
<211> LENGTH: 121
<212> TYPE: PRT
<213> ORGANISM: Artificial Sequence
<220> FEATURE:
<223> OTHER INFORMATION: CDR sequence

<400> SEQUENCE: 23

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Thr Val Ser Ser
        115                 120

<210> SEQ ID NO 24
<211> LENGTH: 121
<212> TYPE: PRT
<213> ORGANISM: Artificial Sequence
<220> FEATURE:
<223> OTHER INFORMATION: CDR sequence

<400> SEQUENCE: 24

Glu Val Gln Leu Leu Glu Ser Gly Gly Gly Val Val Gln Pro Gly Gly
1               5                   10                  15
```

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
            35                  40                  45

Ser Ser Ile Ser Ser Ser Gly Ala Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Lys Val Ser Ser
            115                 120

<210> SEQ ID NO 25
<211> LENGTH: 121
<212> TYPE: PRT
<213> ORGANISM: Artificial Sequence
<220> FEATURE:
<223> OTHER INFORMATION: CDR sequence

<400> SEQUENCE: 25

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
            35                  40                  45

Ser Ser Ile Ser Ser Ser Gly Ala Thr Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Gln Val Ser Ser
            115                 120

<210> SEQ ID NO 26
<211> LENGTH: 121
<212> TYPE: PRT
<213> ORGANISM: Artificial Sequence
<220> FEATURE:
<223> OTHER INFORMATION: CDR sequence

<400> SEQUENCE: 26

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
            35                  40                  45

Ser Ser Ile Ser Ser Ser Gly Ala Thr Thr Tyr Tyr Ala Asp Ser Val
        50                  55                  60

Lys Gly Arg Phe Thr Ile Ser Arg Asp Asn Ser Lys Asn Thr Leu Tyr

```
                65                  70                  75                  80
Leu Gln Met Asn Ser Leu Arg Ala Glu Asp Thr Ala Val Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Lys Val Ser Ser
            115                 120

<210> SEQ ID NO 27
<211> LENGTH: 121
<212> TYPE: PRT
<213> ORGANISM: Artificial Sequence
<220> FEATURE:
<223> OTHER INFORMATION: CDR sequence

<400> SEQUENCE: 27

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Gln Val Ser Ser
            115                 120

<210> SEQ ID NO 28
<211> LENGTH: 121
<212> TYPE: PRT
<213> ORGANISM: Artificial Sequence
<220> FEATURE:
<223> OTHER INFORMATION: CDR sequence

<400> SEQUENCE: 28

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Thr Val Lys Ser
            115                 120
```

```
<210> SEQ ID NO 29
<211> LENGTH: 121
<212> TYPE: PRT
<213> ORGANISM: Artificial Sequence
<220> FEATURE:
<223> OTHER INFORMATION: CDR sequence

<400> SEQUENCE: 29

Glu Val Gln Leu Leu Glu Ser Gly Gly Val Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Thr Val Gln Ser
        115                 120

<210> SEQ ID NO 30
<211> LENGTH: 122
<212> TYPE: PRT
<213> ORGANISM: Artificial Sequence
<220> FEATURE:
<223> OTHER INFORMATION: CDR sequence

<400> SEQUENCE: 30

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Lys Val Ser Ser Ala
        115                 120

<210> SEQ ID NO 31
<211> LENGTH: 122
<212> TYPE: PRT
<213> ORGANISM: Artificial Sequence
<220> FEATURE:
<223> OTHER INFORMATION: CDR sequence

<400> SEQUENCE: 31

Glu Val Gln Leu Leu Glu Ser Gly Gly Gly Leu Val Gln Pro Gly Gly
```

```
                1               5                  10                 15
            Ser Leu Arg Leu Ser Cys Ala Ala Ser Gly Phe Thr Phe Ser Thr Gly
                            20                  25                  30

Glu Met Ala Trp Val Arg Gln Ala Pro Gly Lys Gly Leu Glu Trp Val
                        35                  40                  45

Ser Ser Ile Ser Ser Ser Gly Ala Thr Thr Tyr Tyr Ala Asp Ser Val
                    50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Leu Tyr Tyr Cys
                            85                  90                  95

Ala Lys Pro Arg His Pro Gln Gly Gly Val Thr Phe Asp Tyr Trp Gly
                            100                 105                 110

Gln Gly Thr Leu Val Gln Val Ser Ala
                            115                 120

<210> SEQ ID NO 32
<211> LENGTH: 122
<212> TYPE: PRT
<213> ORGANISM: Artificial Sequence
<220> FEATURE:
<223> OTHER INFORMATION: CDR sequence

<400> SEQUENCE: 32

Glu Val Gln Leu Leu Glu Ser Gly Gly Gly Leu Val Gln Pro Gly Gly
             1               5                  10                 15

Ser Leu Arg Leu Ser Cys Ala Ala Ser Gly Phe Thr Phe Ser Thr Gly
                            20                  25                  30

Glu Met Ala Trp Val Arg Gln Ala Pro Gly Lys Gly Leu Glu Trp Val
                        35                  40                  45

Ser Ser Ile Ser Ser Ser Gly Ala Thr Thr Tyr Tyr Ala Asp Ser Val
                    50                  55                  60

Lys Gly Arg Phe Thr Ile Ser Arg Asp Asn Ser Lys Asn Thr Leu Tyr
             65                  70                  75                  80

Leu Gln Met Asn Ser Leu Arg Ala Glu Asp Thr Ala Leu Tyr Tyr Cys
                            85                  90                  95

Ala Lys Pro Arg His Pro Gln Gly Gly Val Thr Phe Asp Tyr Trp Gly
                            100                 105                 110

Gln Gly Thr Leu Val Thr Val Lys Ser Ala
                            115                 120

<210> SEQ ID NO 33
<211> LENGTH: 122
<212> TYPE: PRT
<213> ORGANISM: Artificial Sequence
<220> FEATURE:
<223> OTHER INFORMATION: CDR sequence

<400> SEQUENCE: 33

Glu Val Gln Leu Leu Glu Ser Gly Gly Gly Leu Val Gln Pro Gly Gly
             1               5                  10                 15

Ser Leu Arg Leu Ser Cys Ala Ala Ser Gly Phe Thr Phe Ser Thr Gly
                            20                  25                  30

Glu Met Ala Trp Val Arg Gln Ala Pro Gly Lys Gly Leu Glu Trp Val
                        35                  40                  45

Ser Ser Ile Ser Ser Ser Gly Ala Thr Thr Tyr Tyr Ala Asp Ser Val
                    50                  55                  60
```

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Lys Pro Arg His Pro Gln Gly Gly Val Thr Phe Asp Tyr Trp Gly
            100                 105                 110

Gln Gly Thr Leu Val Thr Val Gln Ser Ala
            115                 120

<210> SEQ ID NO 34
<211> LENGTH: 122
<212> TYPE: PRT
<213> ORGANISM: Artificial Sequence
<220> FEATURE:
<223> OTHER INFORMATION: CDR sequence

<400> SEQUENCE: 34

Glu Val Gln Leu Leu Glu Ser Gly Gly Gly Val Val Gln Pro Gly Gly
  1               5                  10                  15

Ser Leu Arg Leu Ser Cys Ala Ala Ser Gly Phe Thr Phe Ser Thr Gly
                 20                  25                  30

Glu Met Ala Trp Val Arg Gln Ala Pro Gly Lys Gly Leu Glu Trp Val
             35                  40                  45

Ser Ser Ile Ser Ser Ser Gly Ala Thr Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Lys Pro Arg His Pro Gln Gly Gly Val Thr Phe Asp Tyr Trp Gly
            100                 105                 110

Gln Gly Thr Leu Val Thr Val Lys Ser Ala
            115                 120

<210> SEQ ID NO 35
<211> LENGTH: 122
<212> TYPE: PRT
<213> ORGANISM: Artificial Sequence
<220> FEATURE:
<223> OTHER INFORMATION: CDR sequence

<400> SEQUENCE: 35

Glu Val Gln Leu Leu Glu Ser Gly Gly Gly Val Val Gln Pro Gly Gly
  1               5                  10                  15

Ser Leu Arg Leu Ser Cys Ala Ala Ser Gly Phe Thr Phe Ser Thr Gly
                 20                  25                  30

Glu Met Ala Trp Val Arg Gln Ala Pro Gly Lys Gly Leu Glu Trp Val
             35                  40                  45

Ser Ser Ile Ser Ser Ser Gly Ala Thr Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Lys Pro Arg His Pro Gln Gly Gly Val Thr Phe Asp Tyr Trp Gly
            100                 105                 110

Gln Gly Thr Leu Val Thr Val Gln Ser Ala
            115                 120
```

<210> SEQ ID NO 36
<211> LENGTH: 122
<212> TYPE: PRT
<213> ORGANISM: Artificial Sequence
<220> FEATURE:
<223> OTHER INFORMATION: CDR sequence

<400> SEQUENCE: 36

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Thr Val Ser Ser Ala
        115                 120

<210> SEQ ID NO 37
<211> LENGTH: 122
<212> TYPE: PRT
<213> ORGANISM: Artificial Sequence
<220> FEATURE:
<223> OTHER INFORMATION: CDR sequence

<400> SEQUENCE: 37

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Thr Val Ser Ser Ala
        115                 120

<210> SEQ ID NO 38
<211> LENGTH: 122
<212> TYPE: PRT
<213> ORGANISM: Artificial Sequence
<220> FEATURE:
<223> OTHER INFORMATION: CDR sequence

<400> SEQUENCE: 38

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Lys Val Ser Ser Ala
            115                 120

<210> SEQ ID NO 39
<211> LENGTH: 122
<212> TYPE: PRT
<213> ORGANISM: Artificial Sequence
<220> FEATURE:
<223> OTHER INFORMATION: CDR sequence

<400> SEQUENCE: 39

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Pro Arg His Pro Gln Gly Gly Val Thr Phe Asp Tyr Trp Gly
            100                 105                 110

Gln Gly Thr Leu Val Gln Val Ser Ser Ala
            115                 120

<210> SEQ ID NO 40
<211> LENGTH: 122
<212> TYPE: PRT
<213> ORGANISM: Artificial Sequence
<220> FEATURE:
<223> OTHER INFORMATION: CDR sequence

<400> SEQUENCE: 40

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
50                  55                  60

```
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Arg His Pro Gln Gly Gly Val Thr Phe Asp Tyr Trp Gly
            100                 105                 110

Gln Gly Thr Leu Val Lys Val Ser Ser Ala
        115                 120
```

<210> SEQ ID NO 41
<211> LENGTH: 122
<212> TYPE: PRT
<213> ORGANISM: Artificial Sequence
<220> FEATURE:
<223> OTHER INFORMATION: CDR sequence

<400> SEQUENCE: 41

```
Glu Val Gln Leu Leu Glu Ser Gly Gly Gly Val Val Gln Pro Gly Gly
 1               5                  10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Arg His Pro Gln Gly Gly Val Thr Phe Asp Tyr Trp Gly
            100                 105                 110

Gln Gly Thr Leu Val Gln Val Ser Ser Ala
        115                 120
```

<210> SEQ ID NO 42
<211> LENGTH: 122
<212> TYPE: PRT
<213> ORGANISM: Artificial Sequence
<220> FEATURE:
<223> OTHER INFORMATION: CDR sequence

<400> SEQUENCE: 42

```
Glu Val Gln Leu Leu Glu Ser Gly Gly Gly Val Val Gln Pro Gly Gly
 1               5                  10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Arg His Pro Gln Gly Gly Val Thr Phe Asp Tyr Trp Gly
            100                 105                 110

Gln Gly Thr Leu Val Thr Val Lys Ser Ala
```

<210> SEQ ID NO 43
<211> LENGTH: 122
<212> TYPE: PRT
<213> ORGANISM: Artificial Sequence
<220> FEATURE:
<223> OTHER INFORMATION: CDR sequence

<400> SEQUENCE: 43

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Ser Thr Gly
            20                  25                  30

Glu Met Ala Trp Val Arg Gln Ala Pro Gly Lys Gly Leu Glu Trp Val
        35                  40                  45

Ser Ser Ile Ser Ser Gly Ala Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Arg His Pro Gln Gly Gly Val Thr Phe Asp Tyr Trp Gly
                100                 105                 110

Gln Gly Thr Leu Val Thr Val Gln Ser Ala
            115                 120

<210> SEQ ID NO 44
<211> LENGTH: 119
<212> TYPE: PRT
<213> ORGANISM: Artificial Sequence
<220> FEATURE:
<223> OTHER INFORMATION: CDR sequence

<400> SEQUENCE: 44

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Thr His Gly Lys Phe Asp Tyr Trp Gly Gln Gly
                100                 105                 110

Thr Leu Val Lys Val Ser Ser
            115

<210> SEQ ID NO 45
<211> LENGTH: 119
<212> TYPE: PRT
<213> ORGANISM: Artificial Sequence
<220> FEATURE:
<223> OTHER INFORMATION: CDR sequence

<400> SEQUENCE: 45

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Thr His Gly Lys Phe Asp Tyr Trp Gly Gln Gly
            100                 105                 110

Thr Leu Val Gln Val Ser Ser
        115

<210> SEQ ID NO 46
<211> LENGTH: 119
<212> TYPE: PRT
<213> ORGANISM: Artificial Sequence
<220> FEATURE:
<223> OTHER INFORMATION: CDR sequence

<400> SEQUENCE: 46

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Thr His Gly Lys Phe Asp Tyr Trp Gly Gln Gly
            100                 105                 110

Thr Leu Val Thr Val Ser Ser
        115

<210> SEQ ID NO 47
<211> LENGTH: 119
<212> TYPE: PRT
<213> ORGANISM: Artificial Sequence
<220> FEATURE:
<223> OTHER INFORMATION: CDR sequence

<400> SEQUENCE: 47

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val

```
                   50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Lys Phe Pro Ser Thr His Gly Lys Phe Asp Tyr Trp Gly Gln Gly
            100                 105                 110

Thr Leu Val Thr Val Gln Ser
        115

<210> SEQ ID NO 48
<211> LENGTH: 119
<212> TYPE: PRT
<213> ORGANISM: Artificial Sequence
<220> FEATURE:
<223> OTHER INFORMATION: CDR sequence

<400> SEQUENCE: 48

Glu Val Gln Leu Leu Glu Ser Gly Gly Gly Val Val Gln Pro Gly Gly
 1               5                  10                  15

Ser Leu Arg Leu Ser Cys Ala Ala Ser Gly Phe Thr Phe Asp Thr Ser
                20                  25                  30

Ser Met Leu Trp Val Arg Gln Ala Pro Gly Lys Gly Leu Glu Trp Val
            35                  40                  45

Ser Val Ile His Gln Ser Gly Thr Pro Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Lys Phe Pro Ser Thr His Gly Lys Phe Asp Tyr Trp Gly Gln Gly
            100                 105                 110

Thr Leu Val Thr Val Lys Ser
        115

<210> SEQ ID NO 49
<211> LENGTH: 119
<212> TYPE: PRT
<213> ORGANISM: Artificial Sequence
<220> FEATURE:
<223> OTHER INFORMATION: CDR sequence

<400> SEQUENCE: 49

Glu Val Gln Leu Leu Glu Ser Gly Gly Gly Val Val Gln Pro Gly Gly
 1               5                  10                  15

Ser Leu Arg Leu Ser Cys Ala Ala Ser Gly Phe Thr Phe Asp Thr Ser
                20                  25                  30

Ser Met Leu Trp Val Arg Gln Ala Pro Gly Lys Gly Leu Glu Trp Val
            35                  40                  45

Ser Val Ile His Gln Ser Gly Thr Pro Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Lys Phe Pro Ser Thr His Gly Lys Phe Asp Tyr Trp Gly Gln Gly
            100                 105                 110
```

Thr Leu Val Thr Val Gln Ser
        115

<210> SEQ ID NO 50
<211> LENGTH: 119
<212> TYPE: PRT
<213> ORGANISM: Artificial Sequence
<220> FEATURE:
<223> OTHER INFORMATION: CDR sequence

<400> SEQUENCE: 50

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Lys Phe Pro Ser Thr His Gly Lys Phe Asp Tyr Trp Gly Gln Gly
            100                 105                 110

Thr Leu Val Thr Val Ser Ser
        115

<210> SEQ ID NO 51
<211> LENGTH: 119
<212> TYPE: PRT
<213> ORGANISM: Artificial Sequence
<220> FEATURE:
<223> OTHER INFORMATION: CDR sequence

<400> SEQUENCE: 51

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Thr His Gly Lys Phe Asp Tyr Trp Gly Gln Gly
            100                 105                 110

Thr Leu Val Thr Val Ser Ser
        115

<210> SEQ ID NO 52
<211> LENGTH: 119
<212> TYPE: PRT
<213> ORGANISM: Artificial Sequence
<220> FEATURE:
<223> OTHER INFORMATION: CDR sequence

<400> SEQUENCE: 52

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Thr His Gly Lys Phe Asp Tyr Trp Gly Gln Gly
            100                 105                 110

Thr Leu Val Lys Val Ser Ser
        115

<210> SEQ ID NO 53
<211> LENGTH: 119
<212> TYPE: PRT
<213> ORGANISM: Artificial Sequence
<220> FEATURE:
<223> OTHER INFORMATION: CDR sequence

<400> SEQUENCE: 53

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Thr His Gly Lys Phe Asp Tyr Trp Gly Gln Gly
            100                 105                 110

Thr Leu Val Gln Val Ser Ser
        115

<210> SEQ ID NO 54
<211> LENGTH: 119
<212> TYPE: PRT
<213> ORGANISM: Artificial Sequence
<220> FEATURE:
<223> OTHER INFORMATION: CDR sequence

<400> SEQUENCE: 54

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

```
Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Pro Ser Thr His Gly Lys Phe Asp Tyr Trp Gly Gln Gly
                100                 105                 110

Thr Leu Val Lys Val Ser Ser
            115
```

<210> SEQ ID NO 55
<211> LENGTH: 119
<212> TYPE: PRT
<213> ORGANISM: Artificial Sequence
<220> FEATURE:
<223> OTHER INFORMATION: CDR sequence

<400> SEQUENCE: 55

```
Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
                20                  25                  30

Ser Met Leu Trp Val Arg Gln Ala Pro Gly Lys Gly Leu Glu Trp Val
            35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Pro Ser Thr His Gly Lys Phe Asp Tyr Trp Gly Gln Gly
                100                 105                 110

Thr Leu Val Gln Val Ser Ser
            115
```

<210> SEQ ID NO 56
<211> LENGTH: 119
<212> TYPE: PRT
<213> ORGANISM: Artificial Sequence
<220> FEATURE:
<223> OTHER INFORMATION: CDR sequence

<400> SEQUENCE: 56

```
Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
                20                  25                  30

Ser Met Leu Trp Val Arg Gln Ala Pro Gly Lys Gly Leu Glu Trp Val
            35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Pro Ser Thr His Gly Lys Phe Asp Tyr Trp Gly Gln Gly
                100                 105                 110
```

Thr Leu Val Thr Val Lys Ser
        115

<210> SEQ ID NO 57
<211> LENGTH: 119
<212> TYPE: PRT
<213> ORGANISM: Artificial Sequence
<220> FEATURE:
<223> OTHER INFORMATION: CDR sequence

<400> SEQUENCE: 57

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Pro Ser Thr His Gly Lys Phe Asp Tyr Trp Gly Gln Gly
            100                 105                 110

Thr Leu Val Thr Val Gln Ser
        115

<210> SEQ ID NO 58
<211> LENGTH: 120
<212> TYPE: PRT
<213> ORGANISM: Artificial Sequence
<220> FEATURE:
<223> OTHER INFORMATION: CDR sequence

<400> SEQUENCE: 58

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Thr His Gly Lys Phe Asp Tyr Trp Gly Gln Gly
            100                 105                 110

Thr Leu Val Lys Val Ser Ser Ala
        115                 120

<210> SEQ ID NO 59
<211> LENGTH: 120
<212> TYPE: PRT
<213> ORGANISM: Artificial Sequence
<220> FEATURE:
<223> OTHER INFORMATION: CDR sequence

<400> SEQUENCE: 59

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Thr His Gly Lys Phe Asp Tyr Trp Gly Gln Gly
            100                 105                 110

Thr Leu Val Gln Val Ser Ser Ala
            115                 120

<210> SEQ ID NO 60
<211> LENGTH: 120
<212> TYPE: PRT
<213> ORGANISM: Artificial Sequence
<220> FEATURE:
<223> OTHER INFORMATION: CDR sequence

<400> SEQUENCE: 60

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Thr His Gly Lys Phe Asp Tyr Trp Gly Gln Gly
            100                 105                 110

Thr Leu Val Gln Val Lys Ser Ala
            115                 120

<210> SEQ ID NO 61
<211> LENGTH: 120
<212> TYPE: PRT
<213> ORGANISM: Artificial Sequence
<220> FEATURE:
<223> OTHER INFORMATION: CDR sequence

<400> SEQUENCE: 61

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Lys Phe Pro Ser Thr His Gly Lys Phe Asp Tyr Trp Gly Gln Gly
            100                 105                 110

Thr Leu Val Thr Val Gln Ser Ala
            115                 120

<210> SEQ ID NO 62
<211> LENGTH: 120
<212> TYPE: PRT
<213> ORGANISM: Artificial Sequence
<220> FEATURE:
<223> OTHER INFORMATION: CDR sequence

<400> SEQUENCE: 62

Glu Val Gln Leu Leu Glu Ser Gly Gly Gly Val Val Gln Pro Gly Gly
 1               5                   10                  15

Ser Leu Arg Leu Ser Cys Ala Ala Ser Gly Phe Thr Phe Asp Thr Ser
                 20                  25                  30

Ser Met Leu Trp Val Arg Gln Ala Pro Gly Lys Gly Leu Glu Trp Val
             35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Lys Phe Pro Ser Thr His Gly Lys Phe Asp Tyr Trp Gly Gln Gly
            100                 105                 110

Thr Leu Val Thr Val Lys Ser Ala
            115                 120

<210> SEQ ID NO 63
<211> LENGTH: 120
<212> TYPE: PRT
<213> ORGANISM: Artificial Sequence
<220> FEATURE:
<223> OTHER INFORMATION: CDR sequence

<400> SEQUENCE: 63

Glu Val Gln Leu Leu Glu Ser Gly Gly Gly Val Val Gln Pro Gly Gly
 1               5                   10                  15

Ser Leu Arg Leu Ser Cys Ala Ala Ser Gly Phe Thr Phe Asp Thr Ser
                 20                  25                  30

Ser Met Leu Trp Val Arg Gln Ala Pro Gly Lys Gly Leu Glu Trp Val
             35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Leu Tyr Tyr Cys
                 85                  90                  95

Ala Lys Phe Pro Ser Thr His Gly Lys Phe Asp Tyr Trp Gly Gln Gly

```
                100             105             110
Thr Leu Val Thr Val Gln Ser Ala
        115                 120

<210> SEQ ID NO 64
<211> LENGTH: 120
<212> TYPE: PRT
<213> ORGANISM: Artificial Sequence
<220> FEATURE:
<223> OTHER INFORMATION: CDR sequence

<400> SEQUENCE: 64

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Lys Phe Pro Ser Thr His Gly Lys Phe Asp Tyr Trp Gly Gln Gly
            100                 105                 110

Thr Leu Val Thr Val Ser Ser Ala
        115                 120

<210> SEQ ID NO 65
<211> LENGTH: 120
<212> TYPE: PRT
<213> ORGANISM: Artificial Sequence
<220> FEATURE:
<223> OTHER INFORMATION: CDR sequence

<400> SEQUENCE: 65

Glu Val Gln Leu Leu Glu Ser Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Thr His Gly Lys Phe Asp Tyr Trp Gly Gln Gly
            100                 105                 110

Thr Leu Val Thr Val Ser Ser Ala
        115                 120

<210> SEQ ID NO 66
<211> LENGTH: 120
<212> TYPE: PRT
<213> ORGANISM: Artificial Sequence
<220> FEATURE:
```

<223> OTHER INFORMATION: CDR sequence

<400> SEQUENCE: 66

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Thr His Gly Lys Phe Asp Tyr Trp Gly Gln Gly
            100                 105                 110

Thr Leu Val Lys Val Ser Ser Ala
            115                 120

<210> SEQ ID NO 67
<211> LENGTH: 120
<212> TYPE: PRT
<213> ORGANISM: Artificial Sequence
<220> FEATURE:
<223> OTHER INFORMATION: CDR sequence

<400> SEQUENCE: 67

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Thr His Gly Lys Phe Asp Tyr Trp Gly Gln Gly
            100                 105                 110

Thr Leu Val Gln Val Ser Ser Ala
            115                 120

<210> SEQ ID NO 68
<211> LENGTH: 120
<212> TYPE: PRT
<213> ORGANISM: Artificial Sequence
<220> FEATURE:
<223> OTHER INFORMATION: CDR sequence

<400> SEQUENCE: 68

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val

```
                35                  40                  45
Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Pro Ser Thr His Gly Lys Phe Asp Tyr Trp Gly Gln Gly
            100                 105                 110

Thr Leu Val Lys Val Ser Ser Ala
            115                 120

<210> SEQ ID NO 69
<211> LENGTH: 120
<212> TYPE: PRT
<213> ORGANISM: Artificial Sequence
<220> FEATURE:
<223> OTHER INFORMATION: CDR sequence

<400> SEQUENCE: 69

Glu Val Gln Leu Leu Glu Ser Gly Gly Gly Val Val Gln Pro Gly Gly
 1               5                  10                  15

Ser Leu Arg Leu Ser Cys Ala Ala Ser Gly Phe Thr Phe Asp Thr Ser
                 20                  25                  30

Ser Met Leu Trp Val Arg Gln Ala Pro Gly Lys Gly Leu Glu Trp Val
                35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Pro Ser Thr His Gly Lys Phe Asp Tyr Trp Gly Gln Gly
            100                 105                 110

Thr Leu Val Gln Val Ser Ser Ala
            115                 120

<210> SEQ ID NO 70
<211> LENGTH: 120
<212> TYPE: PRT
<213> ORGANISM: Artificial Sequence
<220> FEATURE:
<223> OTHER INFORMATION: CDR sequence

<400> SEQUENCE: 70

Glu Val Gln Leu Leu Glu Ser Gly Gly Gly Val Val Gln Pro Gly Gly
 1               5                  10                  15

Ser Leu Arg Leu Ser Cys Ala Ala Ser Gly Phe Thr Phe Asp Thr Ser
                 20                  25                  30

Ser Met Leu Trp Val Arg Gln Ala Pro Gly Lys Gly Leu Glu Trp Val
                35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95
```

Ala Lys Phe Pro Ser Thr His Gly Lys Phe Asp Tyr Trp Gly Gln Gly
            100                 105                 110

Thr Leu Val Thr Val Lys Ser Ala
            115                 120

<210> SEQ ID NO 71
<211> LENGTH: 120
<212> TYPE: PRT
<213> ORGANISM: Artificial Sequence
<220> FEATURE:
<223> OTHER INFORMATION: CDR sequence

<400> SEQUENCE: 71

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Pro Ser Thr His Gly Lys Phe Asp Tyr Trp Gly Gln Gly
            100                 105                 110

Thr Leu Val Thr Val Gln Ser Ala
            115                 120

<210> SEQ ID NO 72
<211> LENGTH: 119
<212> TYPE: PRT
<213> ORGANISM: Artificial Sequence
<220> FEATURE:
<223> OTHER INFORMATION: CDR sequence

<400> SEQUENCE: 72

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Ser Arg Met Lys Phe Asp Tyr Trp Gly Gln Gly
            100                 105                 110

Thr Leu Val Lys Val Ser Ser
            115

<210> SEQ ID NO 73
<211> LENGTH: 119
<212> TYPE: PRT
<213> ORGANISM: Artificial Sequence
<220> FEATURE:
<223> OTHER INFORMATION: CDR sequence

<400> SEQUENCE: 73

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Ser Arg Met Lys Phe Asp Tyr Trp Gly Gln Gly
            100                 105                 110

Thr Leu Val Lys Val Ser Ser
        115

<210> SEQ ID NO 74
<211> LENGTH: 119
<212> TYPE: PRT
<213> ORGANISM: Artificial Sequence
<220> FEATURE:
<223> OTHER INFORMATION: CDR sequence

<400> SEQUENCE: 74

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Ser Arg Met Lys Phe Asp Tyr Trp Gly Gln Gly
            100                 105                 110

Thr Leu Val Thr Val Lys Ser
        115

<210> SEQ ID NO 75
<211> LENGTH: 119
<212> TYPE: PRT
<213> ORGANISM: Artificial Sequence
<220> FEATURE:
<223> OTHER INFORMATION: CDR sequence

<400> SEQUENCE: 75

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Ser Arg Met Lys Phe Asp Tyr Trp Gly Gln Gly
            100                 105                 110

Thr Leu Val Thr Val Gln Ser
            115

<210> SEQ ID NO 76
<211> LENGTH: 119
<212> TYPE: PRT
<213> ORGANISM: Artificial Sequence
<220> FEATURE:
<223> OTHER INFORMATION: CDR sequence

<400> SEQUENCE: 76

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Ser Arg Met Lys Phe Asp Tyr Trp Gly Gln Gly
            100                 105                 110

Thr Leu Val Thr Val Lys Ser
            115

<210> SEQ ID NO 77
<211> LENGTH: 119
<212> TYPE: PRT
<213> ORGANISM: Artificial Sequence
<220> FEATURE:
<223> OTHER INFORMATION: CDR sequence

<400> SEQUENCE: 77

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

```
Ala Lys Phe Pro Ser Ser Arg Met Lys Phe Asp Tyr Trp Gly Gln Gly
            100                 105                 110

Thr Leu Val Thr Val Gln Ser
        115

<210> SEQ ID NO 78
<211> LENGTH: 119
<212> TYPE: PRT
<213> ORGANISM: Artificial Sequence
<220> FEATURE:
<223> OTHER INFORMATION: CDR sequence

<400> SEQUENCE: 78

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
                85                  90                  95

Ala Lys Phe Pro Ser Ser Arg Met Lys Phe Asp Tyr Trp Gly Gln Gly
            100                 105                 110

Thr Leu Val Thr Val Ser Ser
        115

<210> SEQ ID NO 79
<211> LENGTH: 119
<212> TYPE: PRT
<213> ORGANISM: Artificial Sequence
<220> FEATURE:
<223> OTHER INFORMATION: CDR sequence

<400> SEQUENCE: 79

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Ser Arg Met Lys Phe Asp Tyr Trp Gly Gln Gly
            100                 105                 110

Thr Leu Val Thr Val Ser Ser
        115

<210> SEQ ID NO 80
<211> LENGTH: 119
<212> TYPE: PRT
```

<213> ORGANISM: Artificial Sequence
<220> FEATURE:
<223> OTHER INFORMATION: CDR sequence

<400> SEQUENCE: 80

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Ser Arg Met Lys Phe Asp Tyr Trp Gly Gln Gly
            100                 105                 110

Thr Leu Val Lys Val Ser Ser
        115

<210> SEQ ID NO 81
<211> LENGTH: 119
<212> TYPE: PRT
<213> ORGANISM: Artificial Sequence
<220> FEATURE:
<223> OTHER INFORMATION: CDR sequence

<400> SEQUENCE: 81

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Ser Arg Met Lys Phe Asp Tyr Trp Gly Gln Gly
            100                 105                 110

Thr Leu Val Gln Val Ser Ser
        115

<210> SEQ ID NO 82
<211> LENGTH: 119
<212> TYPE: PRT
<213> ORGANISM: Artificial Sequence
<220> FEATURE:
<223> OTHER INFORMATION: CDR sequence

<400> SEQUENCE: 82

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
         35                  40                  45

Ser Val Ile His Gln Ser Gly Thr Pro Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Pro Ser Ser Arg Met Lys Phe Asp Tyr Trp Gly Gln Gly
             100                 105                 110

Thr Leu Val Lys Val Ser Ser
         115

<210> SEQ ID NO 83
<211> LENGTH: 119
<212> TYPE: PRT
<213> ORGANISM: Artificial Sequence
<220> FEATURE:
<223> OTHER INFORMATION: CDR sequence

<400> SEQUENCE: 83

Glu Val Gln Leu Leu Glu Ser Gly Gly Gly Val Val Gln Pro Gly Gly
 1               5                  10                  15

Ser Leu Arg Leu Ser Cys Ala Ala Ser Gly Phe Thr Phe Asp Thr Ser
             20                  25                  30

Ser Met Leu Trp Val Arg Gln Ala Pro Gly Lys Gly Leu Glu Trp Val
         35                  40                  45

Ser Val Ile His Gln Ser Gly Thr Pro Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Phe Pro Ser Ser Arg Met Lys Phe Asp Tyr Trp Gly Gln Gly
             100                 105                 110

Thr Leu Val Gln Val Ser Ser
         115

<210> SEQ ID NO 84
<211> LENGTH: 119
<212> TYPE: PRT
<213> ORGANISM: Artificial Sequence
<220> FEATURE:
<223> OTHER INFORMATION: CDR sequence

<400> SEQUENCE: 84

Glu Val Gln Leu Leu Glu Ser Gly Gly Gly Val Val Gln Pro Gly Gly
 1               5                  10                  15

Ser Leu Arg Leu Ser Cys Ala Ala Ser Gly Phe Thr Phe Asp Thr Ser
             20                  25                  30

Ser Met Leu Trp Val Arg Gln Ala Pro Gly Lys Gly Leu Glu Trp Val
         35                  40                  45

Ser Val Ile His Gln Ser Gly Thr Pro Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys

```
                        85                  90                  95

Ala Lys Phe Pro Ser Ser Arg Met Lys Phe Asp Tyr Trp Gly Gln Gly
                100                 105                 110

Thr Leu Val Thr Val Lys Ser
        115

<210> SEQ ID NO 85
<211> LENGTH: 119
<212> TYPE: PRT
<213> ORGANISM: Artificial Sequence
<220> FEATURE:
<223> OTHER INFORMATION: CDR sequence

<400> SEQUENCE: 85

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Pro Ser Ser Arg Met Lys Phe Asp Tyr Trp Gly Gln Gly
                100                 105                 110

Thr Leu Val Thr Val Gln Ser
        115

<210> SEQ ID NO 86
<211> LENGTH: 120
<212> TYPE: PRT
<213> ORGANISM: Artificial Sequence
<220> FEATURE:
<223> OTHER INFORMATION: CDR sequence

<400> SEQUENCE: 86

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Ser Arg Met Lys Phe Asp Tyr Trp Gly Gln Gly
                100                 105                 110

Thr Leu Val Lys Val Ser Ser Ala
        115                 120

<210> SEQ ID NO 87
<211> LENGTH: 120
```

-continued

```
<212> TYPE: PRT
<213> ORGANISM: Artificial Sequence
<220> FEATURE:
<223> OTHER INFORMATION: CDR sequence

<400> SEQUENCE: 87

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Ser Arg Met Lys Phe Asp Tyr Trp Gly Gln Gly
            100                 105                 110

Thr Leu Val Gln Val Ser Ser Ala
        115                 120

<210> SEQ ID NO 88
<211> LENGTH: 120
<212> TYPE: PRT
<213> ORGANISM: Artificial Sequence
<220> FEATURE:
<223> OTHER INFORMATION: CDR sequence

<400> SEQUENCE: 88

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Ser Arg Met Lys Phe Asp Tyr Trp Gly Gln Gly
            100                 105                 110

Thr Leu Val Thr Val Lys Ser Ala
        115                 120

<210> SEQ ID NO 89
<211> LENGTH: 120
<212> TYPE: PRT
<213> ORGANISM: Artificial Sequence
<220> FEATURE:
<223> OTHER INFORMATION: CDR sequence

<400> SEQUENCE: 89

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
```

```
            20                  25                  30
Ser Met Leu Trp Val Arg Gln Ala Pro Gly Lys Gly Leu Glu Trp Val
        35                  40                  45
Ser Val Ile His Gln Ser Gly Thr Pro Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Leu Tyr Tyr Cys
                85                  90                  95
Ala Lys Phe Pro Ser Ser Arg Met Lys Phe Asp Tyr Trp Gly Gln Gly
            100                 105                 110
Thr Leu Val Thr Val Gln Ser Ala
            115                 120

<210> SEQ ID NO 90
<211> LENGTH: 120
<212> TYPE: PRT
<213> ORGANISM: Artificial Sequence
<220> FEATURE:
<223> OTHER INFORMATION: CDR sequence

<400> SEQUENCE: 90

Glu Val Gln Leu Leu Glu Ser Gly Gly Gly Val Val Gln Pro Gly Gly
1               5                   10                  15
Ser Leu Arg Leu Ser Cys Ala Ala Ser Gly Phe Thr Phe Asp Thr Ser
            20                  25                  30
Ser Met Leu Trp Val Arg Gln Ala Pro Gly Lys Gly Leu Glu Trp Val
        35                  40                  45
Ser Val Ile His Gln Ser Gly Thr Pro Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Leu Tyr Tyr Cys
                85                  90                  95
Ala Lys Phe Pro Ser Ser Arg Met Lys Phe Asp Tyr Trp Gly Gln Gly
            100                 105                 110
Thr Leu Val Thr Val Lys Ser Ala
            115                 120

<210> SEQ ID NO 91
<211> LENGTH: 120
<212> TYPE: PRT
<213> ORGANISM: Artificial Sequence
<220> FEATURE:
<223> OTHER INFORMATION: CDR sequence

<400> SEQUENCE: 91

Glu Val Gln Leu Leu Glu Ser Gly Gly Gly Val Val Gln Pro Gly Gly
1               5                   10                  15
Ser Leu Arg Leu Ser Cys Ala Ala Ser Gly Phe Thr Phe Asp Thr Ser
            20                  25                  30
Ser Met Leu Trp Val Arg Gln Ala Pro Gly Lys Gly Leu Glu Trp Val
        35                  40                  45
Ser Val Ile His Gln Ser Gly Thr Pro Thr Tyr Tyr Ala Asp Ser Val
    50                  55                  60
Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Leu Tyr Tyr Cys
            85                  90                  95

Ala Lys Phe Pro Ser Ser Arg Met Lys Phe Asp Tyr Trp Gly Gln Gly
            100                 105                 110

Thr Leu Val Thr Val Gln Ser Ala
            115                 120

<210> SEQ ID NO 92
<211> LENGTH: 120
<212> TYPE: PRT
<213> ORGANISM: Artificial Sequence
<220> FEATURE:
<223> OTHER INFORMATION: CDR sequence

<400> SEQUENCE: 92

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Thr Tyr Tyr Cys
            85                  90                  95

Ala Lys Phe Pro Ser Ser Arg Met Lys Phe Asp Tyr Trp Gly Gln Gly
            100                 105                 110

Thr Leu Val Thr Val Ser Ser Ala
            115                 120

<210> SEQ ID NO 93
<211> LENGTH: 120
<212> TYPE: PRT
<213> ORGANISM: Artificial Sequence
<220> FEATURE:
<223> OTHER INFORMATION: CDR sequence

<400> SEQUENCE: 93

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
            85                  90                  95

Ala Lys Phe Pro Ser Ser Arg Met Lys Phe Asp Tyr Trp Gly Gln Gly
            100                 105                 110

Thr Leu Val Thr Val Ser Ser Ala
            115                 120

<210> SEQ ID NO 94

-continued

```
<211> LENGTH: 120
<212> TYPE: PRT
<213> ORGANISM: Artificial Sequence
<220> FEATURE:
<223> OTHER INFORMATION: CDR sequence

<400> SEQUENCE: 94

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Ser Arg Met Lys Phe Asp Tyr Trp Gly Gln Gly
            100                 105                 110

Thr Leu Val Lys Val Ser Ser Ala
            115                 120

<210> SEQ ID NO 95
<211> LENGTH: 120
<212> TYPE: PRT
<213> ORGANISM: Artificial Sequence
<220> FEATURE:
<223> OTHER INFORMATION: CDR sequence

<400> SEQUENCE: 95

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Leu Tyr Tyr Cys
                85                  90                  95

Ala Lys Phe Pro Ser Ser Arg Met Lys Phe Asp Tyr Trp Gly Gln Gly
            100                 105                 110

Thr Leu Val Gln Val Ser Ser Ala
            115                 120

<210> SEQ ID NO 96
<211> LENGTH: 120
<212> TYPE: PRT
<213> ORGANISM: Artificial Sequence
<220> FEATURE:
<223> OTHER INFORMATION: CDR sequence

<400> SEQUENCE: 96

Glu Val Gln Leu Leu Glu Ser Gly Gly Gly Val Val Gln Pro Gly Gly
1               5                   10                  15
```

```
Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Pro Ser Ser Arg Met Lys Phe Asp Tyr Trp Gly Gln Gly
            100                 105                 110

Thr Leu Val Lys Val Ser Ser Ala
            115                 120

<210> SEQ ID NO 97
<211> LENGTH: 120
<212> TYPE: PRT
<213> ORGANISM: Artificial Sequence
<220> FEATURE:
<223> OTHER INFORMATION: CDR sequence

<400> SEQUENCE: 97

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Pro Ser Ser Arg Met Lys Phe Asp Tyr Trp Gly Gln Gly
            100                 105                 110

Thr Leu Val Gln Val Ser Ser Ala
            115                 120

<210> SEQ ID NO 98
<211> LENGTH: 120
<212> TYPE: PRT
<213> ORGANISM: Artificial Sequence
<220> FEATURE:
<223> OTHER INFORMATION: CDR sequence

<400> SEQUENCE: 98

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80
```

Leu Gln Met Asn Ser Leu Arg Ala Glu Asp Thr Ala Val Tyr Tyr Cys
                85                  90                  95

Ala Lys Phe Pro Ser Ser Arg Met Lys Phe Asp Tyr Trp Gly Gln Gly
            100                 105                 110

Thr Leu Val Thr Val Lys Ser Ala
        115                 120

<210> SEQ ID NO 99
<211> LENGTH: 120
<212> TYPE: PRT
<213> ORGANISM: Artificial Sequence
<220> FEATURE:
<223> OTHER INFORMATION: CDR sequence

<400> SEQUENCE: 99

Glu Val Gln Leu Leu Glu Ser Gly Gly Gly Val Val Gln Pro Gly Gly
1               5                   10                  15

Ser Leu Arg Leu Ser Cys Ala Ala Ser Gly Phe Thr Phe Asp Thr Ser
            20                  25                  30

Ser Met Leu Trp Val Arg Gln Ala Pro Gly Lys Gly Leu Glu Trp Val
        35                  40                  45

Ser Val Ile His Gln Ser Gly Thr Pro Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Phe Pro Ser Ser Arg Met Lys Phe Asp Tyr Trp Gly Gln Gly
            100                 105                 110

Thr Leu Val Thr Val Gln Ser Ala
        115                 120

<210> SEQ ID NO 100
<211> LENGTH: 34
<212> TYPE: PRT
<213> ORGANISM: Artificial Sequence
<220> FEATURE:
<223> OTHER INFORMATION: HIS6-FLAG3 tag

<400> SEQUENCE: 100

His His His His His Gly Ala Ala Asp Tyr Lys Asp His Asp Gly
1               5                   10                  15

Asp Tyr Lys Asp His Asp Ile Asp Tyr Lys Asp Asp Asp Lys Gly
            20                  25                  30

Ala Ala

<210> SEQ ID NO 101
<211> LENGTH: 5
<212> TYPE: PRT
<213> ORGANISM: Artificial Sequence
<220> FEATURE:
<223> OTHER INFORMATION: C-terminal end

<400> SEQUENCE: 101

Val Thr Val Lys Ser
1               5

<210> SEQ ID NO 102
<211> LENGTH: 5
<212> TYPE: PRT

```
<213> ORGANISM: Artificial Sequence
<220> FEATURE:
<223> OTHER INFORMATION: C-terminal end

<400> SEQUENCE: 102

Val Thr Val Gln Ser
1               5

<210> SEQ ID NO 103
<211> LENGTH: 5
<212> TYPE: PRT
<213> ORGANISM: Artificial Sequence
<220> FEATURE:
<223> OTHER INFORMATION: C-terminal end

<400> SEQUENCE: 103

Val Lys Val Ser Ser
1               5

<210> SEQ ID NO 104
<211> LENGTH: 5
<212> TYPE: PRT
<213> ORGANISM: Artificial Sequence
<220> FEATURE:
<223> OTHER INFORMATION: C-terminal end

<400> SEQUENCE: 104

Val Gln Val Ser Ser
1               5

<210> SEQ ID NO 105
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 105

Val Thr Val Lys Ser Xaa
1               5

<210> SEQ ID NO 106
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 106

Val Thr Val Gln Ser Xaa
1               5

<210> SEQ ID NO 107
<211> LENGTH: 6
<212> TYPE: PRT
<213> ORGANISM: Artificial Sequence
<220> FEATURE:
```

```
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 107

Val Lys Val Ser Ser Xaa
1               5

<210> SEQ ID NO 108
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 108

Val Gln Val Ser Ser Xaa
1               5

<210> SEQ ID NO 109
<211> LENGTH: 6
<212> TYPE: PRT
<213> ORGANISM: Artificial Sequence
<220> FEATURE:
<223> OTHER INFORMATION: C-terminal end

<400> SEQUENCE: 109

Val Thr Val Lys Ser Ala
1               5

<210> SEQ ID NO 110
<211> LENGTH: 6
<212> TYPE: PRT
<213> ORGANISM: Artificial Sequence
<220> FEATURE:
<223> OTHER INFORMATION: C-terminal end

<400> SEQUENCE: 110

Val Thr Val Gln Ser Ala
1               5

<210> SEQ ID NO 111
<211> LENGTH: 6
<212> TYPE: PRT
<213> ORGANISM: Artificial Sequence
<220> FEATURE:
<223> OTHER INFORMATION: C-terminal end

<400> SEQUENCE: 111

Val Lys Val Ser Ser Ala
1               5

<210> SEQ ID NO 112
<211> LENGTH: 6
<212> TYPE: PRT
<213> ORGANISM: Artificial Sequence
<220> FEATURE:
<223> OTHER INFORMATION: C-terminal end
```

```
<400> SEQUENCE: 112

Val Gln Val Ser Ser Ala
1               5

<210> SEQ ID NO 113
<211> LENGTH: 5
<212> TYPE: PRT
<213> ORGANISM: Artificial Sequence
<220> FEATURE:
<223> OTHER INFORMATION: C-terminal end

<400> SEQUENCE: 113

Val Thr Val Ser Ser
1               5

<210> SEQ ID NO 114
<211> LENGTH: 6
<212> TYPE: PRT
<213> ORGANISM: Artificial Sequence
<220> FEATURE:
<223> OTHER INFORMATION: C-terminal end
<220> FEATURE:
<221> NAME/KEY: SITE
<222> LOCATION: (6)..(6)
<223> OTHER INFORMATION: Xaa stands for (X)n which means C-terminal
      extension with n amino acids, wherein each position is chosen
      independently from any amino acids

<400> SEQUENCE: 114

Val Thr Val Ser Ser Xaa
1               5

<210> SEQ ID NO 115
<211> LENGTH: 6
<212> TYPE: PRT
<213> ORGANISM: Artificial Sequence
<220> FEATURE:
<223> OTHER INFORMATION: C-terminal end

<400> SEQUENCE: 115

Val Thr Val Ser Ser Ala
1               5
```

SERUM ALBUMIN-BINDING IMMUNOGLOBULIN VARIABLE DOMAINS

RELATED APPLICATIONS

This application is a national stage filing under 35 U.S.C. 371 of International Patent Application Serial No. PCT/EP2016/076088, filed Oct. 28, 2016, which claims the benefit under 35 U.S.C. § 119(e) of U.S. Provisional Application Ser. No. 62/254,813, filed Nov. 13, 2015, the contents of each of which is incorporated by reference herein in its entirety for all purposes.

The present invention relates to amino acid sequences binding to serum albumin.

In particular, the present invention relates to improved immunoglobulin single variable domains (also referred to herein as "ISV's" or "ISVD's"), and more in particular improved heavy-chain immunoglobulin single variable domains, binding to serum albumin, as well as to proteins, polypeptides and other constructs, compounds, molecules or chemical entities that comprise such improved serum albumin binders.

Other aspects, embodiments, features, uses and advantages of the invention will be clear to the skilled person based on the disclosure herein.

The improved serum albumin binding ISVDs provided by the invention are also referred to herein as the "serum albumin binders of the invention", "albumin binders of the invention" or "serum albumin binders" or "albumin binders". Also, proteins, polypeptides and other constructs, compounds, molecules or chemical entities that comprise at least one serum albumin binder of the invention are also referred to herein as "compounds of the invention" or "polypeptides of the invention".

Preferably, the polypeptides of the invention are fusion proteins.

In the present application, the amino acid residues/positions in an immunoglobulin heavy-chain variable domain will be indicated with the numbering according to Kabat. For the sake of convenience, FIG. 1 gives a table listing some of the amino acid positions that will be specifically referred to herein and their numbering according to some alternative numbering systems (such as Aho and IMGT. Note: unless explicitly indicated otherwise, for the present description and claims, Kabat numbering is decisive; other numbering systems are given for reference only).

With regard to the CDR's, as is well-known in the art, there are multiple conventions to define and describe the CDR's of a VH or VHH fragment, such as the Kabat definition (which is based on sequence variability and is the most commonly used) and the Chothia definition (which is based on the location of the structural loop regions). Reference is for example made to the website bioinf.org.uk/abs/. For the purposes of the present specification and claims, even though the CDR's according to Kabat may also be mentioned, the CDRs are most preferably defined on the basis of the Abm definition (which is based on Oxford Molecular's AbM antibody modelling software), as this is considered to be an optimal compromise between the Kabat and Chothia definitions. Reference is again made to the website bioinf.org.uk/abs/).

ISVD's that can bind to serum albumin and their uses are well-known in the art, for example from WO 2004/041865, WO 2006/122787, EP 2 139 918, WO 2011/006915, WO 2012/175400 and WO 2014/111550, which describe serum albumin-binding ISVD's and their use for extending the serum half-life (as defined in these applications) of therapeutic compounds, moieties and entities.

The present invention aims to provide improved serum albumin binders, in particular compared to the serum albumin binders disclosed in WO 2011/006915 and WO 2014/111550. Representative examples of serum albumin binders known from these two PCT applications are given in Table A below as "Reference A" to "Reference D", respectively. An alignment of these reference sequences is given in FIG. 2. The (combinations of) CDR's of these reference compounds (according to the Kabat and Abm conventions, respectively) are listed in Table B.

More in particular, the invention aims to provide improved serum albumin-binding ISVD's that are variants of the serum albumin-binding ISVD's mentioned in Table A and that have reduced binding by interfering factors (generally referred to as "pre-existing antibodies") that may be present in the sera from some healthy human subjects as well as from patients. Reference is made to WO 12/175741, WO 2013/024059 and also for example by Holland et al. (J. Clin. Immunol. 2013, 33(7):1192-203) as well as to the co-pending non-prepublished PCT application PCT/EP2015/060643 by Assignee filed on May 13, 2015 and entitled "Improved immunoglobulin variable domains" (published on Nov. 19, 2015 as WO 2015/173325).

TABLE A reference sequences.

| SEQ ID NO: | Binder | Known from | Sequence |
|---|---|---|---|
| 1 | Reference A | WO2011/006915:<br>SEQ ED NO: 184<br>("DOM7r-92") | EVQLLESGGGLVQPGGSLRLSCAASGFTFSTGEMAWVRQAPGKGL<br>EWVSSISSSGATTYYADSVKGRFTISRDNSKNTLYLQMNSLRAEDT<br>AVYYCAKPRHPQGGVTFDYWGQGTLVTVSS |
| 2 | Reference B | WO2011/006915:<br>SEQ ID NO: 201<br>("DOM7r-92-4") | EVQLLESGGGLVQPGGSLRLSCAASGFTFDTSSMLWVRQAPGKGL<br>EWVSVIHQSGTPTYYADSVKGRFTISRDNSKNTLYLQMNSLRAED<br>TAVYYCAKFPSTHGKFDYWGQGTLVTVSS |
| 3 | Reference C | WO2014/111550:<br>SEQ ID NO: 4<br>("DOM7r-92-100") | EVQLLESGGGLVQPGGSLRLSCAASGFTFDTSSMLWVRQAPGKGL<br>EWVSVIHQSGTPTYYADSVKGRFTISRDNSKNTLYLQMNSLRAED<br>TAVYYCAKFPSSRMKFDYWGQGTLVTVSS |
| 4 | Reference D | WO2014/111550:<br>SEQ ID NO: 6<br>("DOM7r-92-104") | EVQLLESGGGLVQPGGSLRLSCAASGFTFDTSSMLWVRQAPGKGL<br>EWVSVIHQSGTPTYYADSVKGRFTISRDNSKNTLYLQMNSLRAED<br>TAVYYCAKFPSSRMKFDYWGQGTLVTVSSA |

TABLE B

CDR's of Reference Compounds A to D (according to Kabat and Abm)

| Reference | | | Sequence | SEQ ID NO: |
|---|---|---|---|---|
| Reference A | CDR1 | (Kabat) | TGEMA | 5 |
| | CDR2 | (Kabat) | SISSSGATTYYADSVKG | 6 |
| | CDR3 | (Kabat) | PRHPQGGVTFDY | 7 |
| Reference A | CDR1 | (Abm) | GFTFSTGEMA | 8 |
| | CDR2 | (Abm) | SISSSGATTY | 9 |
| | CDR3 | (Abm) | PRHPQGGVTFDY | 7 |
| Reference B | CDR1 | (Kabat) | TSSML | 10 |
| | CDR2 | (Kabat) | VIHQSGTPTYYADSVKG | 11 |
| | CDR3 | (Kabat) | FPSTHGKFDY | 12 |
| Reference B | CDR1 | (Abm) | GFTFDTSSML | 13 |
| | CDR2 | (Abm) | VIHQSGTPTY | 14 |
| | CDR3 | (Abm) | FPSTHGKFDY | 12 |
| Reference C | CDR1 | (Kabat) | TSSML | 10 |
| | CDR2 | (Kabat) | VIHQSGTPTYYADSVKG | 11 |
| | CDR3 | (Kabat) | FPSSRMKFDY | 15 |
| Reference C | CDR1 | (Abm) | GFTFDTSSML | 13 |
| | CDR2 | (Abm) | VIHQSGTPTY | 14 |
| | CDR3 | (Abm) | FPSSRMKFDY | 15 |
| Reference D | CDR1 | (Kabat) | TSSML | 10 |
| | CDR2 | (Kabat) | VIHQSGTPTYYADSVKG | 11 |
| | CDR3 | (Kabat) | FPSSRMKFDY | 15 |
| Reference D | CDR1 | (Abm) | GFTFDTSSML | 13 |
| | CDR2 | (Abm) | VIHQSGTPTY | 14 |
| | CDR3 | (Abm) | FPSSRMKFDY | 15 |

Notes (see also the alignment in FIG. 2):
Reference C and Reference D have the same CDR's.
Reference B, Reference C and Reference D have the same CDR1 and CDR2
The CDR3's according to the Kabat convention are the same as the CDR3's according to the Abm convention As further described herein, the serum albumin binders of the invention preferably have the same combinations of CDR's (i.e. CDR1, CDR2 and CDR3) as are present in one of References A, B, C or D, and most preferably have the same combination of CDR's as is present in Reference C or Reference D (which have the same CDRs).

Of the serum albumin binders listed in Table A, the binder of SEQ ID NO: 4 has a C-terminal alanine extension, i.e. an alanine residue at the C-terminal end of the ISVD-sequence (also sometimes referred to as "position 114") compared to the usual C-terminal sequence VTVSS (SEQ ID NO:113, as present in the binders of SEQ ID NO's: 1 to 3). As described in WO 12/175741 (but also for example in WO 2013/024059), this C-terminal alanine extension can prevent the binding of so-called "pre-existing antibodies" (assumed to be IgG's) to a putative epitope that is situated at the C-terminal region of the ISV. This epitope is assumed to include, among other residues, the surface-exposed amino acid residues of the C-terminal sequence VTVSS as well as the amino acid residue at position 14 (and the amino acid residues next/close to the same in the amino acid sequence, such as positions 11, 13 and 15) and may also comprise the amino acid residue at position 83 (and the amino acid residues next/close to the same in the amino acid sequence, such as positions 82, 82a, 82b and 84) and/or the amino acid residue at position 108 (and the amino acid residues next/close to the same in the amino acid sequence, such as position 107).

However, although the presence of such a C-terminal alanine (or a C-terminal extension generally) can greatly reduce (and in a lot of cases even essentially fully prevent) the binding of the "pre-existing antibodies" that can be found in the sera from a range of subjects (both healthy subjects as patients), it has been found that the sera from some subjects (such as the sera from patients with some immune diseases such as SLE) can contain pre-existing antibodies that can bind to the C-terminal region of an ISV (when such region is exposed) even when the ISV contains such a C-terminal alanine (or more generally, such C-terminal extension). Reference is again made to the co-pending non-prepublished PCT application PCT/EP2015/060643 by Assignee filed on May 13, 2015 and entitled "Improved immunoglobulin variable domains".

Accordingly, one specific objective of the invention is to provide serum albumin binders that are improved variants of the serum albumin-binding ISVD's listed in Table A and that have reduced binding by so-called "pre-existing antibodies", and in particular of the kind described in PCT/EP2015/060643 (i.e. those pre-existing antibodies that can bind to an exposed C-terminal region of an ISV even in the presence of a C-terminal extension).

Generally, the invention achieves this objective by providing serum albumin-binding ISV's that are variants of the sequences of SEQ ID NO's: 1 to 4 (and in particular variants of the sequences of SEQ ID NO:3 or SEQ ID NO:4) that comprise the following amino acid residues (i.e. mutations compared to the sequences of SEQ ID NO's: 1 to 4):

89T; or 89L in combination with 11V; or 89L in combination with 110K or 110Q; or 89L in combination with 112K or 112Q; or
89L in combination with 11V and 110K or 110Q; or
89L in combination with 11V and 112K or 112Q; or
11V in combination with 110K or 110Q; or
11V in combination with 112K or 112Q.

In a specific aspect, in the serum albumin binders of the invention:
the amino acid residue at position 11 is preferably chosen from L, V or K; and
the amino acid residue at position 89 is preferably suitably chosen from T, V or L; and
the amino acid residue at position 110 is preferably suitably chosen from T, K or Q; and
the amino acid residue at position 112 is preferably suitably chosen from S, K or Q; such that (i) position 89 is T; or (ii) position 110 is K or Q; or (iii) position 112 is K or Q; or (iv) position 89 is L and position 11 is V; or (v) position 89 is L and position 110 is K or Q; or (vi) position 89 is L and position 112 is K or Q; or (vi) position 89 is L and position 11 is V and position 110 is K or Q; or (vii) position 89 is L and position 11 is V and position 112 is K or Q; or (viii) position 11 is V and position 110 is K or Q; or (ix) position 11 is V and position 112 is K or Q.

Of the amino acid sequences provided by the invention, amino acid sequences in which position 89 is T or in which position 11 is V and position 89 is L (optionally in suitable combination with a 110K or 110Q mutation and/or a 112K or 112Q mutation, and in particular in combination with a 110K or 110Q mutation) are particularly preferred. Even more preferred are amino acid sequences in which position 11 is V and position 89 is L, optionally with a 110K or 110Q mutation.

The amino acid sequences of the invention preferably bind to (human) serum albumin with an affinity better than 100 nM, preferably better than 50 nM. For example, albumin binders of the invention that are variants of Reference A or Reference B, respectively, may have an affinity for (human) serum albumin that is about the same as described for Reference A or Reference B, respectively, in WO 2011/006915; and similarly, albumin binders of the invention that are variants of Reference C and/or Reference D, respectively, may have an affinity for (human) serum albumin that is about the same as described for Reference C and/or Reference D, respectively, in WO 2014/111550 (with affinity being measured as described in WO 2011/006915 or WO 2014/111550, respectively).

Also, the albumin binders provided by the invention and compounds and polypeptides comprising the same (as further described herein) preferably have a half-life (defined as t1/2 beta) in man that is more than 1 hour, preferably more than 2 hours, more preferably of more than 6 hours, such as of more than 12 hours, and for example of about one day, two days, one week, two weeks and up to the half-life of serum albumin in man (estimated to be around 19 days), although the latter may be less critical.

For example, albumin binders of the invention that are variants of Reference A or Reference B, respectively, may have a half-life in man that is comparable to (and preferably about the same as) the half-life of Reference A or Reference B, respectively (see again WO 2011/006915); and similarly, albumin binders of the invention that are variants of Reference C and/or Reference D, respectively, may have a half-life in man that is comparable to (and preferably about the same as) the half-life of Reference C and/or Reference D, respectively (see again WO 2014/111550).

Also, a compound or polypeptide of the invention comprising an albumin binder that is a variant of Reference A or Reference B, respectively, may have a half-life in man that is comparable to (and preferably about the same as) the half-life of the same compound or polypeptide but with Reference A or Reference B, respectively, instead of the albumin binder of the invention; and similarly, a compound or polypeptide of the invention comprising an albumin binder that is a variant of Reference C or Reference D, respectively, may have a half-life in man that is comparable to (and preferably about the same as) the half-life of the same compound or polypeptide but with Reference C or Reference D, respectively.

Table C list some non-limiting possible combinations of the amino acid residues that can be present at positions 11, 89, 110 and 112 in the serum albumin binders of the invention. Combinations that are particularly preferred are indicated in bold, and the most preferred combinations are indicated in bold/underline.

TABLE C

Possible combinations of amino acids at positions 11, 89, 110 and 112.

| | | POSITION | | | |
|---|---|---|---|---|---|
| | | 11 | 89 | 110 | 112 |
| COMBINATION | | _L_ | _T_ | _T_ | _S_ |
| | | L | T | T | K |
| | | L | T | T | Q |
| | | L | T | K | S |
| | | L | T | Q | S |
| | | L | V | T | K |
| | | L | V | T | Q |
| | | L | V | K | S |
| | | L | V | Q | S |
| | | L | L | T | K |
| | | L | L | T | Q |
| | | L | L | K | S |
| | | L | L | Q | S |
| COMBINATION | | V | T | T | S |
| | | V | T | T | K |
| | | V | T | T | Q |
| | | V | T | K | S |
| | | V | T | Q | S |
| | | V | V | T | K |
| | | V | V | T | Q |
| | | V | V | K | S |
| | | V | V | Q | S |
| | | _V_ | _L_ | _T_ | _S_ |
| | | _V_ | _L_ | _T_ | _K_ |
| | | _V_ | _L_ | _T_ | _Q_ |
| | | _V_ | _L_ | _K_ | _S_ |
| | | _V_ | _L_ | _Q_ | _S_ |

The serum albumin binders of the invention are as further described in the description, examples and figures herein, i.e. they have CDRs that are as described herein and have an overall degree of sequence identity (as defined herein) with (one of) the sequences of SEQ ID NOs: 1 to 4 that is as disclosed herein and/or may have a limited number of "amino acid differences" (as described herein) with (one of) these reference sequences.

The serum albumin binders of the invention preferably comprise the following CDRs (according to the Kabat convention):
a CDR1 (according to Kabat) that is chosen from the following sequences: TGEMA (SEQ ID NO: 5) and TSSML (SEQ ID NO:10) and that is preferably TSSML (SEQ ID NO:10); and
a CDR2 (according to Kabat) that is chosen from the following sequences: SISSSGATTYYADSVKG (SEQ ID NO:6) and VIHQSGTPTYYADSVKG (SEQ ID NO: 11) and that is preferably VIHQSGTPTYYADSVKG (SEQ ID NO: 11); and a CDR3 (according to Kabat) that is chosen from the following sequences: PRHPQGGVTFDY (SEQ ID NO:7), FPSTHGKFDY (SEQ ID NO:12) and FPSSRMKFDY (SEQ ID NO:15) and that is preferably FPSTHGKFDY (SEQ ID NO:12) or FPSSRMKFDY (SEQ ID NO: 15) and most preferably FPSSRMKFDY (SEQ ID NO:15).

More preferably, the CDR's are as follows (again given according to the Kabat convention): CDR1 is TSSML (SEQ ID NO:10); CDR2 is VIHQSGTPTYYADSVKG (SEQ ID NO:11) and CDR3 is FPSTHGKFDY (SEQ ID NO:12) or FPSSRMKFDY (SEQ ID NO:15). Most preferably, CDR1 is TSSML (SEQ ID NO:10); CDR2 is VIHQSGTPTYYADSVKG (SEQ ID NO:11) and CDR3 is FPSSRMKFDY (SEQ ID NO:15) Alternatively, when the CDR's are given according to the Abm convention, the serum albumin binders of the invention preferably comprise the following CDRs:

a CDR1 (according to Abm) that is chosen from the following sequences: GFTFSTGEMA (SEQ ID NO: 8) and GFTFDTSSML (SEQ ID NO:13) and that is preferably GFTFDTSSML (SEQ ID NO:13); and a CDR2 (according to Abm) that is chosen from the following sequences: SISSSGATTY (SEQ ID NO:9) and VIHQSGTPTY (SEQ ID NO:14) and that is preferably VIHQSGTPTY (SEQ ID NO:14); and a CDR3 (according to Abm) that is chosen from the following sequences: PRHPQGGVTFDY (SEQ ID NO:7), FPSTHGKFDY (SEQ ID NO: 12) and FPSSRMKFDY (SEQ ID NO: 15) and that is preferably FPSTHGKFDY (SEQ ID NO: 12) or FPSSRMKFDY (SEQ ID NO: 15) and that is most preferably FPSSRMKFDY (SEQ ID NO: 15).

When given according to the Abm convention, preferably, the CDR's are as follows: CDR1 is GFTFDTSSML (SEQ ID NO:13), CDR2 is VIHQSGTPTY (SEQ ID NO:14) and CDR3 is FPSTHGKFDY (SEQ ID NO: 12) or FPSSRMKFDY (SEQ ID NO: 15). Most preferably, CDR1 is GFTFDTSSML (SEQ ID NO:13), CDR2 is VIHQSGTPTY (SEQ ID NO:14) and CDR3 is FPSSRMKFDY (SEQ ID NO: 15).

A serum albumin binder of the invention preferably also has:

a degree of sequence identity with one of the sequences of SEQ ID NO's: 1 to 4 (in which any C-terminal extension that may be present as well as the CDRs are not taken into account for determining the degree of sequence identity) of at least 85%, preferably at least 90%, more preferably at least 95%; and in particular a degree of sequence identity with the sequence SEQ ID NO: 3 or 4 (in which again any C-terminal extension that may be present as well as the CDRs are not taken into account for determining the degree of sequence identity) of at least 85%, preferably at least 90%, more preferably at least 95%; and/or no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with one of the sequences of SEQ ID NO's: 1 to 4 (in which said amino acid differences, if present, may be present in the frameworks and/or the CDR's but are preferably present only in the frameworks and not in the CDRs); and in particular no more than 5, preferably no more than 3, such as only 3, 2 or 1 such amino acid differences with the sequence of SEQ ID NO: 3 or SEQ ID NO:4 (in which said amino acid differences, if present, may be present in the frameworks and/or the CDR's but are preferably present only in the frameworks and not in the CDRs).

With regard to the various aspects and preferred aspects of the albumin binders of the invention, when it comes to the degree of sequence identity with respect to one of SEQ ID NO: 1, SEQ ID NO:2, SEQ ID NO:3 and/or SEQ ID NO:4, respectively and as applicable, and/or the number and kind of "amino acid differences" that may be present in such a binder of the invention (i.e. compared to one of SEQ ID NO:1, SEQ ID NO:2, SEQ ID NO:3 and/or SEQ ID NO:4, respectively), it should be noted that, when it is said that (i) an amino acid sequence of the invention has a degree of sequence identity with the sequence of SEQ ID NO: 1, SEQ ID NO:2, SEQ ID NO:3 and/or SEQ ID NO:4, respectively and as applicable, of at least 85%, preferably at least 90%, more preferably at least 95% (in which the CDRs, any C-terminal extension that may be present, as well as the mutations at positions 11, 89, 110 and/or 112 required by the specific aspect involved, are not taken into account for determining the degree of sequence identity); and/or when it is said that (ii) an amino acid sequence of the invention has no more than 7, preferably no more than 5, such as only 3, 2 or 1 "amino acid differences" with the sequence of SEQ ID NO: 1, SEQ ID NO:2, SEQ ID NO:3 and/or SEQ ID NO:4, respectively and as applicable (again, not taking into account any C-terminal extension that may be present and not taking into account the mutations at positions 11, 89, 110 and/or 112 required by the specific aspect involved), then this also includes sequences that have no amino acid differences with the sequence of SEQ ID NO: 1, SEQ ID NO:2, SEQ ID NO:3 and/or SEQ ID NO:4, respectively and as applicable, other than the mutations at positions 11, 89, 110 and/or 112 required by the specific aspect involved) and any C-terminal extension that may be present.

Thus, in one specific aspect of the invention, the albumin binders of the invention may have 100% sequence identity with SEQ ID NO:1, SEQ ID NO:2, SEQ ID NO:3 and/or SEQ ID NO:4, respectively and as applicable (including the CDRs, but not taking into account the mutation(s) or combination of mutations at positions 11, 89, 110 and/or 112 disclosed herein and/or any C-terminal extension that may be present), and/or may have no amino acid differences with SEQ ID NO:1, SEQ ID NO:2, SEQ ID NO:3 and/or SEQ ID NO:4, respectively and as applicable (i.e. other than the mutation(s) or combination of mutations at positions 11, 89, 110 and/or 112 disclosed herein and any C-terminal extension that may be present).

When any amino acid differences are present (i.e. besides any C-terminal extension and the mutations at positions 11, 89, 110 and/or 112 that are required by the specific aspect of the invention involved), these amino acid differences may be present in the CDRs and/or in the framework regions, but they are preferably present only in the framework regions (as defined by the Abm convention, i.e. not in the CDRs as defined according to the Abm convention), i.e. such that the albumin binders of the invention have the same combination of CDRs (defined according to the Abm convention) as are present in one of SEQ ID NO: 1, SEQ ID NO:2, SEQ ID NO:3 and/or SEQ ID NO:4, respectively and as applicable.

The serum albumin binders of the invention, when they are present at and/or form the C-terminal end of a compound or polypeptide of the invention (or when they otherwise have an "exposed" C-terminal end in a protein, polypeptide or other compound or construct in which they are present, by which is generally meant that the C-terminal end of the ISV is not associated with or linked to a constant domain (such as a CHI domain); reference is again made to WO 12/175741 and PCT/EP2015/06043) preferably also have a C-terminal extension of the formula $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen from naturally occurring amino acid residues (although according to preferred one aspect, it does not comprise any cysteine residues), and preferably independently chosen from the group consisting of alanine (A), glycine (G), valine (V), leucine (L) or isoleucine (I).

According to some preferred, but non-limiting examples of such C-terminal extensions $X_{(n)}$, X and n can be as follows:

(a) n=1 and X=Ala;
(b) n=2 and each X=Ala;
(c) n=3 and each X=Ala;
(d) n=2 and at least one X=Ala (with the remaining amino acid residue(s) X being independently chosen from any naturally occurring amino acid but preferably being independently chosen from Val, Leu and/or Ile);
(e) n=3 and at least one X=Ala (with the remaining amino acid residue(s) X being independently chosen from any naturally occurring amino acid but preferably being independently chosen from Val, Leu and/or Ile);
(f) n=3 and at least two X=Ala (with the remaining amino acid residue(s) X being independently chosen from any naturally occurring amino acid but preferably being independently chosen from Val, Leu and/or Ile);
(g) n=1 and X=Gly;
(h) n=2 and each X=Gly;
(i) n=3 and each X=Gly,
(j) n=2 and at least one X=Gly (with the remaining amino acid residue(s) X being independently chosen from any naturally occurring amino acid but preferably being independently chosen from Val, Leu and/or Ile);
(k) n=3 and at least one X=Gly (with the remaining amino acid residue(s) X being independently chosen from any naturally occurring amino acid but preferably being independently chosen from Val, Leu and/or Ile);
(l) n=3 and at least two X=Gly (with the remaining amino acid residue(s) X being independently chosen from any naturally occurring amino acid but preferably being independently chosen from Val, Leu and/or Ile);
(m) n=2 and each X=Ala or Gly;
(n) n=3 and each X=Ala or Gly;
(o) n=3 and at least one X=Ala or Gly (with the remaining amino acid residue(s) X being independently chosen from any naturally occurring amino acid but preferably being independently chosen from Val, Leu and/or Ile); or
(p) n=3 and at least two X=Ala or Gly (with the remaining amino acid residue(s) X being independently chosen from any naturally occurring amino acid but preferably being independently chosen from Val, Leu and/or Ile);

with aspects (a), (b), (c), (g), (h), (i), (m) and (n) being particularly preferred, with aspects in which n=1 or 2 being preferred and aspects in which n=1 being particularly preferred.

It should also be noted that, preferably, any C-terminal extension present in a serum albumin binder of the invention does not contain a (free) cysteine residue (unless said cysteine residue is used or intended for further functionalization, for example for pegylation).

Some specific, but non-limiting examples of useful C-terminal extensions are the following amino acid sequences: A, AA, AAA, G, GG, GGG, AG, GA, AAG, AGG, AGA, GGA, GAA or GAG.

When the serum albumin binders of the invention contain mutations at positions 110 or 112 (optionally in combination with mutations at position 11 and/or 89 as described herein), the C-terminal amino acid residues of framework 4 (starting from position 109) can be as follows: (i) if no C-terminal extension is present: VTVKS (SEQ ID NO:101), VTVQS (SEQ ID NO:102), VKVSS (SEQ ID NO:103) or VQVSS (SEQ ID NO:104); or (ii) if a C-terminal extension is present: $VTVKSX_{(n)}$ (SEQ ID NO:105), VTVQSX(n) (SEQ ID NO:106), VKVSSX(n) (SEQ ID NO:107) or $VQVSSX_{(n)}$ (SEQ ID NO:108), such as VTVKSA (SEQ ID NO: 109), VTVQSA (SEQ ID NO:110), VKVSSA (SEQ ID NO:111) or VQVSSA (SEQ ID NO:112). When the serum albumin binders of the invention do not contain mutations at positions 110 or 112 (but only mutations at position 11 and/or 89 as described herein), the C-terminal amino acid residues of framework 4 (starting from position 109) will usually be either: (i) when no C-terminal extension is present: VTVSS (SEQ ID NO:113) (as in the sequence of SEQ ID NO:3); or (ii) when a C-terminal extension is present: $VTVSSX_{(n)}$ (SEQ ID NO: 114) such as VTVSSA (SEQ ID NO:115) (as in the sequence of SEQ ID NO:4). In these C-terminal sequences, X and n are as defined herein for the C-terminal extensions.

Also, when a serum albumin binder of the invention is present at/and or forms the N-terminal end of a compound or polypeptides of the invention, then the serum albumin binder preferably has a D at position 1 (i.e. an E1D mutation compared to the sequences given of SEQ ID NOs: 1 to 4 and 16 to 99).

Also, generally, when a compound or polypeptide of the invention has a heavy-chain ISVD at its C-terminal end (which may be a serum albumin binder of the invention but for example also an ISVD binding to a therapeutic target), then said C-terminal ISVD (and by extension, the compound or polypeptide of the invention) preferably has a C-terminal extension X(n) as described herein. Similarly, when a compound or polypeptide of the invention has a heavy chain ISVD at its N-terminal end (which may be a serum albumin binder of the invention but for example also an ISVD binding to a therapeutic target), then said N-terminal ISVD (and by extension, the compound or polypeptide of the invention) preferably has a D at position 1.

Also, preferably, when a compound or polypeptide of the invention contains one or more other ISVDs besides the albumin binder(s) of the invention (which other ISVD(s) may for example be one or more ISVD's against a therapeutic target), then preferably all ISVD's present in said compound or polypeptide contain within their sequence one or more framework mutations that reduce binding by pre-existing antibodies. In particular, when these other ISVDs are Nanobodies or (single) domain antibodies that is, essentially consist of and/or is derived from a VH domain, they may contain (a suitable combination of) amino acid residues/mutations at positions 11, 89, 110 and/or 112 that are as described in PCT/EP2015/060643 and/or that essentially are as described in PCT/EP2015/060643 and/or as described herein for the albumin binders of the invention.

As mentioned, the amino acid sequences provided by the invention are proteins that can bind to, and that can in particular specifically (as described herein) bind to, human serum albumin. Thus, they can be used as binding units or binding domains for binding to (human) serum albumin, for example to confer an increase in half-life (as defined herein) to therapeutic compounds, moieties or entities. For the use of serum albumin-binding domains to increase half-life of therapeutic compounds, moieties or entities, reference is generally made to WO 2004/041865, WO 2006/122787, EP 2 139 918, WO 2011/006915, WO 2012/175400 and/or WO 2014/111550. The albumin binders of the invention can generally be used in the same way and for the same purposes as the serum albumin binders described in these references.

Some preferred but non-limiting examples of ISV's of the invention are given in SEQ ID NO's: 16 to 99, and each of these sequences forms a further aspect of the invention (as do proteins, polypeptides or other compounds or constructs that comprise one of these sequences). Of these:

- SEQ ID NO's: 16 to 29 are examples of variants of the sequence of SEQ ID NO:1. These sequences have a CDR1 (defined according to Kabat) that is the sequence of SEQ ID NO: 5; a CDR2 (defined according to Kabat) that is the sequence of SEQ ID NO: 6; and a CDR3 (defined according to Kabat) that is the sequence of SEQ ID NO: 7;
- SEQ ID NO's: 30 to 43 are examples of variants of the sequence of SEQ ID NO:1 with a C-terminal alanine (a preferred but non-limiting example of a C-terminal extension as described herein). These sequences have a CDR1 (defined according to Kabat) that is the sequence of SEQ ID NO: 5; a CDR2 (defined according to Kabat) that is the sequence of SEQ ID NO: 6; and a CDR3 (defined according to Kabat) that is the sequence of SEQ ID NO: 7;
- SEQ ID NO's: 44 to 57 are examples of variants of the sequence of SEQ ID NO:2. These sequences have a CDR1 (defined according to Kabat) that is the sequence of SEQ ID NO: 10; a CDR2 (defined according to Kabat) that is the sequence of SEQ ID NO: 11; and a CDR3 (defined according to Kabat) that is the sequence of SEQ ID NO: 12;
- SEQ ID NO's: 58 to 71 are examples of variants of the sequence of SEQ ID NO:2 with a C-terminal alanine (a preferred but non-limiting example of a C-terminal extension as described herein). These sequences have a CDR1 (defined according to Kabat) that is the sequence of SEQ ID NO: 10; a CDR2 (defined according to Kabat) that is the sequence of SEQ ID NO: 11; and a CDR3 (defined according to Kabat) that is the sequence of SEQ ID NO: 12;
- SEQ ID NO's: 72 to 85 are examples of variants of the sequence of SEQ ID NO:3. These sequences have a CDR1 (defined according to Kabat) that is the sequence of SEQ ID NO: 10; a CDR2 (defined according to Kabat) that is the sequence of SEQ ID NO: 11; and a CDR3 (defined according to Kabat) that is the sequence of SEQ ID NO: 15;
- SEQ ID NO's: 86 to 99 to 54 are examples of variants of the sequence of SEQ ID NO:4 (which is SEQ ID NO:3 with a C-terminal alanine extension). These sequences have a CDR1 (defined according to Kabat) that is the sequence of SEQ ID NO: 10; a CDR2 (defined according to Kabat) that is the sequence of SEQ ID NO: 11; and a CDR3 (defined according to Kabat) that is the sequence of SEQ ID NO: 15.

Of these variants, the sequences of SEQ ID NO's: 72 to 85 (when a C-terminal extension is not required) and the sequences of SEQ ID NO's: 86 to 99 (when a C-terminal extension is required) are most preferred.

Thus, in a first aspect, the invention relates to an immunoglobulin single variable domain having:
- a CDR1 (according to Kabat) that is chosen from the following sequences: TGEMA (SEQ ID NO: 5) and TSSML (SEQ ID NO:10) and that is preferably TSSML (SEQ ID NO:10); and
- a CDR2 (according to Kabat) that is chosen from the following sequences: SISSSGATTYYADSVKG (SEQ ID NO:6) and VIHQSGTPTYYADSVKG (SEQ ID NO: 11) and that is preferably VIHQSGTPTYYADSVKG (SEQ ID NO: 11); and
- a CDR3 (according to Kabat) that is chosen from the following sequences: PRHPQGGVTFDY (SEQ ID NO:7), FPSTHGKFDY (SEQ ID NO:12) and and having:
- a degree of sequence identity with the amino acid sequence of SEQ ID NO:1 (in which any C-terminal extension that may be present as well as the CDRs are not taken into account for determining the degree of sequence identity) of at least 85%, preferably at least 90%, more preferably at least 95%;

and/or
- no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:1 (in which said amino acid differences, if present, may be present in the frameworks and/or the CDR's but are preferably present only in the frameworks and not in the CDRs);

and optionally having (in particular, when the ISVD is present at and/or forms the C-terminal end of a compound or polypeptide of the invention):
- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally having (in particular, when the ISVD is present at and/or forms the N-terminal end of a compound or polypeptide of the invention) a D and/or E1D mutation at position 1; in which:
- the amino acid residue at position 11 is preferably chosen from L or V; and
- the amino acid residue at position 89 is preferably suitably chosen from T, V or L; and
- the amino acid residue at position 110 is preferably suitably chosen from T, K or Q; and
- the amino acid residue at position 112 is preferably suitably chosen from S, K or Q;

such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (vii) position 11 is V and position 112 is K or Q.

In a further aspect, the invention relates to an immunoglobulin single variable domain having:
- a CDR1 (according to Kabat) that is chosen from the following sequences: TGEMA (SEQ ID NO: 5) and TSSML (SEQ ID NO:10) and that is preferably TSSML (SEQ ID NO:10); and a CDR2 (according to Kabat) that is chosen from the following sequences: SISSSGATTYYADSVKG (SEQ ID NO:6) and VIHQSGTPTYYADSVKG (SEQ ID NO:11) and that is preferably VIHQSGTPTYY-ADSVKG (SEQ ID NO: 11); and a CDR3 (according to Kabat) that is chosen from the following sequences: PRHPQGGVTFDY (SEQ ID NO:7), FPSTHGKFDY (SEQ ID NO:12) and FPSSRMKFDY (SEQ ID NO: 15) and that is preferably FPSTHGKFDY (SEQ ID NO: 12) or FPSSRMKFDY (SEQ ID NO: 15) and most preferably FPSSRMKFDY (SEQ ID NO:15);

and having:

a degree of sequence identity with one of the sequences of SEQ ID NO's: 1 to 4 (in which any C-terminal extension that may be present as well as the CDRs are not taken into account for determining the degree of sequence identity) of at least 85%, preferably at least 90%, more preferably at least 95%; and in particular a degree of sequence identity with the sequence SEQ ID NO: 3 or 4 (in which again any C-terminal extension that may be present as well as the CDRs are not taken into account for determining the degree of sequence identity) of at least 85%, preferably at least 90%, more preferably at least 95%; and/or no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with one of the sequences of SEQ ID NO's: 1 to 4 (in which said amino acid differences, if present, may be present in the frameworks and/or the CDR's but are preferably present only in the frameworks and not in the CDRs); and in particular no more than 5, preferably no more than 3, such as only 3, 2 or 1 such amino acid differences with the sequence of SEQ ID NO: 3 or SEQ ID NO:4 (in which said amino acid differences, if present, may be present in the frameworks and/or the CDR's but are preferably present only in the frameworks and not in the CDRs);

and optionally having (in particular, when the ISVD is present at and/or forms the C-terminal end of a compound or polypeptide of the invention):

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally having (in particular, when the ISVD is present at and/or forms the N-terminal end of a compound or polypeptide of the invention) a D and/or E1D mutation at position 1; which immunoglobulin single variable domain comprises the following amino acid residues (i.e. mutations compared to the sequences of SEQ ID NO's: 1 to 4) at the positions mentioned (numbering according to Kabat):

89T; or
89L in combination with 11V; or
89L in combination with 110K or 110Q; or
89L in combination with 112K or 112Q; or
89L in combination with 11V and 110K or 110Q; or
89L in combination with 11V and 112K or 112Q; or
11V in combination with 110K or 110Q; or
11V in combination with 112K or 112Q.

In particular, the serum albumin binders of the invention preferably have no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with one of the sequences of SEQ ID NO's: 1 to 4 (in which said amino acid differences, if present, may be present in the frameworks and/or the CDR's but are preferably present only in the frameworks and not in the CDRs); and in particular no more than 5, preferably no more than 3, such as only 3, 2 or 1 such amino acid differences with the sequence of SEQ ID NO: 3 (in which said amino acid differences, if present, may be present in the frameworks and/or the CDR's but are preferably present only in the frameworks and not in the CDRs).

Some specific, but non-limiting examples of such mutations/amino acid differences that may be present (i.e. compared to the sequences of SEQ ID NO's: 1 to 4) are: E1D, P14A; P41A, P41L, P41S or P41T (and in particular P41A); P42E or T87A. Other examples of mutations are (a suitable combination of) one or more suitable "camelizing" substitutions; reference is for example made to Davies and Riechmann, Protein Engineering, vol. 9, no. 6, 531-537, 1996 and Davies and Riechmann, FEBS Letters 399 (1004), 285-290, as well as Tables A-3 to A-8 from WO 08/020079.

As mentioned, in the invention, amino acid sequences in which position 89 is T or in which position 11 is V and position 89 is L (optionally in suitable combination with a 110K or 110Q mutation and/or a 112K or 112Q mutation, and in particular in combination with a 110K or 110Q mutation) are particularly preferred. Even more preferred are amino acid sequences in which position 11 is V and position 89 is L, optionally with a 110K or 110Q mutation.

Thus, in one preferred aspect, the invention relates to an immunoglobulin single variable domain having:

a CDR1 (according to Kabat) that is chosen from the following sequences: TGEMA (SEQ ID NO: 5) and TSSML (SEQ ID NO:10) and that is preferably TSSML (SEQ ID NO:10); and a CDR2 (according to Kabat) that is chosen from the following sequences: SISSSGATTYYADSVKG (SEQ ID NO:6) and VIHQSGTPTYYADSVKG (SEQ ID NO: 11) and that is preferably VIHQSGTPTYY-ADSVKG (SEQ ID NO: 11); and a CDR3 (according to Kabat) that is chosen from the following sequences: PRHPQGGVTFDY (SEQ ID NO:7), FPSTHGKFDY (SEQ ID NO:12) and FPSSRMKFDY (SEQ ID NO:15) and that is preferably FPSTHGKFDY (SEQ ID NO:12) or FPSSRMKFDY (SEQ ID NO: 15) and most preferably FPSSRMKFDY (SEQ ID NO:15);

and having:

a degree of sequence identity with the amino acid sequence of SEQ ID NO:1 (in which any C-terminal extension that may be present as well as the CDRs are not taken into account for determining the degree of sequence identity) of at least 85%, preferably at least 90%, more preferably at least 95%;

and/or no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:1 (in which said amino acid differences, if present, may be present in the frameworks and/or the CDR's but are preferably present only in the frameworks and not in the CDRs);

and optionally having (in particular, when the ISVD is present at and/or forms the C-terminal end of a compound or polypeptide of the invention):

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally having (in particular, when the ISVD is present at and/or forms the N-terminal end of a compound or polypeptide of the invention) a D and/or E1D mutation at position 1; in which:

the amino acid residue at position 11 is preferably chosen from L or V; and the amino acid residue at position 89 is T; and the amino acid residue at position 110 is preferably suitably chosen from T, K or Q (and is preferably T); and the amino acid residue at position 112 is preferably suitably chosen from S, K or Q (and in preferably S).

In another preferred aspect, the invention relates to an immunoglobulin single variable domain having:

a CDR1 (according to Kabat) that is chosen from the following sequences: TGEMA (SEQ ID NO: 5) and TSSML (SEQ ID NO:10) and that is preferably TSSML (SEQ ID NO:10); and a CDR2 (according to Kabat) that is chosen from the following sequences: SISSSGATTYYADSVKG (SEQ ID NO:6) and VIHQSGTPTYYADSVKG (SEQ ID NO: 11) and that is preferably VIHQSGTPTYY-ADSVKG (SEQ ID NO: 11); and a CDR3 (according to Kabat) that is chosen from the following sequences: PRHPQGGVTFDY (SEQ ID NO:7), FPSTHGKFDY (SEQ ID NO:12) and FPSSRMKFDY (SEQ ID NO:15) and that is preferably FPSTHGKFDY (SEQ ID NO:12) or FPSSRMKFDY (SEQ ID NO: 15) and most preferably FPSSRMKFDY (SEQ ID NO:15);

and having:

a degree of sequence identity with the amino acid sequence of SEQ ID NO:1 (in which any C-terminal extension that may be present as well as the CDRs are not taken into account for determining the degree of sequence identity) of at least 85%, preferably at least 90%, more preferably at least 95%;

and/or no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:1 (in which said amino acid differences, if present, may be present in the frameworks and/or the CDR's but are preferably present only in the frameworks and not in the CDRs);

and optionally having (in particular, when the ISVD is present at and/or forms the C-terminal end of a compound or polypeptide of the invention):

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally having (in particular, when the ISVD is present at and/or forms the N-terminal end of a compound or polypeptide of the invention) a D and/or E1D mutation at position 1; in which:

the amino acid residue at position 11 is V; and the amino acid residue at position 89 is L; and the amino acid residue at position 110 is preferably suitably chosen from T, K or Q; and the amino acid residue at position 112 is preferably suitably chosen from S, K or Q.

In a specific, but non-limiting aspect, the serum albumin binders of the invention have:

a CDR1 (according to Kabat) that is TSSML (SEQ ID NO: 10); and a CDR2 (according to Kabat) that is VIHQSGTPTYY-ADSVKG (SEQ ID NO: 11); and a CDR3 (according to Kabat) that is chosen from the following sequences: FPSTHGKFDY (SEQ ID NO:12) or FPSSRMKFDY (SEQ ID NO:15) and that is preferably FPSSRMKFDY (SEQ ID NO: 15);

and more in particular:

a CDR1 (according to Kabat) that is TSSML (SEQ ID NO:10); and a CDR2 (according to Kabat) that is VIHQSGTPTYY-ADSVKG (SEQ ID NO: 11); and a CDR3 (according to Kabat) that is FPSSRMKFDY (SEQ ID NO:15).

In one specific, but non-limiting aspect, the serum albumin binders of the invention comprise the following amino acid residues (i.e. mutations compared to the sequences of SEQ ID NO's: 1 to 4) at the positions mentioned (numbering according to Kabat):

11V in combination with 89L; or 11V in combination with 110K or 110Q;

11V in combination with 112K or 112Q;

11V in combination with 89L and 110K or 110Q; or 11V in combination with 89L and 112K or 112Q;

and have CDR's and have an overall degree of sequence identity with the reference sequences that are as described herein.

In another specific, but non-limiting aspect, the serum albumin binders of the invention comprise the following amino acid residues (i.e. mutations compared to the sequences of SEQ ID NO's: 1 to 4) at the positions mentioned (numbering according to Kabat):

89L in combination with 11V; or 89L in combination with 110K or 110Q; or 89L in combination with 112K or 112Q; or 89L in combination with 11V and 110K or 110Q; or 89L in combination with 11V and 112K or 112Q;

and have CDR's and have an overall degree of sequence identity with the reference sequences that are as described herein.

In another specific, but non-limiting aspect, the serum albumin binders of the invention comprise the following amino acid residues (i.e. mutations compared to the sequences of SEQ ID NO's: 1 to 4) at the positions mentioned (numbering according to Kabat):

110K or 110Q in combination with 11V; or
110K or 110Q in combination with 89L; or
110K or 110Q in combination with 11V and 89L;

and have CDR's and have an overall degree of sequence identity with the reference sequences that are as described herein.

In another specific, but non-limiting aspect, the serum albumin binders of the invention comprise the following amino acid residues (i.e. mutations compared to the sequences of SEQ ID NO's: 1 to 4) at the positions mentioned (numbering according to Kabat):

112K or 112Q in combination with 11V; or
112K or 112Q in combination with 89L; or
112K or 112Q in combination with 11V and 89L;

and have CDR's and have an overall degree of sequence identity with the reference sequences that are as described herein.

In another specific, but non-limiting aspect, the serum albumin binders of the invention comprise a T at position 89 and have CDR's and have an overall degree of sequence identity with the reference sequences that are as described herein.

In another specific, but non-limiting aspect, the serum albumin binders of the invention comprise an V at position 11 and an L at position 89 and have CDR's and have an overall degree of sequence identity with the reference sequences that are as described herein.

In another aspect, the invention relates to an immunoglobulin single variable domain having:

a CDR1 (according to Abm) that is chosen from the following sequences: GFTFSTGEMA (SEQ ID NO: 8) and GFTFDTSSML (SEQ ID NO: 13) and that is preferably GFTFDTSSML (SEQ ID NO:13); and a CDR2 (according to Abm) that is chosen from the following sequences: SISSSGATTY (SEQ ID NO:9) and VIHQSGTPTY (SEQ ID NO:14) and that is preferably VIHQSGTPTY (SEQ ID NO:14); and a CDR3 (according to Abm) that is chosen from the following sequences: PRHPQGGVTFDY (SEQ ID NO:7), FPSTHGKFDY (SEQ ID NO: 12) and FPSSRMKFDY (SEQ ID NO: 15) and that is preferably FPSTHGKFDY (SEQ ID NO: 12) or FPSSRMKFDY (SEQ ID NO: 15) and that is most preferably FPSSRMKFDY (SEQ ID NO: 15);

and having:

a degree of sequence identity with the amino acid sequence of SEQ ID NO:1 (in which any C-terminal extension that may be present as well as the CDRs are not taken into account for determining the degree of sequence identity) of at least 85%, preferably at least 90%, more preferably at least 95%;

and/or no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:1 (in which said amino acid differences, if present, may be present in the frameworks and/or the CDR's but are preferably present only in the frameworks and not in the CDRs);

and optionally having (in particular, when the ISVD is present at and/or forms the C-terminal end of a compound or polypeptide of the invention):

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally having (in particular, when the ISVD is present at and/or forms the N-terminal end of a compound or polypeptide of the invention) a D and/or E1D mutation at position 1; in which:

the amino acid residue at position 11 is preferably chosen from L or V; and
the amino acid residue at position 89 is preferably suitably chosen from T, V or L; and
the amino acid residue at position 110 is preferably suitably chosen from T, K or Q; and
the amino acid residue at position 112 is preferably suitably chosen from S, K or Q;

such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (vii) position 11 is V and position 112 is K or Q.

In another aspect, the invention relates to an immunoglobulin single variable domain having:

a CDR1 (according to Abm) that is chosen from the following sequences: GFTFSTGEMA (SEQ ID NO: 8) and GFTFDTSSML (SEQ ID NO:13) and that is preferably GFTFDTSSML (SEQ ID NO:13); and a CDR2 (according to Abm) that is chosen from the following sequences: SISSSGATTY (SEQ ID NO:9) and VIHQSGTPTY (SEQ ID NO:14) and that is preferably VIHQSGTPTY (SEQ ID NO:14); and a CDR3 (according to Abm) that is chosen from the following sequences: PRHPQGGVTFDY (SEQ ID NO:7), FPSTHGKFDY (SEQ ID NO: 12) and FPSSRMKFDY (SEQ ID NO: 15) and that is preferably FPSTHGKFDY (SEQ ID NO: 12) or FPSSRMKFDY (SEQ ID NO: 15) and that is most preferably FPSSRMKFDY (SEQ ID NO: 15);

and having:

a degree of sequence identity with one of the sequences of SEQ ID NO's: 1 to 4 (in which any C-terminal extension that may be present as well as the CDRs are not taken into account for determining the degree of sequence identity) of at least 85%, preferably at least 90%, more preferably at least 95%; and in particular a degree of sequence identity with the sequence SEQ ID NO: 3 or 4 (in which again any C-terminal extension that may be present as well as the CDRs are not taken into account for determining the degree of sequence identity) of at least 85%, preferably at least 90%, more preferably at least 95%; and/or no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with one of the sequences of SEQ ID NO's: 1 to 4 (in which said amino acid differences, if present, may be present in the frameworks and/or the CDR's but are preferably present only in the frameworks and not in the CDRs); and in particular no more than 5, preferably no more than 3, such as only 3, 2 or 1 such amino acid differences with the sequence of SEQ ID NO: 3 or SEQ ID NO:4 (in which said amino acid differences, if present, may be present in the frameworks and/or the CDR's but are preferably present only in the frameworks and not in the CDRs);

and optionally having (in particular, when the ISVD is present at and/or forms the C-terminal end of a compound or polypeptide of the invention):

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally having (in particular, when the ISVD is present at and/or forms the N-terminal end of a compound or polypeptide of the invention) a D and/or E1D mutation at position 1; which immunoglobulin single variable domain comprises the following amino acid residues (i.e. mutations compared to the sequences of SEQ ID NOs: 1 to 4) at the positions mentioned (numbering according to Kabat):

89T; or
89L in combination with 11V; or
89L in combination with 110K or 110Q; or
89L in combination with 112K or 112Q; or
89L in combination with 11V and 110K or 110Q; or
89L in combination with 11V and 112K or 112Q; or
11V in combination with 110K or 110Q; or
11V in combination with 112K or 112Q.

In particular, the serum albumin binders of the invention preferably have no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with one of the sequences of SEQ ID NO's: 1 to 4 (in which said amino acid differences, if present, may be present in the frameworks and/or the CDR's but are preferably present only in the frameworks and not in the CDRs); and in particular no more than 5, preferably no more than 3, such as only 3, 2 or 1 such amino acid differences with the sequence of SEQ ID NO: 3 (in which said amino acid differences, if present, may be present in the frameworks and/or the CDR's but are preferably present only in the frameworks and not in the CDRs).

As mentioned, in the invention, amino acid sequences in which position 89 is T or in which position 11 is V and position 89 is L (optionally in suitable combination with a 110K or 110Q mutation and/or a 112K or 112Q mutation, and in particular in combination with a 110K or 110Q mutation) are particularly preferred. Even more preferred are amino acid sequences in which position 11 is V and position 89 is L, optionally with a 110K or 110Q mutation.

Thus, in one preferred aspect, the invention relates to an immunoglobulin single variable domain having:

a CDR1 (according to Abm) that is chosen from the following sequences: GFTFSTGEMA (SEQ ID NO: 8) and GFTFDTSSML (SEQ ID NO:13) and that is preferably GFTFDTSSML (SEQ ID NO:13); and a CDR2 (according to Abm) that is chosen from the following sequences: SISSSGATTY (SEQ ID NO:9) and VIHQSGTPTY (SEQ ID NO:14) and that is preferably VIHQSGTPTY (SEQ ID NO:14); and a CDR3 (according to Abm) that is chosen from the following sequences: PRHPQGGVTFDY (SEQ ID NO:7), FPSTHGKFDY (SEQ ID NO: 12) and FPSSRMKFDY (SEQ ID NO: 15) and that is preferably FPSTHGKFDY (SEQ ID NO: 12) or FPSSRMKFDY (SEQ ID NO: 15) and that is most preferably FPSSRMKFDY (SEQ ID NO: 15);

and having:

a degree of sequence identity with the amino acid sequence of SEQ ID NO:1 (in which any C-terminal extension that may be present as well as the CDRs are not taken into account for determining the degree of sequence identity) of at least 85%, preferably at least 90%, more preferably at least 95%;

and/or no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:1 (in which said amino acid differences, if present, may be present in the frameworks and/or the CDR's but are preferably present only in the frameworks and not in the CDRs);

and optionally having (in particular, when the ISVD is present at and/or forms the C-terminal end of a compound or polypeptide of the invention):

a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally having (in particular, when the ISVD is present at and/or forms the N-terminal end of a compound or polypeptide of the invention) a D and/or E1D mutation at position 1; in which:

the amino acid residue at position 11 is preferably chosen from L or V; and the amino acid residue at position 89 is T; and the amino acid residue at position 110 is preferably suitably chosen from T, K or Q (and is preferably T); and the amino acid residue at position 112 is preferably suitably chosen from S, K or Q (and in preferably S).

In another preferred aspect, the invention relates to an immunoglobulin single variable domain having:

a CDR1 (according to Abm) that is chosen from the following sequences: GFTFSTGEMA (SEQ ID NO: 8) and GFTFDTSSML (SEQ ID NO:13) and that is preferably GFTFDTSSML (SEQ ID NO:13); and a CDR2 (according to Abm) that is chosen from the following sequences: SISSSGATTY (SEQ ID NO:9) and VIHQSGTPTY (SEQ ID NO:14) and that is preferably VIHQSGTPTY (SEQ ID NO:14); and a CDR3 (according to Abm) that is chosen from the following sequences: PRHPQGGVTFDY (SEQ ID NO:7), FPSTHGKFDY (SEQ ID NO: 12) and FPSSRMKFDY (SEQ ID NO: 15) and that is preferably FPSTHGKFDY (SEQ ID NO: 12) or FPSSRMKFDY (SEQ ID NO: 15) and that is most preferably FPSSRMKFDY (SEQ ID NO: 15);

and having:
- a degree of sequence identity with the amino acid sequence of SEQ ID NO:1 (in which any C-terminal extension that may be present as well as the CDRs are not taken into account for determining the degree of sequence identity) of at least 85%, preferably at least 90%, more preferably at least 95%;

and/or
- no more than 7, such as no more than 5, preferably no more than 3, such as only 3, 2 or 1 "amino acid differences" (as defined herein, and not taking into account any of the above-listed mutations at position(s) 11, 89, 110 or 112 that may be present and not taking into account any C-terminal extension that may be present) with the amino acid sequence of SEQ ID NO:1 (in which said amino acid differences, if present, may be present in the frameworks and/or the CDR's but are preferably present only in the frameworks and not in the CDRs);

and optionally having (in particular, when the ISVD is present at and/or forms the C-terminal end of a compound or polypeptide of the invention):
- a C-terminal extension $(X)_n$, in which n is 1 to 10, preferably 1 to 5, such as 1, 2, 3, 4 or 5 (and preferably 1 or 2, such as 1); and each X is an (preferably naturally occurring) amino acid residue that is independently chosen, and preferably independently chosen from the group consisting of alanine (A), glycine (G), valine (V), leucine (L) or isoleucine (I);

and optionally having (in particular, when the ISVD is present at and/or forms the N-terminal end of a compound or polypeptide of the invention) a D and/or E1D mutation at position 1; in which:
- the amino acid residue at position 11 is V; and
- the amino acid residue at position 89 is L; and
- the amino acid residue at position 110 is preferably suitably chosen from T, K or Q; and
- the amino acid residue at position 112 is preferably suitably chosen from S, K or Q.

In a specific, but non-limiting aspect, the serum albumin binders of the invention have:
- a CDR1 (according to Abm) that is GFTFDTSSML (SEQ ID NO:13); and
- a CDR2 (according to Abm) that is VIHQSGTPTY (SEQ ID NO: 14); and
- a CDR3 (according to Abm) that is chosen from the following sequences: FPSTHGKFDY (SEQ ID NO: 12) or FPSSRMKFDY (SEQ ID NO: 15) and that is preferably FPSSRMKFDY (SEQ ID NO: 15).

and more in particular:
- a CDR1 (according to Abm) that is GFTFDTSSML (SEQ ID NO:13); and
- a CDR2 (according to Abm) that is VIHQSGTPTY (SEQ ID NO:14); and
- a CDR3 (according to Abm) that is FPSSRMKFDY (SEQ ID NO: 15).

In one specific, but non-limiting aspect, the serum albumin binders of the invention comprise the following amino acid residues (i.e. mutations compared to the sequences of SEQ ID NO's: 1 to 4) at the positions mentioned (numbering according to Kabat):
- 11V in combination with 89L; or
- 11V in combination with 110K or 110Q;
- 11V in combination with 112K or 112Q;
- 1V in combination with 89L and 110K or 110Q; or
- 11V in combination with 89L and 112K or 112Q;

and have CDR's and have an overall degree of sequence identity with the reference sequences that are as described herein.

In another specific, but non-limiting aspect, the serum albumin binders of the invention comprise the following amino acid residues (i.e. mutations compared to the sequences of SEQ ID NO's: 1 to 4) at the positions mentioned (numbering according to Kabat):
- 89L in combination with 11V; or
- 89L in combination with 110K or 110Q; or
- 89L in combination with 112K or 112Q; or
- 89L in combination with 11V and 110K or 110Q; or
- 89L in combination with 11V and 112K or 112Q;

and have CDR's and have an overall degree of sequence identity with the reference sequences that are as described herein.

In another specific, but non-limiting aspect, the serum albumin binders of the invention comprise the following amino acid residues (i.e. mutations compared to the sequences of SEQ ID NO's: 1 to 4) at the positions mentioned (numbering according to Kabat):
- 110K or 110Q in combination with 11V; or
- 110K or 110Q in combination with 89L; or
- 110K or 110Q in combination with 11V and 89L;

and have CDR's and have an overall degree of sequence identity with the reference sequences that are as described herein.

In another specific, but non-limiting aspect, the serum albumin binders of the invention comprise the following amino acid residues (i.e. mutations compared to the sequences of SEQ ID NO's: 1 to 4) at the positions mentioned (numbering according to Kabat):
- 112K or 112Q in combination with 11V; or
- 112K or 112Q in combination with 89L; or
- 112K or 112Q in combination with 1V and 89L;

and have CDR's and have an overall degree of sequence identity with the reference sequences that are as described herein.

In another specific, but non-limiting aspect, the serum albumin binders of the invention comprise the following amino acid residues (i.e. mutations compared to the sequences of SEQ ID NO's: 1 to 4) at the positions mentioned (numbering according to Kabat):
- 89T;

and have CDR's and have an overall degree of sequence identity with the reference sequences that are as described herein.

In another specific, but non-limiting aspect, the invention relates to an immunoglobulin single variable domain having an amino acid sequence that is chosen from the amino acid sequences of SEQ ID NO's: 16 to 99.

In another specific, but non-limiting aspect, the invention relates to an immunoglobulin single variable domain having an amino acid sequence that is chosen from the amino acid sequences of SEQ ID NO's: 44 to 99.

In another specific, but non-limiting aspect, the invention relates to an immunoglobulin single variable domain having an amino acid sequence that is one of the following sequences: SEQ ID NO:72, SEQ ID NO:73, SEQ ID NO:74, SEQ ID NO:75, SEQ ID NO:76, SEQ ID NO:77, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:97, SEQ ID NO:98 or SEQ ID NO:99.

In another specific, but non-limiting aspect, the invention relates to an immunoglobulin single variable domain having an amino acid sequence that is one of the following sequences: SEQ ID NO: 50, SEQ ID NO: 64, SEQ ID NO: 78 or SEQ ID NO: 92, and preferably SEQ ID NO: 78 or SEQ ID NO: 92.

The invention also relates to proteins, polypeptides and other constructs, molecules or chemical entities that comprise or essentially consist of (one or more of) the serum albumin binders of the invention as described herein; to methods for expressing/producing the improved heavy-chain immunoglobulin variable domains of the invention and/or for expressing/producing proteins, polypeptides and other constructs, molecules or chemical entities comprising the same; to compositions and products (such as pharmaceutical compositions and products) that comprise the improved heavy-chain immunoglobulin variable domains of the invention and/or proteins, polypeptides and other constructs, molecules or chemical entities comprising the same; to nucleotide sequence and nucleic acids that encode the improved heavy-chain immunoglobulin variable domains of the invention and/or that encode proteins or polypeptides comprising the same; and to uses (and in particular therapeutic, prophylactic and diagnostic uses) of the improved heavy-chain immunoglobulin variable domains of the invention and of proteins, polypeptides and other constructs, molecules or chemical entities comprising the same.

Further aspects, embodiments, advantages, applications and uses of the invention will become clear from the further description herein.

In the present specification:

the term "immunoglobulin single variable domain" (also referred to as "ISV" or "ISVD") is generally used to refer to immunoglobulin variable domains (which may be heavy chain or light chain domains, including VH, VHH or VL domains) that can form a functional antigen binding site without interaction with another variable domain (e.g. without a VH/VL interaction as is required between the VH and VL domains of conventional 4-chain monoclonal antibody). Examples of ISVDs will be clear to the skilled person and for example include Nanobodies (including a VHH, a humanized VHH and/or a camelized VHs such as camelized human VH's), IgNAR, domains, (single domain) antibodies (such as dAb's™) that are VH domains or that are derived from a VH domain and (single domain) antibodies (such as dAb's™) that are VL domains or that are derived from a VL domain. Unless explicitly mentioned otherwise herein, ISVDs that are based on and/or derived from heavy chain variable domains (such as VH or VHH domains) are generally preferred. Most preferably, unless explicitly indicated otherwise herein, an ISVD will be a Nanobody.

the term "Nanobody" is generally as defined in WO 2008/020079 or WO 2009/138519, and thus in a specific aspect generally denotes a VHH, a humanized VHH or a camelized VH (such as a camelized human VH) or generally a sequence optimized VHH (such as e.g. optimized for chemical stability and/or solubility, maximum overlap with known human framework regions and maximum expression). It is noted that the terms Nanobody or Nanobodies are registered trademarks of Ablynx N.V. and thus may also be referred to as Nanobody® and/or Nanobodies®);

Generally, unless indicated otherwise herein, the ISVD's, Nanobodies, polypeptides, proteins and other compounds and constructs referred to herein will be intended for use in prophylaxis or treatment of diseases or disorders in man (and/or optionally also in warm-blooded animals and in particular mammals). Thus, generally, the ISVD's, Nanobodies, polypeptides, proteins and other compounds and constructs described herein are preferably such that they can be used as, and/or can suitably be a part of, a (biological) drug or other pharmaceutically or therapeutically active compound and/or of a pharmaceutical product or composition. Such a drug, compound or product is preferably such that it is suitable for administration to a human being, e.g. for prophylaxis or treatment of a subject in need of such prophylaxis or treatment or for example as part of a clinical trial. As further described herein, for this purpose, such a drug or compound may contain other moieties, entities or binding units besides the ISVDs provided by the invention (which, as also described herein, may for example be one or more other further therapeutic moieties and/or one or more other moieties that influence the pharmacokinetic or pharmacodynamic properties of the ISVD-based or Nanobody-based biological, such as its half-life). Suitable examples of such further therapeutic or other moieties will be clear to the skilled person, and for example generally can include any therapeutically active protein, polypeptide or other binding domain or binding unit, as well as for example modifications such as those described on pages 149 to 152 of WO 2009/138159. An ISVD-based biological or Nanobody-based biological is preferably a therapeutic or intended for use as a therapeutic (which includes prophylaxis and diagnosis) and for this purpose preferably contains at least one ISVD against a therapeutically relevant target (such as for example RANK-L, vWF, IgE, RSV, CXCR4, IL-23 or other interleukins, etc.). For some specific but non-limiting examples of such ISVD-based or Nanobody-based biologicals, reference is to Examples 8 to 18 and also for example made to the various applications by Ablynx N.V. (such as for example and without limitation WO 2004/062551, WO 2006/122825, WO 2008/020079 and WO 2009/068627), as well as for example (and without limitation) to applications such as WO 2006/038027, WO 2006/059108, WO 2007/063308, WO 2007/063311, WO 2007/066016 and WO 2007/085814. Also, as further described herein, the further moiety may be an ISVD or Nanobody as described herein directed against a (human) serum protein such as (human) serum albumin, and such an ISVD or Nanobody may also find therapeutic uses, in particular in and/or for extending the half-life of the TNF binders described herein. Reference is for example made to WO 2004/041865, WO 2006/122787 and WO 2012/175400, which generally describe the use of serum-albumin binding Nanobodies for half-life extension. Also, in the present specification, unless explicitly mentioned otherwise herein, all terms mentioned herein have the meaning given in WO 2009/138519 (or in the prior art cited in WO 2009/138519) or WO 2008/020079 (or in the prior art cited in WO 2008/020079). Also, where a method or technique is not specifically described herein, it can be performed as described in WO 2009/138519 (or in the prior art cited in WO 2009/138519) or WO 2008/020079 (or in the prior art cited in WO 2008/020079). Also, as described herein, any pharmaceutical product or composition comprising any ISVD or compound of the invention may also comprise one or more further components known per se for use in pharmaceutical products or compositions (i.e. depending on the intended pharmaceutical form) and/or for example one or more other compounds or active principles intended for therapeutic use (i.e. to provide a combination product).

Also, when used in the present specification or claims, the following terms have the same meaning as given on, and/or where applicable can be determined in the manner described in, pages 62-75 of WO 2009/138519: "agonist", "antagonist", "inverse agonist", "non-polar, uncharged amino acid residue", "polar uncharged amino acid residue", "polar, charged amino acid residue", "sequence identity", "exactly the same" and "amino acid difference" (when referring to a sequence comparison of two amino acid sequences), "(in) essentially isolated (form)", "domain", "binding domain", "antigenic determinant", "epitope", "against" or "directed against" (an antigen), "specificity" and "half-life". In addition, the terms "modulating" and "to modulate", "interaction site", "specific for", "cross-block", "cross-blocked" and "cross-blocking" and "essentially independent of the pH" are as defined on (and/or can be determined as described on) pages 74-79 of WO 2010/130832 of Ablynx N.V. Also, when referring to a construct, compound, protein or polypeptide of the invention, terms like "monovalent", "bivalent" (or "multivalent"), "bispecific" (or "multispecific"), and "biparatopic" (or "multiparatopic") may have the meaning given in WO 2009/138519, WO 2010/130832 or WO 2008/020079.

The term "half-life" as used here in relation to an ISVD, Nanobody, ISVD-based biological, Nanobody-based biological or any other amino acid sequence, compound or polypeptide referred to herein can generally be defined as described in paragraph o) on page 57 of WO 2008/020079 and as mentioned therein refers to the time taken for the serum concentration of the amino acid sequence, compound or polypeptide to be reduced by 50%, in vivo, for example due to degradation of the sequence or compound and/or clearance or sequestration of the sequence or compound by natural mechanisms. The in vivo half-life of an amino acid sequence, compound or polypeptide of the invention can be determined in any manner known per se, such as by pharmacokinetic analysis. Suitable techniques will be clear to the person skilled in the art, and may for example generally be as described in paragraph o) on page 57 of WO 2008/020079. As also mentioned in paragraph o) on page 57 of WO 2008/020079, the half-life can be expressed using parameters such as the t1/2-alpha, t1/2-beta and the area under the curve (AUC). In this respect it should be noted that the term "half-life" as used herein in particular refers to the t1/2-beta or terminal half-life (in which the t1/2-alpha and/or the AUC or both may be kept out of considerations). Reference is for example made to the Experimental Part below, as well as to the standard handbooks, such as Kenneth, A et al: Chemical Stability of Pharmaceuticals: A Handbook for Pharmacists and Peters et al, Pharmacokinetic analysis: A Practical Approach (1996). Reference is also made to "Pharmacokinetics", M Gibaldi & D Perron, published by Marcel Dekker, 2nd Rev. edition (1982). Similarly, the terms "increase in half-life" or "increased half-life" are also as defined in paragraph o) on page 57 of WO 2008/020079 and in particular refer to an increase in the t1/2-beta, either with or without an increase in the t1/2-alpha and/or the AUC or both.

When a term is not specifically defined herein, it has its usual meaning in the art, which will be clear to the skilled person. Reference is for example made to the standard handbooks, such as Sambrook et al, "Molecular Cloning: A Laboratory Manual" (2nd. Ed.), Vols. 1-3, Cold Spring Harbor Laboratory Press (1989); F. Ausubel et al, eds., "Current protocols in molecular biology", Green Publishing and Wiley Interscience, New York (1987); Lewin, "Genes II", John Wiley & Sons, New York, N.Y., (1985); Old et al., "Principles of Gene Manipulation: An Introduction to Genetic Engineering", 2nd edition, University of California Press, Berkeley, Calif. (1981); Roitt et al., "Immunology" (6th. Ed.), Mosby/Elsevier, Edinburgh (2001); Roitt et al., Roitt's Essential Immunology, 10th Ed. Blackwell Publishing, U K (2001); and Janeway et al., "Immunobiology" (6th Ed.), Garland Science Publishing/Churchill Livingstone, New York (2005), as well as to the general background art cited herein.

Also, as already indicated herein, the amino acid residues of a Nanobody are numbered according to the general numbering for VHs given by Kabat et al. ("Sequence of proteins of immunological interest", US Public Health Services, NIH Bethesda, Md., Publication No. 91), as applied to VHH domains from Camelids in the article of Riechmann and Muyldermans, J. Immunol. Methods 2000 Jun. 23; 240 (1-2): 185-195; or referred to herein. According to this numbering, FR1 of a Nanobody comprises the amino acid residues at positions 1-30, CDR1 of a Nanobody comprises the amino acid residues at positions 31-35, FR2 of a Nanobody comprises the amino acids at positions 36-49, CDR2 of a Nanobody comprises the amino acid residues at positions 50-65, FR3 of a Nanobody comprises the amino acid residues at positions 66-94, CDR3 of a Nanobody comprises the amino acid residues at positions 95-102, and FR4 of a Nanobody comprises the amino acid residues at positions 103-113. [In this respect, it should be noted that—as is well known in the art for VH domains and for VHH domains—the total number of amino acid residues in each of the CDR's may vary and may not correspond to the total number of amino acid residues indicated by the Kabat numbering (that is, one or more positions according to the Kabat numbering may not be occupied in the actual sequence, or the actual sequence may contain more amino acid residues than the number allowed for by the Kabat numbering). This means that, generally, the numbering according to Kabat may or may not correspond to the actual numbering of the amino acid residues in the actual sequence. Generally, however, it can be said that, according to the numbering of Kabat and irrespective of the number of amino acid residues in the CDR's, position 1 according to the Kabat numbering corresponds to the start of FR1 and vice versa, position 36 according to the Kabat numbering corresponds to the start of FR2 and vice versa, position 66 according to the Kabat numbering corresponds to the start of FR3 and vice versa, and position 103 according to the Kabat numbering corresponds to the start of FR4 and vice versa.].

Alternative methods for numbering the amino acid residues of VH domains, which methods can also be applied in an analogous manner to VHH domains from Camelids and to Nanobodies, are the method described by Chothia et al. (Nature 342, 877-883 (1989)), the so-called "AbM definition" and the so-called "contact definition". However, in the present description, aspects and figures, the numbering according to Kabat as applied to VHH domains by Riechmann and Muyldermans will be followed, unless indicated otherwise.

It should also be noted that the Figures, any Sequence Listing and the Experimental Part/Examples are only given to further illustrate the invention and should not be interpreted or construed as limiting the scope of the invention and/or of the appended claims in any way, unless explicitly indicated otherwise herein.

As further described herein, the serum albumin binders of the invention can be used with advantage as a moiety, binding unit or fusion partner in order to increase the half-life of therapeutic moieties such as polypeptides, proteins, compounds (including, without limitation, small molecules) or other therapeutic entities.

Thus, in another aspect, the invention provides polypeptides, proteins, constructs, compounds or other chemical entities that comprise or essentially consist of a serum albumin binder of the invention and one or more other amino acid sequences, (binding) domains, binding units or other moieties or chemical entities.

In particular, the invention provides polypeptides, proteins, constructs, compounds or other chemical entities that comprise a serum albumin binder of the invention and one or more (such as one or two) therapeutic moieties (which may be the same or different, and may for example be directed against the same target or to different targets, and when they are directed to the same target may be directed towards the same or different epitopes, parts, domains or subunits of said target), suitably linked to each other either directly or via one or more suitable linkers or spacers. Such polypeptides, proteins or constructs may for example and without limitation be a fusion protein, as further described herein.

The invention further relates to therapeutic uses of such polypeptides, proteins, constructs or compounds and to pharmaceutical compositions comprising such polypeptides, proteins, constructs or compounds.

In one aspect, the at least one therapeutic moiety comprises or essentially consists of a therapeutic protein, polypeptide, compound, factor or other entity. In a preferred embodiment the therapeutic moiety is directed against a desired antigen or target, is capable of binding to a desired antigen (and in particular capable of specifically binding to a desired antigen), and/or is capable of interacting with a desired target. In another embodiment, the at least one therapeutic moiety comprises or essentially consists of a therapeutic protein or polypeptide. In a further embodiment, the at least one therapeutic moiety comprises or essentially consists of a binding domain or binding unit, such as an immunoglobulin or immunoglobulin sequence (including but not limited to a fragment of an immunoglobulin), such as an antibody or an antibody fragment (including but not limited to an ScFv fragment), or of another suitable protein scaffold, such as protein A domains (such as Affibodies™), tendamistat, fibronectin, lipocalin, CTLA-4, T-cell receptors, designed ankyrin repeats, avimers and PDZ domains (Binz et al., Nat. Biotech 2005, Vol 23:1257), and binding moieties based on DNA or RNA including but not limited to DNA or RNA aptamers (Ulrich et al., Comb Chem High Throughput Screen 2006 9(8):619-32).

In yet another aspect, the at least one therapeutic moiety comprises or essentially consists of an antibody variable domain, such as a heavy chain variable domain or a light chain variable domain.

In a preferred aspect, the at least one therapeutic moiety comprises or essentially consists of at least one immunoglobulin single variable domain, such as a domain antibody, single domain antibody, "dAb" or Nanobody (such as a VHH, a humanized VHH or a camelized VH) or an IgNAR domain.

In a specific embodiment, the at least one therapeutic moiety comprises or essentially consists of at least one monovalent Nanobody or a bivalent, multivalent, bispecific or multispecific Nanobody construct.

The polypeptides, (fusion) proteins, constructs or compounds that comprise a serum albumin binder of the invention and one or more therapeutic moieties can generally be (prepared and used) as described in the prior art cited above (such as WO 04/041865 and WO 06/122787), but with a serum albumin binder of the invention instead of the half-life increasing moieties described in said prior art.

The polypeptides, (fusion) proteins, constructs or compounds that comprise a serum albumin binder of the invention and one or more therapeutic moieties will generally and preferably have an increased half-life, compared to the therapeutic moiety or moieties per se.

Generally, the constructs or fusion proteins described herein preferably have a half-life that is at least 1.5 times, preferably at least 2 times, such as at least 5 times, for example at least 10 times or more than 20 times, greater than the half-life of the corresponding therapeutic moiety per se (as measured in either in man or a suitable animal, such as mouse or cynomolgus monkey).

Also, preferably, any such fusion protein or construct has a half-life in man that is increased with more than 1 hour, preferably more than 2 hours, more preferably of more than 6 hours, such as of more than 12 hours, compared to the half-life of the corresponding therapeutic moiety per se.

Also, preferably, any fusion protein or construct has a half-life (defined as t1/2 beta) in man that is more than 1 hour, preferably more than 2 hours, more preferably of more than 6 hours, such as of more than 12 hours, and for example of about one day, two days, one week, two weeks and up to the half-life of serum albumin in man (estimated to be around 19 days), although the latter may be less critical.

Half-life can generally be defined as the time taken for the serum concentration of the polypeptide to be reduced by 50%, in vivo, for example due to degradation of the ligand and/or clearance or sequestration of the ligand by natural mechanisms. In particular, half-life may be as defined in WO 2009/068627.

Methods for pharmacokinetic analysis and determination of half-life are familiar to those skilled in the art. Details may be found in Kenneth, A et al: Chemical Stability of Pharmaceuticals: A Handbook for Pharmacists and in Peters et al, Pharmacokinetic analysis: A Practical Approach (1996). Reference is also made to "Pharmacokinetics", M Gibaldi & D Perron, published by Marcel Dekker, 2nd revised edition (1982).

As mentioned, in one aspect, a serum albumin binder of the invention can be used to increase the half-life of (one or more) immunoglobulin single variable domains, such as domain antibodies, single domain antibodies, "dAb's", VHH's or Nanobodies (such as VHH's, humanized VHH's or camelized VH's such as camelized human VH's).

Thus, one embodiment of the invention relates to a polypeptide, construct or fusion protein that comprises a serum albumin binder of the invention and one or more (such as one or two) immunoglobulin single variable domain sequences, which are suitably linked to each other, either directly or optionally via one or more suitable linkers or spacers. As mentioned herein, each such immunoglobulin single variable domain present in such a polypeptide, construct or fusion protein may independently be a domain antibody, single domain antibody, "dAb" or Nanobody (such as a VHH, humanized VHH or camelized VH, such as a camelized human VH); and according to one specific but non-limiting aspect, at least one (and up to all) of these immunoglobulin single variable domains comprises two or three disulphide bridges.

As mentioned, when the polypeptide, construct of fusion protein has a heavy-chain ISVD at its C-terminal end (which IVSD may be a serum albumin binder of the invention or an ISVD against a therapeutic target, such as a Nanobody against a therapeutic target), then the (ISVD present at the C-terminal end of) polypeptide, construct of fusion protein preferably has a C-terminal extension at its C-terminal end. Again, said C-terminal extension will be of the formula $(X)_n$ in which n is 1 to 10, preferably 1 to 5, such as 1, 2, 3, 4 or 5 (and preferably 1 or 2, such as 1); and each X is an (preferably naturally occurring) amino acid residue that is independently chosen from naturally occurring amino acid residues (although according to preferred one aspect, it does not comprise any cysteine residues), and preferably independently chosen from the group consisting of alanine (A), glycine (G), valine (V), leucine (L) or isoleucine (I).

As mentioned, when the polypeptide, construct of fusion protein has a heavy chain ISVD at its N-terminal end (which IVSD may be a serum albumin binder of the invention or an ISVD against a therapeutic target, such as a Nanobody against a therapeutic target), then the (ISVD present at the C-terminal end of) polypeptide, construct of fusion protein preferably has a D or E1D mutation at position 1.

Thus, in another aspect, the invention relates to a protein, polypeptide or other compound that:
- comprises or essentially consists of at least one (and preferably only one) serum albumin binder of the invention and at least one (such as one, two or three) therapeutic moiety or entity (in which said serum albumin binder and the one or more therapeutic moieties or entities are suitably linked, optionally via one or more suitable linkers);
- has a heavy-chain ISVD at its C-terminal end, in which the ISVD at the C-terminal end has a C-terminal extension (X) (as further described herein);
- which protein, polypeptide or other compound may also have a heavy-chain ISVD at its N-terminal end, in which case said N-terminal ISVD end preferably has a D or an E1D at position 1.

Also, in a preferred aspect, when besides the serum albumin binder of the invention, one or more other ISVD's are present (i.e. when one or more of the therapeutic moieties present are ISVD's), then (one or more or all of) said "therapeutic" ISVD's preferably also have (a combination of) amino acid residues/mutations which reduce binding by pre-existing antibodies. When the ISVDs are heavy-chain ISVD's then these mutations may, as described in PCT/EP2015/060643, in particular be (a suitable combination of) one or more mutations at positions 11, 89, 110 and 112 that can essentially be the same kind of mutations (or combination of mutations) as described herein for the serum albumin binders of the invention. Preferably, if such a other ISVD is present at the C-terminal end, then at least said therapeutic ISVD comprises such mutations at positions 11, 89, 110 and/or 112 (i.e. in addition to a C-terminal extension as described herein).

According to one specific aspect, all therapeutic moieties present in the construct, fusion protein or polypeptide are ISVD's (i.e. ISVDs against a therapeutic target), and in particular heavy-chain ISVDs, and more in particular Nanobodies (i.e. Nanobodies against a therapeutic target).

For example and without limitation, a construct, fusion protein or polypeptide comprising a serum albumin binder of the invention may comprise:

- one copy of a serum albumin binder of the invention and one ISVD (and preferably Nanobody) against a therapeutic target; or
- one copy of a serum albumin binder of the invention and two ISVDs (and preferably two Nanobodies) against a therapeutic target (which ISVDs may be the same or different and when different may be directed against the same target, against different epitopes on the same target or against different therapeutic targets); or
- one copy of a serum albumin binder of the invention and three ISVDs (and preferably three Nanobodies) against a therapeutic target (which ISVDs may be the same or different and when different may be directed against the same target, against different epitopes on the same target or against different therapeutic targets).

Some non-limiting examples of constructs, fusion proteins or polypeptides of the invention can be schematically represented as follows, in which "[Alb]" represents a serum albumin binder of the invention, "[therapeutic moiety 1]" and "[therapeutic moiety 2]" represent the therapeutic moieties (which as mentioned may each independently be an immunoglobulin single variable domain), "-" represents a suitable linker (which is optional; suitable examples are 9GS and 35GS linkers) and the N-terminus is on the left hand side and the C-terminus is on the right hand side:

[Alb]-[therapeutic moiety 1]

[therapeutic moiety 1]-[Alb]-$X_{(n)}$

[Alb]-[therapeutic moiety 1]-[therapeutic moiety 1]

[therapeutic moiety 1]-[therapeutic moiety 1]-[Alb]-$X_{(n)}$

[therapeutic moiety 1]-[Alb]-[therapeutic moiety]

[Alb]-[therapeutic moiety 1]-[therapeutic moiety 2]

[therapeutic moiety 1]-[therapeutic moiety 2]-[Alb]-$X_{(n)}$

[therapeutic moiety 1]-[Alb]-[therapeutic moiety 2]

When the therapeutic moieties are ISVDs (and preferably Nanobodies) against a therapeutic target, preferred but non-limiting constructs, fusion proteins or polypeptides of the invention can be schematically represented as follows, in which "[Alb]" represents a serum albumin binder of the invention, "[therapeutic ISVD 1]" and "[therapeutic ISVD 2]" represent ISVDs against a therapeutic target (which ISVDs may be the same or different and when different may be directed against the same target, against different epitopes on the same target or against different therapeutic targets), "-" represents a suitable linker (which is optional), X(n) represents a C-terminal extension as described herein, and the N-terminus is on the left hand side and the C-terminus is on the right hand side:

[Alb]-[therapeutic ISVD 1]-$X_{(n)}$

[therapeutic ISVD 1]-[Alb]-$X_{(n)}$

[Alb]-[therapeutic ISVD 1]-[therapeutic ISVD 1]-$X_{(n)}$

[therapeutic ISVD 1]-[therapeutic ISVD 1]-[Alb]-$X_{(n)}$

[therapeutic ISVD 1]-[Alb]-[therapeutic ISVD 1]-$X_{(n)}$

[Alb]-[therapeutic ISVD 1]-[therapeutic ISVD 2]-
X$_{(n)}$

[therapeutic ISVD 1]-[therapeutic ISVD 2]-[Alb]-
X$_{(n)}$

[therapeutic ISVD 1]-[Alb]-[therapeutic ISVD 2]-
X$_{(n)}$

Thus, in another aspect, the invention relates to a multispecific (and in particular bispecific) Nanobody construct that comprises a serum albumin binder of the invention and at least one other Nanobody (such as one or two other Nanobodies, which may be the same or different), in which said at least one other Nanobody is preferably directed against a desired target (which is preferably a therapeutic target) and/or another Nanobody that useful or suitable for therapeutic, prophylactic and/or diagnostic purposes. Again, the serum albumin binder of the invention and the other Nanobodies may be suitably linked to each other either directly or optionally via one or more suitable linkers or spacers.

For a general description of multivalent and multispecific polypeptides containing one or more Nanobodies and their preparation, reference is also made to Conrath et al., J. Biol. Chem., Vol. 276, 10. 7346-7350, 2001; Muyldermans, Reviews in Molecular Biotechnology 74 (2001), 277-302; as well as to for example WO 96/34103, WO 99/23221, WO 04/041862, WO 2006/122786, WO 2008/020079, WO 2008/142164 or WO 2009/068627.

Some other examples of some specific multispecific and/or multivalent polypeptide of the invention can be found in the applications by Ablynx N.V. mentioned herein. In particular, for a general description of multivalent and multispecific constructs comprising at least one Nanobody against a serum protein for increasing the half-life, of nucleic acids encoding the same, of compositions comprising the same, of the preparation of the aforementioned, and of uses of the aforementioned, reference is made to the International applications WO 04/041865 and WO 06/122787 mentioned above (the serum albumin binders of the invention described herein can generally be used analogously to the half-life extending Nanobodies described therein such as Alb-8), as well as to the general description and specific examples of such constructs given in for example WO 04/041862, WO 2006/122786, WO 2008/020079, WO 2008/142164 or WO 2009/068627.

In one aspect, the invention relates to a protein, polypeptide or other compound or construct (and preferably a fusion protein) that comprises a serum albumin binder of the invention and one or more further heavy-chain ISVD's (e.g. Nanobodies or (single) domain antibodies comprising or derived from a VH domain), in which said serum albumin binder and said one or more further heavy-chain ISVD's all contain the following amino acid residues:
the amino acid residue at position 11 is preferably chosen from L or V; and
the amino acid residue at position 89 is preferably suitably chosen from T, V or L; and
the amino acid residue at position 110 is preferably suitably chosen from T, K or Q; and
the amino acid residue at position 112 is preferably suitably chosen from S, K or Q; such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (vii) position 11 is V and position 112 is K or Q.

In another aspect, the invention relates to a protein, polypeptide or other compound or construct (and preferably a fusion protein) that comprises a serum albumin binder of the invention and one or more further heavy-chain ISVD's, in which said serum albumin binder and said one or more further heavy-chain ISVD's all contain the following amino acid residues:
89T; or
89L in combination with 11V; or
89L in combination with 110K or 110Q; or
89L in combination with 112K or 112Q; or
89L in combination with 11V and 11K or 110Q; or
89L in combination with 11V and 112K or 112Q; or
11V in combination with 110K or 110Q; or
11V in combination with 112K or 112Q.

In another aspect, the invention relates to a protein, polypeptide or other compound or construct (and preferably a fusion protein) that comprises a serum albumin binder of the invention and one or more further heavy-chain ISVD's, in which said serum albumin binder and said one or more further heavy-chain ISVD's all contain the following amino acid residues:
the amino acid residue at position 11 is preferably chosen from L or V; and
the amino acid residue at position 89 is T; and
the amino acid residue at position 110 is preferably suitably chosen from T, K or Q (and is preferably T); and
the amino acid residue at position 112 is preferably suitably chosen from S, K or Q (and in preferably S).

In another aspect, the invention relates to a protein, polypeptide or other compound or construct (and preferably a fusion protein) that comprises a serum albumin binder of the invention and one or more further heavy-chain ISVD's, in which said serum albumin binder and said one or more further heavy-chain ISVD's all contain the following amino acid residues:
the amino acid residue at position 11 is V; and
the amino acid residue at position 89 is L; and
the amino acid residue at position 110 is preferably suitably chosen from T, K or Q; and
the amino acid residue at position 112 is preferably suitably chosen from S, K or Q.

In another aspect, the invention relates to a protein, polypeptide or other compound or construct (and preferably a fusion protein) that comprises a serum albumin binder of the invention and one or more further heavy-chain ISVD's, in which said serum albumin binder and said one or more further heavy-chain ISVD's all contain the following amino acid residues:
11V in combination with 89L; or
11V in combination with 110K or 110Q;
11V in combination with 112K or 112Q;
11V in combination with 89L and 110K or 110Q; or
11V in combination with 89L and 112K or 112Q.

In another aspect, the invention relates to a protein, polypeptide or other compound or construct (and preferably a fusion protein) that comprises a serum albumin binder of the invention and one or more further heavy-chain ISVD's, in which said serum albumin binder and said one or more further heavy-chain ISVD's all contain the following amino acid residues:
89L in combination with 11V; or
89L in combination with 110K or 110Q; or 89L in combination with 112K or 112Q; or 89L in combination with 11V and 110K or 110Q; or 89L in combination with 11V and 112K or 112Q.

In another aspect, the invention relates to a protein, polypeptide or other compound or construct (and preferably a fusion protein) that comprises a serum albumin binder of the invention and one or more further heavy-chain ISVD's, in which said serum albumin binder and said one or more further heavy-chain ISVD's all contain the following amino acid residues:

110K or 110Q in combination with 11V; or 110K or 110Q in combination with 89L; or 110K or 110Q in combination with 11V and 89L.

In another aspect, the invention relates to a protein, polypeptide or other compound or construct (and preferably a fusion protein) that comprises a serum albumin binder of the invention and one or more further heavy-chain ISVD's, in which said serum albumin binder and said one or more further heavy-chain ISVD's all contain the following amino acid residues:

112K or 112Q in combination with 11V; or 112K or 112Q in combination with 89L; or 112K or 112Q in combination with 11V and 89L.

In another aspect, the invention relates to a protein, polypeptide or other compound or construct (and preferably a fusion protein) that comprises a serum albumin binder of the invention and one or more further heavy-chain ISVD's, in which said serum albumin binder and said one or more further heavy-chain ISVD's all contain a T at position 89.

In another aspect, the invention relates to a protein, polypeptide or other compound or construct (and preferably a fusion protein) that comprises a serum albumin binder of the invention and one or more further heavy-chain ISVD's, in which said serum albumin binder and said one or more further heavy-chain ISVD's all contain a V at position 11 and an L at position 89.

Again, all these polypeptides preferably contain a C-terminal extension X(n) (as described herein) and a D at position 1, and as further described herein may contain a serum albumin binding ISVD. They also have a half-live that is as further described herein.

The invention also relates to nucleotide sequences or nucleic acids that encode the albumin binders, compounds or polypeptides of the invention. The invention further includes genetic constructs that include the foregoing nucleotide sequences or nucleic acids and one or more elements for genetic constructs known per se. The genetic construct may be in the form of a plasmid or vector. Again, such constructs can be generally as described in the published patent applications of Ablynx N.V., such as for example WO 04/041862, WO 2006/122786, WO 2008/020079, WO 2008/142164 or WO 2009/068627.

The invention also relates to hosts or host cells that contain such nucleotide sequences or nucleic acids, and/or that express (or are capable of expressing), the albumin binders, compounds or polypeptides of the invention. Again, such host cells can be generally as described in the published patent applications of Ablynx N.V., such as for example WO 04/041862, WO 2006/122786, WO 2008/020079, WO 2008/142164 or WO 2009/068627.

The invention also relates to a method for preparing an albumin binder, compound or polypeptide of the invention, which method comprises cultivating or maintaining a host cell as described herein under conditions such that said host cell produces or expresses an albumin binder, compound or polypeptide of the invention, and optionally further comprises isolating the albumin binder, compound or polypeptide of the invention so produced. Again, such methods can be performed as generally described in the published patent applications of Ablynx N.V., such as for example WO 04/041862, WO 2006/122786, WO 2008/020079, WO 2008/142164 or WO 2009/068627.

The invention also relates to a pharmaceutical composition that comprises at least one compound or polypeptide of the invention, and optionally at least one pharmaceutically acceptable carrier, diluent or excipient. Such preparations, carriers, excipients and diluents may generally be as described in the published patent applications of Ablynx N.V., such as for example WO 04/041862, WO 2006/122786, WO 2008/020079, WO 2008/142164 or WO 2009/068627.

However, since the compounds or polypeptides of the invention have an increased half-life, they are preferably administered to the circulation. As such, they can be administered in any suitable manner that allows the compound or polypeptide of the invention to enter the circulation, such as intravenously, via injection or infusion, or in any other suitable manner (including oral administration, subcutaneous administration, intramuscular administration, administration through the skin, intranasal administration, administration via the lungs, etc.). Suitable methods and routes of administration will be clear to the skilled person, again for example also from the teaching of the published patent applications of Ablynx N.V., such as for example WO 04/041862, WO 2006/122786, WO 2008/020079, WO 2008/142164 or WO 2009/068627.

Thus, in another aspect, the invention relates to a method for the prevention and/or treatment of at least one disease or disorder that can be prevented or treated by the use of a compound or polypeptide of the invention, which method comprises administering, to a subject in need thereof, a pharmaceutically active amount of a compound or polypeptide of the invention, and/or of a pharmaceutical composition comprising the same. The diseases and disorders that can be prevented or treated by the use of a compound or polypeptide of the invention as described herein will generally be the same as the diseases and disorders that can be prevented or treated by the use of the therapeutic moiety or moieties that is/are present in the compound or polypeptide of the invention.

In the context of the present invention, the term "prevention and/or treatment" not only comprises preventing and/or treating the disease, but also generally comprises preventing the onset of the disease, slowing or reversing the progress of disease, preventing or slowing the onset of one or more symptoms associated with the disease, reducing and/or alleviating one or more symptoms associated with the disease, reducing the severity and/or the duration of the disease and/or of any symptoms associated therewith and/or preventing a further increase in the severity of the disease and/or of any symptoms associated therewith, preventing, reducing or reversing any physiological damage caused by the disease, and generally any pharmacological action that is beneficial to the patient being treated.

The subject to be treated may be any warm-blooded animal, but is in particular a mammal, and more in particular a human being. As will be clear to the skilled person, the subject to be treated will in particular be a person suffering from, or at risk from, the diseases and disorders mentioned herein.

In another embodiment, the invention relates to a method for immunotherapy, and in particular for passive immunotherapy, which method comprises administering, to a subject suffering from or at risk of the diseases and disorders mentioned herein, a pharmaceutically active amount of a compound or polypeptide of the invention, and/or of a pharmaceutical composition comprising the same.

The compound or polypeptide of the invention and/or the compositions comprising the same are administered according to a regime of treatment that is suitable for preventing and/or treating the disease or disorder to be prevented or treated. The clinician will generally be able to determine a suitable treatment regimen, depending on factors such as the disease or disorder to be prevented or treated, the severity of the disease to be treated and/or the severity of the symptoms thereof, the specific polypeptide of the invention to be used, the specific route of administration and pharmaceutical formulation or composition to be used, the age, gender, weight, diet, general condition of the patient, and similar factors well known to the clinician.

Generally, the treatment regimen will comprise the administration of one or more compounds or polypeptides of the invention, or of one or more compositions comprising the same, in one or more pharmaceutically effective amounts or doses. The specific amount(s) or doses to be administered can be determined by the clinician, again based on the factors cited above.

Generally, for the prevention and/or treatment of the diseases and disorders mentioned herein and depending on the specific disease or disorder to be treated, the potency and/or the half-life of the compounds or polypeptides of the invention to be used, the specific route of administration and the specific pharmaceutical formulation or composition used, the compounds or polypeptides of the invention will generally be administered in an amount between 1 gram and 0.01 microgram per kg body weight per day, preferably between 0.1 gram and 0.1 microgram per kg body weight per day, such as about 1, 10, 100 or 1000 microgram per kg body weight per day, either continuously (e.g., by infusion), as a single daily dose or as multiple divided doses during the day. The clinician will generally be able to determine a suitable daily dose, depending on the factors mentioned herein. It will also be clear that in specific cases, the clinician may choose to deviate from these amounts, for example on the basis of the factors cited above and his expert judgment. Generally, some guidance on the amounts to be administered can be obtained from the amounts usually administered for comparable conventional antibodies or antibody fragments against the same target administered via essentially the same route, taking into account however differences in affinity/avidity, efficacy, biodistribution, half-life and similar factors well known to the skilled person.

Also, as the compounds of the invention contain a half-life extending serum albumin binder of the invention, they do not need to be administered essentially continuously (e.g. by infusion), but they can be administered at suitable intervals (to be determined by the skilled person). For example, they can be administered (at a suitable dose) once every two days, once every four days, once weekly, once every two weeks and in some cases once every four weeks or even less frequently, for example by injection or infusion.

One aspect of the invention relates to a pharmaceutical composition comprising at least one compound or polypeptide of the invention wherein said composition is intended for administration at an interval between once weekly and once every 4 weeks, and in particular between once every 7 days and once every 21 days, such as once every 7 days or 14 days.

Usually, in the above method, a single polypeptide of the invention will be used. It is however within the scope of the invention to use two or more polypeptides of the invention in combination.

The polypeptides of the invention may also be used in combination with one or more further pharmaceutically active compounds or principles, i.e., as a combined treatment regimen, which may or may not lead to a synergistic effect. Again, the clinician will be able to select such further compounds or principles, as well as a suitable combined treatment regimen, based on the factors cited above and his expert judgement.

In particular, the polypeptides of the invention may be used in combination with other pharmaceutically active compounds or principles that are or can be used for the prevention and/or treatment of the diseases and disorders that can be prevented or treated with the fusion proteins or constructs of the invention, and as a result of which a synergistic effect may or may not be obtained.

The effectiveness of the treatment regimen used according to the invention may be determined and/or followed in any manner known per se for the disease or disorder involved, as will be clear to the clinician. The clinician will also be able, where appropriate and or a case-by-case basis, to change or modify a particular treatment regimen, so as to achieve the desired therapeutic effect, to avoid, limit or reduce unwanted side-effects, and/or to achieve an appropriate balance between achieving the desired therapeutic effect on the one hand and avoiding, limiting or reducing undesired side effects on the other hand.

Generally, the treatment regimen will be followed until the desired therapeutic effect is achieved and/or for as long as the desired therapeutic effect is to be maintained. Again, this can be determined by the clinician.

The subject to be treated may be any warm-blooded animal, in particular a mammal, and more in particular a human being. As will be clear to the skilled person, the subject to be treated will in particular be a person suffering from, or at risk from, the diseases and disorders mentioned herein.

Other aspects, embodiments, advantages and applications of the invention will become clear from the further description herein.

The invention will now be further described by means of the following non-limiting preferred aspects, examples and figures, in which:

FIG. 1 is a table listing some of the amino acid positions that will be specifically referred to herein and their numbering according to some alternative numbering systems (such as Aho and IMGT);

FIG. 2 shows an alignment of the Reference sequences referred to herein.

Figure 4:
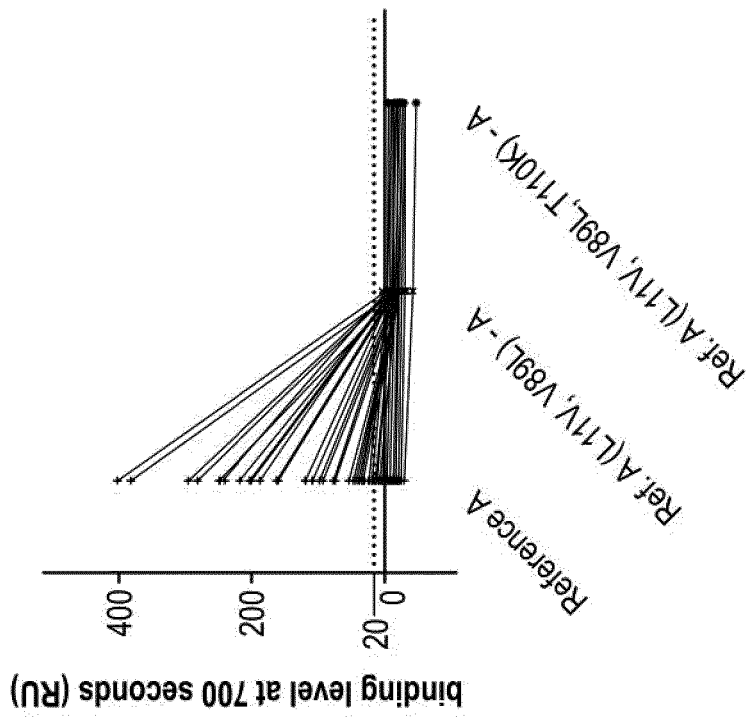
Figure 4:
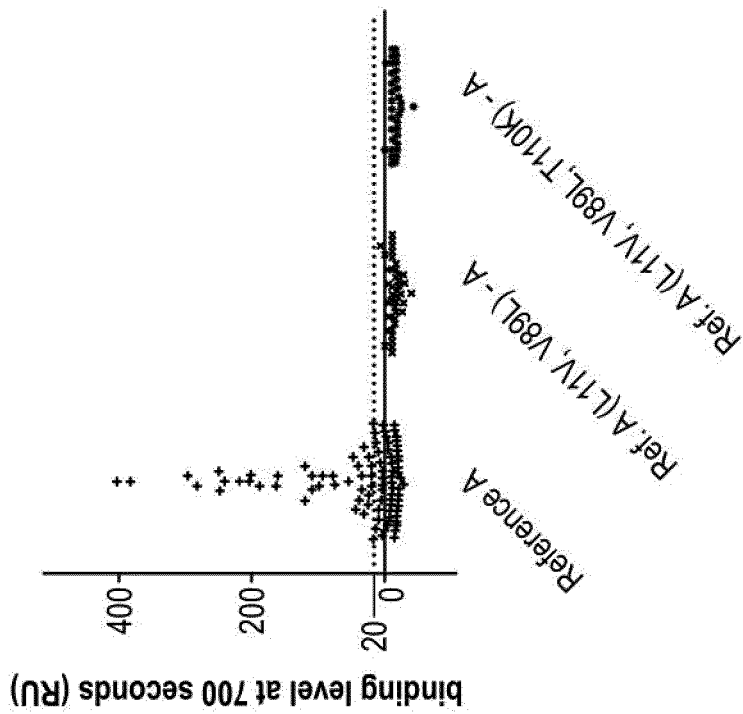
Figure 6:
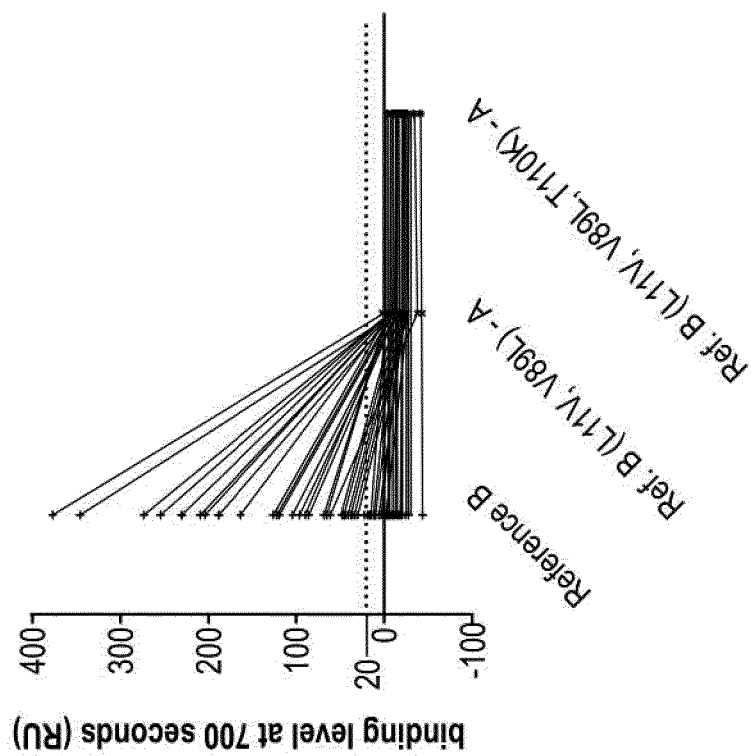
Figure 6:
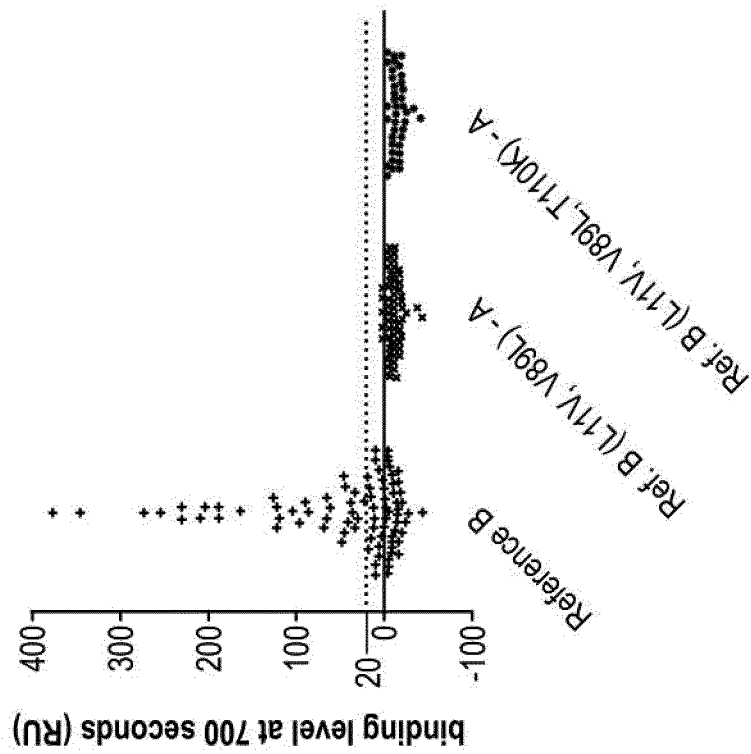
Figure 8:
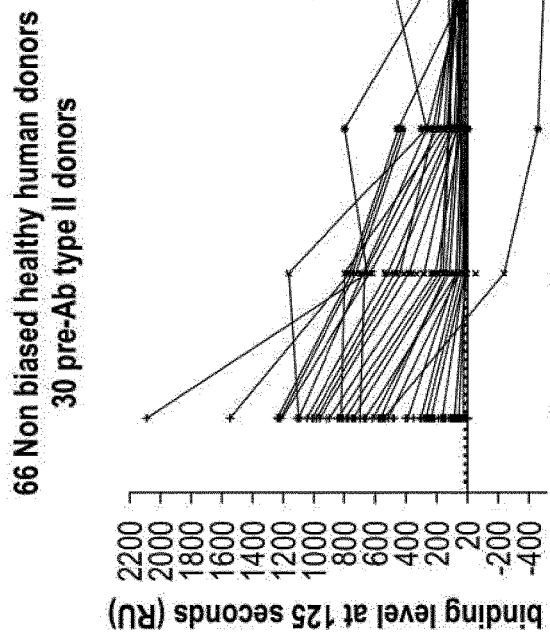
Figure 8:
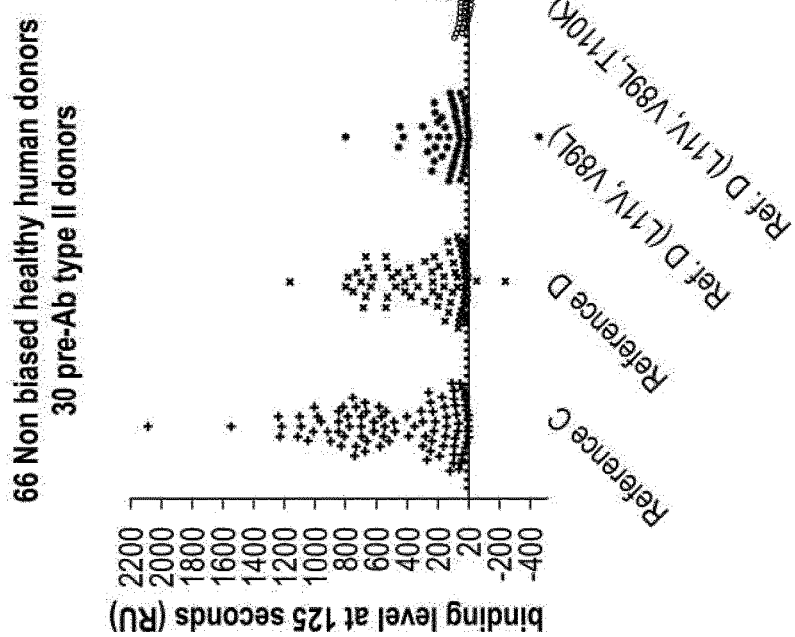
Figure 9:
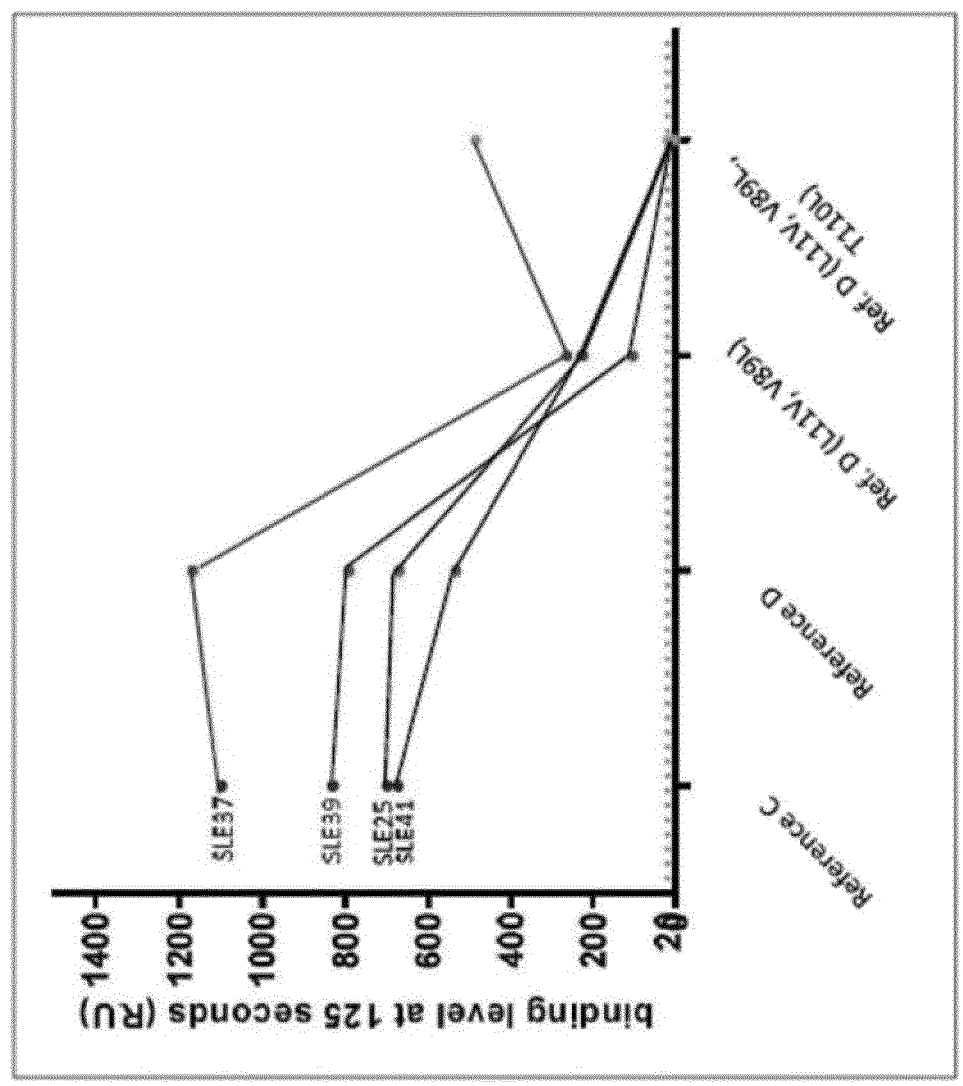

FIG. 3 lists the amino acid sequences referred to herein;

FIG. 4 shows two corresponding plots of data points obtained in Example 1 when 96 serum samples from human healthy subjects were tested for binding to Reference A and two representative variants of Reference A according to the invention (i.e. [Reference A+L11V+V89L+C-terminal alanine] and [Reference A+L11V+V89L+T110K+C-terminal alanine], respectively). Each dot represents the binding level for one of the 96 samples tested. The data points shown in the right hand panel and the left hand panel are the same; in the right hand panel the data points measured with each individual sample for each of the three compounds tested (i.e. Ref. A; Ref. A+L11V+V89L+114A; and Ref. A+L11V+V89L+T110K+114A) are connected by means of a line (as a result, the declination of the line gives an indication of the extent to which binding by pre-existing antibodies is reduced when the mutations of the invention and the C-terminal alanine are introduced);

FIG. 5 is a table listing the binding data (3 columns giving normalized PreAb binding levels (RU at 700) and 3 columns giving percentage of reduction in PreAb binding compared to the reference compound used, respectively) of the data points compiled in FIG. 4;

FIG. 6 shows two corresponding plots of data points obtained in Example 2 when 96 serum samples from human healthy subjects were tested for binding to Reference B and two representative variants of Reference B according to the invention (i.e. [Reference B+L11V+V89L+C-terminal alanine] and [Reference B+L11V+V89L+T110K+C-terminal alanine], respectively). Each dot represents the binding level for one of the 96 samples tested. The data points shown in the right hand panel and the left hand panel are the same; in the right hand panel the data points measured with each individual sample for each of the three compounds tested (i.e. Ref. B; Ref. B+L11V+V89L+114A; and Ref. B+L11V+V89L+T110K+114A) are connected by means of a line (as a result, the declination of the line gives an indication of the extent to which binding by pre-existing antibodies is reduced when the mutations of the invention and the C-terminal alanine are introduced);

FIG. 7 is a table listing the binding data (3 columns giving normalized PreAb binding levels (RU at 700) and 2 columns giving percentage of reduction in PreAb binding compared to the reference compound used, respectively) of the data points compiled in FIG. 6;

FIG. 8 shows two corresponding plots of data points obtained in Example 3 when 96 serum samples (66 from human healthy subjects and 30 from subjects assumed to contain pre-existing antibodies that can bind in the presence of a C-terminal alanine, including 13 samples from SLE patients) were tested for binding to Reference C, Reference D and two representative variants of Reference D according to the invention (i.e. [Reference D+L11V+V89L] and [Reference D+L11V+V89L+T110K], respectively). Each dot represents the binding level for one of the 96 samples tested. The data points shown in the right hand panel and the left hand panel are the same; in the right hand panel the data points measured with each individual sample for each of the four compounds tested (i.e. Ref C; Ref. D; Ref. D+L11V+V89L; and Ref. D+L11V+V89L+T110K) are connected by means of a line (as a result, the declination of the line gives an indication of the extent to which binding by pre-existing antibodies is reduced when the mutations of the invention and the C-terminal alanine are introduced);

FIG. 9 shows a plot of the data points obtained for four of the SLE samples that were tested in Example 3. The data points measured with for individual sample (i.e. "SLE25", "SLE37", "SLE39" and "SLE41", respectively) are connected by means of a lines (as a result, the declination of each line gives an indication of the extent to which binding by pre-existing antibodies is reduced in each sample when the mutations of the invention are introduced);

FIG. 10 is a table listing the binding data (4 columns giving normalized PreAb binding levels (RU at 700) and 3 columns giving percentage of reduction in PreAb binding compared to the reference compounds used, respectively) of the data points compiled in FIG. 8.

EXPERIMENTAL PART

The human samples used in the Experimental Part below were either obtained from commercial sources or from human volunteers (after all required consents and approvals were obtained) and were used in according with the applicable legal and regulatory requirements (including but not limited to those regarding medical secret and patient privacy)

In the Examples below, unless explicitly indicated otherwise, the binding of pre-existing antibodies that are present in the samples used (i.e. from healthy volunteers, rheumatoid arthritis (RA) patients and SLE patients) to the Nanobodies tested was determined using ProteOn as follows:

Nanobodies were captured either on serum albumin or via a FLAG3 tag using monoclonal anti-FLAG M2.

In case of binding of pre-existing antibodies on Nanobodies captured on human serum albumin (HSA) was evaluated using the ProteOn XPR36 (Bio-Rad Laboratories, Inc.). PBS/Tween (phosphate buffered saline, pH7.4, 0.005% Tween20) was used as running buffer and the experiments were performed at 25° C. The ligand lanes of a ProteOn GLC Sensor Chip were activated with EDC/NHS (flow rate 30 μl/min) and HSA was injected at 10 μg/ml in ProteOn Acetate buffer pH4.5 (flow rate 100 μl/min) to render immobilization levels of approximately 3200 RU. After immobilization, surfaces were deactivated with ethanolamine HCl (flow rate 30 μl/min). Nanobodies were injected for 2 minutes at 45 μl/min over the HSA surface to render a Nanobody capture level of approximately 200 RU. The samples containing pre-existing antibodies were centrifuged for 2 minutes at 14,000 rpm and supernatant was diluted 1:10 in PBS-Tween20 (0.005%) before being injected for 2 minutes at 45 μl/min followed by a subsequent 400 seconds dissociation step. After each cycle (i.e. before a new Nanobody capture and blood sample injection step) the HSA surfaces were regenerated with a 2 minute injection of HCl (100 mM) at 45 μl/min. Sensorgram processing and data analysis was performed with ProteOn Manager 3.1.0 (Bio-Rad Laboratories, Inc.). Sensorgrams showing pre-existing antibody binding were obtained after double referencing by subtracting 1) Nanobody-HSA dissociation and 2) non-specific binding to reference ligand lane. Binding levels of pre-existing antibodies were determined by setting report points at 125 seconds (5 seconds after end of association). Percentage reduction in pre-existing antibody binding was calculated relative to the binding levels at 125 seconds of a reference Nanobody.

In case of binding of pre-existing antibodies on FLAG-tagged Nanobodies captured on monoclonal anti-FLAG M2 (Sigma) was evaluated using the ProteOn XPR36 (Bio-Rad Laboratories, Inc.). PBS/Tween (phosphate buffered saline, pH7.4, 0.005% Tween20) was used as running buffer and the experiments were performed at 25° C. The ligand lanes of a ProteOn GLC Sensor Chip were activated with EDC/NHS (flow rate 30 l/min) and anti-FLAG M2 mAb was injected at 10 μg/ml in ProteOn Acetate buffer pH4.5 (flow rate 100 l/min) to render immobilization levels of approximately 4000 RU. After immobilization, surfaces were deactivated with ethanolamine HCl (flow rate 30 μl/min). Nanobodies were injected for 2 minutes at 45 μl/min over the anti-FLAG M2 surface to render a Nanobody capture level of approximately 100 RU. To reduce non-specific binding of the blood samples to the anti-FLAG M2 surface 100 nM 3×FLAG peptide (Sigma) was added to the blood samples. The samples containing pre-existing antibodies were centrifuged for 2 minutes at 14,000 rpm and supernatant was diluted 1:10 in PBS-Tween20 (0.005%) before being injected for 2 minutes at 45 l/min followed by a subsequent 600 seconds dissociation step. After each cycle (i.e. before a new Nanobody capture and blood sample injection step) the anti- FLAG M2 surfaces were regenerated with a 10 seconds injection of Glycine pH1.5 (10 mM) at 150 µl/min. Sensorgram processing and data analysis was performed with ProteOn Manager 3.1.0 (Bio-Rad Laboratories, Inc.). Sensorgrams showing pre-existing antibody binding were obtained after double referencing by subtracting 1) Nanobody-anti-FLAG M2 dissociation and 2) non-specific binding to reference ligand lane. Binding levels of pre-existing antibodies were determined by setting report points at 125 seconds (5 seconds after end of association). Percentage reduction in pre-existing antibody binding was calculated relative to the binding levels at 125 seconds of a reference Nanobody.

Example 1: Introducing the Mutations of the Invention in Reference a (SEQ ID NO: 1) Leads to a Reduction in Binding by Pre-Existing Antibodies Reference A (SEQ ID NO: 1) and two representative examples of the improved variants of Reference A carrying the mutations according to the invention (SEQ ID NOs: 37 and 38, both with alanine-extension and tested with an N-terminal HIS6-FLAG3 tag, see SEQ ID NO:100) were tested for binding by pre-existing antibodies that are present in the samples from 96 serum samples from healthy human volunteers. The compounds were captured using the FLAG-tag and binding was measured using ProteOn according to the protocol given in the preamble to this Experimental Part.

The results are shown in FIG. 4. FIG. 5 lists the results for each of the samples that forms one of the data points in FIG. 4.

It can be seen that for most of the 96 samples tested, introducing the mutations according to the invention leads to a reduction in pre-existing antibody binding, with the degree of reduction generally being dependent on the level to which the pre-existing antibodies in each sample were capable of binding to Reference A.

Example 2: Introducing the Mutations of the Invention in Reference B (SEQ ID NO: 2) Leads to a Reduction in Binding by Pre-Existing Antibodies Reference B (SEQ ID NO:2) and two representative examples of the improved variants of Reference B carrying the mutations according to the invention (SEQ ID NOs: 65 and 66, both with alanine-extension and tested with an N-terminal HIS6-FLAG3 tag, see SEQ ID NO: 100) were tested for binding by pre-existing antibodies that are present in the samples from 96 serum samples from healthy human volunteers. The compounds were captured using the FLAG-tag and binding was measured using ProteOn according to the protocol given in the preamble to this Experimental Part.

The results are shown in FIG. 6. FIG. 7 lists the results for each of the samples that forms one of the data points in FIG. 6.

Similar to Example 1, it can be seen that for most of the 96 samples tested, introducing the mutations according to the invention leads to a reduction in pre-existing antibody binding, with the degree of reduction generally being dependent on the level to which the pre-existing antibodies in each sample were capable of binding to Reference B.

Example 3: Introducing the Mutations of the Invention in Reference C (SEQ ID NO: 3) and Reference D (SEQ ID NO: 4) Leads to a Reduction in Binding by Pre-Existing Antibodies Reference C (SEQ ID NO: 3), Reference D (SEQ ID NO: 4) and two representative examples of the improved variants of Reference C and Reference D carrying the mutations according to the invention (SEQ ID NOs: 93 and 94, both with an alanine-extension as present in Reference D and tested with an N-terminal HIS6-FLAG3 tag, see SEQ ID NO:100) were tested for binding by pre-existing antibodies that are present in the samples from 66 serum samples from healthy human volunteers and 30 samples assumed to contain pre-existing antibodies capable of binding even when a C-terminal alanine is present (of which 13 were from SLE patients). The compounds were captured on human serum albumin and binding was measured using ProteOn according to the protocol given in the preamble to this Experimental Part.

The results are shown in FIG. 8. In FIG. 9, details are given for 4 representative SLE samples. FIG. 10 lists the results for each of the samples that forms one of the data points in FIG. 8.

Similar to Examples 1 and 2, it can be seen that for most of the 96 samples tested, introducing the mutations according to the invention for the great majority of samples leads to a reduction in pre-existing antibody binding, with the degree of reduction generally being dependent on the level to which the pre-existing antibodies in each sample were capable of binding to Reference C or Reference D.

The entire contents of all of the references (including literature references, issued patents, published patent applications, and co-pending patent applications) cited throughout this application are hereby expressly incorporated by reference, in particular for the teaching that is referenced hereinabove.

---

The invention claimed is:

1. An immunoglobulin single variable domain that binds to serum albumin, comprising:
   a CDR1 according to Abm that is the following sequence: GFTFDTSSML (SEQ ID NO:13); and
   a CDR2 according to Abm that is the following sequence: VIHQSGTPTY (SEQ ID NO:14); and
   a CDR3 according to Abm that is the following sequence: FPSSRMKFDY (SEQ ID NO: 15); and having:
   an amino acid residue L or V at position 11; and
   an amino acid residue T, V or L at position 89; and
   an amino acid residue T, K or Q at position 110; and
   an amino acid residue S, K or Q at position 112;
   such that (i) position 89 is T; or (ii) position 89 is L and position 11 is V; or (iii) position 89 is L and position 110 is K or Q; or (iv) position 89 is L and position 112 is K or Q; or (v) position 89 is L and position 11 is V and position 110 is K or Q; or (vi) position 89 is L and position 11 is V and position 112 is K or Q; or (vii) position 11 is V and position 110 is K or Q; or (viii) position 11 is V and position 112 is K or Q, and wherein the positions are according to Kabat numbering.

2. The immunoglobulin single variable domain according to claim 1, which comprises the following amino acid residues at positions according to Kabat numbering:
   11V in combination with 89L; or
   11V in combination with 110K or 110Q; or
   11V in combination with 112K or 112Q; or
   11V in combination with 89L and 110K or 110Q; or
   11V in combination with 89L and 112K or 112Q.

3. The immunoglobulin single variable domain according to claim 1, which comprises the following amino acid residues at positions according to Kabat numbering:
   89L in combination with 11V; or
   89L in combination with 110K or 110Q; or
   89L in combination with 112K or 112Q; or
   89L in combination with 11V and 110K or 110Q; or
   89L in combination with 11V and 112K or 112Q.

4. The immunoglobulin single variable domain according to claim 1, which comprises the following amino acid residues at positions according to Kabat numbering:
   110K or 110Q in combination with 11V; or
   110K or 110Q in combination with 89L; or
   110K or 110Q in combination with 11V and 89L.

5. The immunoglobulin single variable domain according to claim 1, which comprises the following amino acid residues at positions according to Kabat numbering:
112K or 112Q in combination with 11V; or
112K or 112Q in combination with 89L; or
112K or 112Q in combination with 11V and 89L.

6. The immunoglobulin single variable domain according to claim 1, which comprises the following amino acid residue at a position according to Kabat numbering:
89T.

7. The immunoglobulin single variable domain according to claim 1 further comprising a C-terminal extension $(X)_n$, in which n is 1 to 10; and each X is an amino acid residue that is independently chosen, and optionally independently chosen from the group consisting of alanine (A), glycine (G), valine (V), leucine (L) or isoleucine (I).

8. The immunoglobulin single variable domain according to claim 1 further comprising a D and/or E1D mutation at position 1 according to Kabat numbering.

9. Immunoglobulin single variable domain that binds to serum albumin, wherein the immunoglobulin single variable domain comprises an amino acid sequence that is chosen from the amino acid sequences of SEQ ID NOs: 72 to 99.

10. The immunoglobulin single variable domain of claim 9 consisting of an amino acid sequence that is one of the following sequences: SEQ ID NO:72, SEQ ID NO:73, SEQ ID NO:74, SEQ ID NO:75, SEQ ID NO:76, SEQ ID NO:77, SEQ ID NO:79, SEQ ID NO:80, SEQ ID NO:81, SEQ ID NO:82, SEQ ID NO:83, SEQ ID NO:84, SEQ ID NO:85, SEQ ID NO:86, SEQ ID NO:87, SEQ ID NO:88, SEQ ID NO:89, SEQ ID NO:90, SEQ ID NO:91, SEQ ID NO:93, SEQ ID NO:94, SEQ ID NO:95, SEQ ID NO:96, SEQ ID NO:97, SEQ ID NO:98 or SEQ ID NO:99.

11. The immunoglobulin single variable domain of claim 9 having an amino acid sequence that is one of the following sequences: SEQ ID NO: 78 or SEQ ID NO: 92.

* * * * *